(12) United States Patent
Wu-Wong

(10) Patent No.: US 9,796,792 B2
(45) Date of Patent: *Oct. 24, 2017

(54) METAL ION-FUNCTIONAL FIBER COMPONENT COMPLEX COMPOSITIONS, PREPARATION AND USES THEREOF

(71) Applicant: Vidasym, Inc., Libertyville, IL (US)

(72) Inventor: Jinshyun Ruth Wu-Wong, Libertyville, IL (US)

(73) Assignee: Vidasym, Inc., Libertyville, IL (US)

( * ) Notice: Subject to any disclaimer, the term of this patent is extended or adjusted under 35 U.S.C. 154(b) by 105 days.

This patent is subject to a terminal disclaimer.

(21) Appl. No.: 14/765,087

(22) PCT Filed: Mar. 4, 2014

(86) PCT No.: PCT/US2014/020205
§ 371 (c)(1),
(2) Date: Jul. 31, 2015

(87) PCT Pub. No.: WO2014/138016
PCT Pub. Date: Sep. 12, 2014

(65) Prior Publication Data
US 2015/0368369 A1    Dec. 24, 2015

Related U.S. Application Data

(60) Provisional application No. 61/774,964, filed on Mar. 8, 2013, provisional application No. 61/877,680, filed on Sep. 13, 2013.

(51) Int. Cl.
*C08B 15/05* (2006.01)
*A23L 2/52* (2006.01)
(Continued)

(52) U.S. Cl.
CPC .......... *C08B 15/05* (2013.01); *A23L 2/52* (2013.01); *A23L 33/165* (2016.08); *A23L 33/21* (2016.08);
(Continued)

(58) Field of Classification Search
None
See application file for complete search history.

(56) References Cited

U.S. PATENT DOCUMENTS 3,324,109 A    6/1967    Eichel
3,563,978 A    2/1971    Ochs
(Continued)

FOREIGN PATENT DOCUMENTS

CN    1104890 A    7/1995
CN    1646549 A    7/2005
(Continued)

OTHER PUBLICATIONS

Reinhold et al. "Binding of iron by fiber of wheat and maize", Am. J. Clin. Nutr. (1981) 34, pp. 1384-1391.*
(Continued)

*Primary Examiner* — Carlos Azpuru
*Assistant Examiner* — Casey Hagopian
(74) *Attorney, Agent, or Firm* — Swanson & Bratschun, L.L.C.

(57) ABSTRACT

Compositions comprising metal ions or clusters such as ferrous and/or ferric iron compounds or magnesium, zinc, lanthanum and other metal ion compounds and fiber components such as gum Arabic in a complex, methods for preparing such compositions of matter, and the use thereof for treatment of adsorbing certain accessible targets in the gastrointestinal tract and in an extracorporeal system, are provided herein.

18 Claims, 34 Drawing Sheets

(51) Int. Cl.
A61K 31/715 (2006.01)
C08B 31/00 (2006.01)
C08B 35/00 (2006.01)
C08B 37/02 (2006.01)
C08B 37/00 (2006.01)
A23L 33/165 (2016.01)
A23L 33/21 (2016.01)

(52) U.S. Cl.
CPC ............ *A61K 31/715* (2013.01); *C08B 31/00* (2013.01); *C08B 35/00* (2013.01); *C08B 37/0021* (2013.01); *C08B 37/0045* (2013.01); *C08B 37/0054* (2013.01); *C08B 37/0096* (2013.01); *A23V 2002/00* (2013.01)

(56) References Cited

U.S. PATENT DOCUMENTS

| | | | |
|---|---|---|---|
| 3,591,616 | A | 7/1971 | Baldt |
| 4,225,592 | A | 9/1980 | Lakatos et al. |
| 5,624,668 | A | 4/1997 | Lawrence et al. |
| 5,662,922 | A | 9/1997 | Christensen |
| 6,022,619 | A | 2/2000 | Kuhn |
| 6,174,442 | B1 | 1/2001 | Geisser et al. |
| 7,674,780 | B2 | 3/2010 | Newton et al. |
| 9,566,303 | B2 | 2/2017 | Wu-Wong |
| 2003/0191090 | A1 | 10/2003 | Andreasen et al. |
| 2005/0084539 | A1 | 4/2005 | Handa et al. |
| 2005/0107253 | A1 | 5/2005 | Sano |
| 2005/0158431 | A1 | 7/2005 | Knoblock et al. |
| 2006/0269535 | A1 | 11/2006 | Naidu et al. |
| 2008/0145410 | A1 | 6/2008 | Ambuhl et al. |
| 2008/0234226 | A1 | 9/2008 | Erichsen et al. |
| 2010/0035830 | A1 | 2/2010 | Reim et al. |
| 2010/0305063 | A1 | 12/2010 | Reim et al. |
| 2011/0086097 | A1 | 4/2011 | Kaufmann et al. |
| 2012/0094355 | A1 | 4/2012 | Medoff et al. |
| 2014/0242187 | A1 | 8/2014 | Wu-Wong et al. |

FOREIGN PATENT DOCUMENTS

| | | | |
|---|---|---|---|
| CN | 1798754 A | | 7/2006 |
| DE | 195 47 356 | | 6/1997 |
| EP | 0648495 | | 4/1995 |
| EP | 1457256 | | 9/2004 |
| EP | 1481982 A1 | | 12/2004 |
| EP | 2204432 A1 | | 7/2010 |
| EP | 2204432 A8 | | 7/2010 |
| JP | H5-238940 A | | 9/1993 |
| NZ | 560350 | | 10/2010 |
| NZ | 574271 | | 5/2011 |
| WO | WO 97/22266 | | 6/1997 |
| WO | WO 02/46241 | | 6/2002 |
| WO | WO 2005/000210 A2 | | 1/2005 |
| WO | WO 2006/133334 | | 12/2006 |
| WO | WO 2009/078037 | | 6/2009 |
| WO | WO 2013/056085 | | 4/2013 |
| WO | WO 2014/138016 | | 9/2014 |
| YU | WO 0246241 A2 * | 6/2002 | ........... A61K 9/0019 |

OTHER PUBLICATIONS

Fernandez et al. "Components of fiber bind iron in vitro", Am. J. Clin. Nutr. (1982) 35, pp. 100-106.*
Behall et al. (May 1989) Diabetes Care 12(5):357-364, "Effect of Guar Gum on Mineral Balances in NIDDM Adults".
Bilba and Arsene (2008) Composites Part A 39: 1488-1495, "Silane treatment of bagasse fiber for reinforcement of cementitious composites".
Cook et al. (Dec. 1983) Gastroenterology 85:1354-1358 "Effect of Fiber on Nonheme Iron Absorption".
Coudray et al. (2003) J Nutr. 133:1-4, "Effects of Dietary Fibers on Magnesium Absorption in Animals and Humans".
Eberhardt et al. (2006) Bioresource Technology 97: 2371-2376, "Phosphate removal by refined aspen wood fiber treated with carboxymethyl cellulose and ferrous chloride".
EP Search Report dated Jul. 1, 2015 in EP12840785.5.
EP Search Report dated Jun. 2, 2015 in EP12840785.5.
Fernandez et al. (Jan. 1982) The American Journal of Clinical Nutrition 35(1):100-106, "Components of fiber bind iron in vitro".
Greger (1999) J Nutr. 129:1434S-1435S, "Nondigestible Carbohydrates and Mineral Bioavailability".
Gustafsson et al. (2003) Polymer 44:661-670, "The ultrastructure of spruce kraft pulps studied by atomic force microscopy (AFM) and X-ray photoelectron spectroscopy (XPS)".
Han et al. (Sep. 2003) 6th Inter-Regional Conference on Environment-Water, "Land and Water Use Planning and Management," Albacete, Spain,, pp. 1-11, "Removal of Phosphorous Using Chemically Modified Lignocellulosic Materials".
International Preliminary Report on Patentability dated Apr. 15, 2014 in PCT/US2012/060011.
International Preliminary Report on Patentability dated Sep. 8, 2015 in PCT/US2014/020205.
International Search Report and Written Opinion dated Dec. 24, 2012 in PCT/US2012/060011.
International Search Report and Written Opinion dated Jun. 9, 2014 in PCT/US2014/20205.
Leigh (Aug. 1983) The American Journal of Clinical Nutrition 38(2):202-213, "Effects of pH and chelating agents on iron binding by dietary fiber: implications for iron availability".
Raschka et al. (2005) Bone 37(5):728-735, "Mechanisms underlying the effects of inulin-type fructans on calcium absorption in the large intestine of rats".
Reinhold et al. (Jul. 1981) The American Journal of Clinical Nutrition 34:1384-1391, "Binding of iron by fiber of wheat and maize".
Scholz-Ahrens et al. (2007) J Nutr. 137 (11 Suppl): 2513S-2523S), "Inulin and Oligofructose and Mineral Metabolism: The Evidence from Animal Trials".
Spencer et al. (1991) J Nutr 121:1976-1983 , "Effect of Oat Bran Muffins on Calcium Absorption and Calcium, Phosphorus, Magnesium and Zinc Balance in Men".
Spengler et al. (1994) Eur. J. Clin. Chem. Clin. Biochem., 32:733-739, "Characterization and Extracorporeal Application of a New Phosphate-Binding Agent".
Unnithan et al. ( 2002) J. Appl. Polym. Sci. 84, 2541-2553, "Ability of Iron(III)-Loaded Carboxylated Polyacrylamide Grafted Sawdust to Remove Phosphate Ions from Aqueous Solution and Fertilizer Industry Wastewater: Adsorption Kinetics and Isotherm Studies".
Wang et al. (2010) BioResources 5(3): 1799-1810, "Study on Lignin Coverage of Masson Pine Fiber".
WuWong et al. (2014) Pharmacology Research & Perspective, 2(3):e00042:1-12, "VS-501: a novel, nonabsorbed, calcium- and aluminum-free, highly effective phosphate binder derived from natural plant polymer".
Ciesielski et al. (2008) EJPAU 11(2), pp. 25 "Metal Complexes of Xanthan Gum".
Report of the Dietary Fiber Definition Committee to the Board of Directors of the American Association of Cereal Chemists. Cereal Foods World. Mar. 2001;46(3):112-26.
Platt, et al. (1984) J. Food Sci., 49(2):531-535, "Binding of Iron by Cellulose, Lignin, Sodium Phytate and Beta-Glucan, Alone and in Combination, Under Simulated Gastrointestinal pH Conditions".
European Search Report issued in EP 14761117.2 dated Sep. 12, 2016.

* cited by examiner

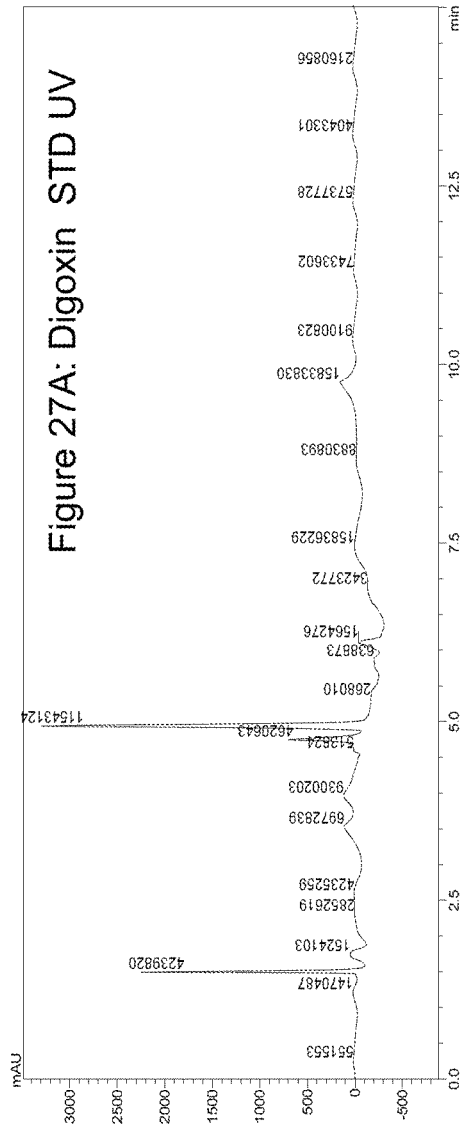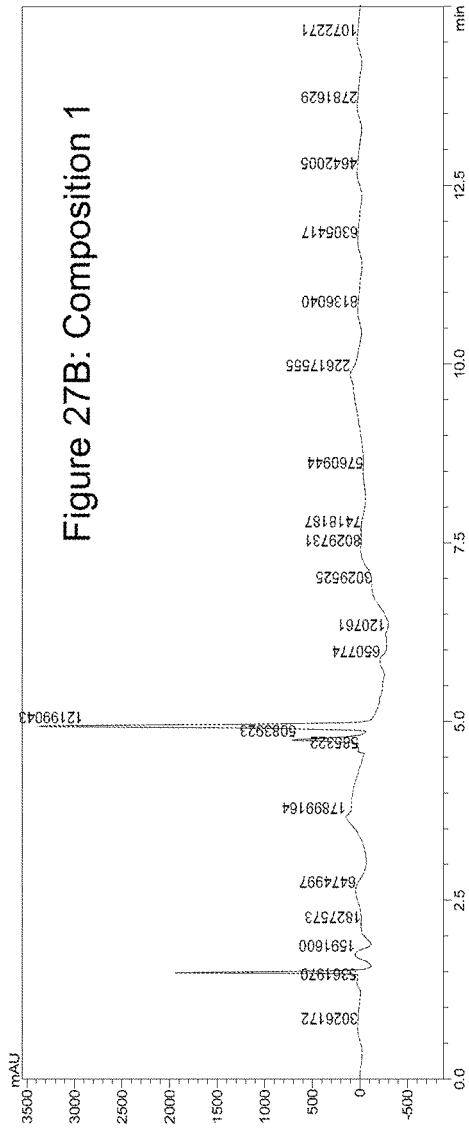

METAL ION-FUNCTIONAL FIBER COMPONENT COMPLEX COMPOSITIONS, PREPARATION AND USES THEREOF

RELATED APPLICATIONS

This application is a 35 U.S.C. §371 national phase application of International PCT Application Ser. No. PCT/US2014/020205, filed Mar. 4,2014. International PCT Application Ser. No. PCT/US2014/020205 claims the benefit of U.S. Provisional Application Ser. No. 61/774,964, filed Mar. 8, 2013 and U.S. Provisional Application Ser. No. 61/877,680, filed Sep. 13, 2013. Each of these applications is incorporated herein by reference in their entirety for all purposes.

FIELD OF INVENTION

The present application relates to medicinal compositions prepared from a metal ion-functional fiber component complex that is useful in adsorbing certain accessible targets in the gastrointestinal (GI) tract and in an extracorporeal system.

BACKGROUND

A diet high in fiber benefits health. Fiber adds bulk to the stool to alleviate constipation. It increases food volume without increasing caloric content. Fiber adsorbs water and forms a gel-like composition during digestion, slowing the emptying of the stomach and intestinal transit, shielding carbohydrates from enzymes, and delaying absorption of glucose by the gastrointestinal tract. Fiber consumption can lower total and LDL cholesterol.

Total Fiber is the sum of Dietary Fiber and Functional Fiber. Dietary Fiber consists of nondigestible carbohydrates and lignin that are intrinsic and intact in plants. Functional Fiber consists of isolated, nondigestible carbohydrates that have beneficial physiological effects in humans (Dietary Reference Intakes for Energy, Carbohydrate, Fiber, Fat, Fatty Acids, Cholesterol, Protein, and Amino Acids (Macronutrients), 2005, Chapter 7: Dietary, Functional and Total fiber. U.S. Department of Agriculture, National Agricultural Library and National Academy of Sciences, Institute of Medicine, Food and Nutrition Board).

The composition of dietary fiber varies greatly depending on the source (Cummings, What is fiber in "Fiber in human nutrition", 1976, 1-23). Fibers from fruits and vegetables such as apples, citrus, sunflowers, sugar beet are rich in pectin; fibers from grains such as oat, barley, wheat are rich in β-glucan; cellulose is one third or less of the total fiber in most foods, except for legumes, in which it was about one half; gum is usually present in seed (Marlett, J Am Diet Assoc. 1992, 92:175-86; Dietary Reference Intakes for Energy, Carbohydrate, Fiber, Fat, Fatty Acids, Cholesterol, Protein, and Amino Acids (Macronutrients), 2005, Chapter 7: Dietary, Functional and Total fiber. U.S. Department of Agriculture, National Agricultural Library and National Academy of Sciences, Institute of Medicine, Food and Nutrition Board). According to the U.S. Department of Agriculture, most fiber components such as gum and cellulose can be classified as Dietary Fiber or Functional Fiber, depending on whether it is naturally occurring in food (Dietary Fiber) or added to foods (Functional Fiber).

The composition of fiber can be broadly separated into two categories: (1) soluble and (2) insoluble. Soluble fiber dissolves in water. Insoluble fiber does not dissolve in water. Both soluble and insoluble dietary fiber pass from the small intestine to the large intestine only affected by their absorption of water (insoluble fiber) or dissolution in water (soluble fiber). Cellulose, lignin, xylan, etc. are insoluble fiber, while dextrin, glucan, gum, inulin, lactulose pectin, starch, etc. are soluble fiber.

According to published papers (Behall et al. 1989, Diabetes Care 12:357-364; Spencer et al. 1991, J Nutr 121: 1976-1983; Greger J L, J Nutr. 1999, 129:1434S-5S; Coudray et al. J Nutr. 2003, 133:1-4; Raschka et al. Bone 2005, 37 (5):728-735; Scholz-Ahrens et al. J Nutr. 2007, 137 (11 Suppl):25135-25235), nondigestible oligosaccharides have been shown to increase the absorption of several minerals (calcium, magnesium, in some cases phosphorus) and trace elements (mainly copper, iron, zinc). The stimulation of absorption was more pronounced when the demand for minerals was high. How fibers mediate this effect include different mechanisms such as acidification of the intestinal lumen by short-chain fatty acids increasing solubility of minerals in the gut, enlargement of the absorption surface, increased expression of calcium-binding proteins mainly in the large intestine, etc.

Meanwhile the study by Shah et al. (Diabetes Care, 2009, 32:990-995) showed that fiber does not significantly affect the intake of calcium and other minerals. Reinhold at al. showed that dietary fiber from wheat and maize may block iron absorption (The American Journal of Clinical Nutrition, 1981, 34:1384-1391), but Cook et al. showed that inhibition of iron absorption is a not a universal property of fiber (Cook et al., Gastroenterology, 1983, 85:1354-1358).

Different functional fiber components have been shown to exhibit different benefits (Dietary Fibre: Components and functions, edited by Salovaara, Gates and Tenkanen, 2007). For example, concentrated oat β-glucan and gum Arabic lowers serum cholesterol in humans (Queenan et al., Nutrition Journal 2007, 6:6; Ross et al., Am J Clin Nutr, 1983, 37: 368-75).

Metal ions such as calcium acetate or carbonate, magnesium and lanthanum carbonate, and aluminum carbonate or hydroxide have been used to treat hyperphosphatemia in chronic kidney disease (CKD) for many years (Daugirdas et al., Semin Dial, 2011, 24:41-49). Compounds based on iron ions such as polynuclear iron(III)-oxyhydroxide and ferric citrate are in development for treating hyperphosphatemia in CKD (Phan et al., J Pharmacol Exp Ther, 2013, 346:281-289; Lida et al. Am J Nephrol, 2013, 37:346-358). These metal ions bind phosphate in the GI, but also get absorbed into the body and often cause undesirable systemic side effects. For example, phosphate binders based on calcium ions are known to increase hypercalcemia, and aluminum ions are known to cause aluminum toxicity.

Many metal ions are important for health, but most also are toxic when present at higher than normal concentrations. It would be of value to create novel compositions using a functional fiber component and metal ions that have favorable properties for therapeutic and nutritional use. Such compositions that bind undesirable elements such as phosphate in the GI without systemic exposure (i.e. non-absorbable) will provide substantial benefits.

Metal ion absorption mainly occurs in the small intestine. Many studies have been done for the absorption of calcium and iron. Absorption of dietary iron is a variable process. The amount of iron absorbed compared to the amount ingested typically ranges from 5% to 35% for heme iron, depending on types of iron used. (Monson E R., J Am Dietet Assoc. 1988; 88:786-790). The absorption for non-heme iron ranges from 2% to 20% for iron in plant foods such as rice, maize, black beans, soybeans and wheat. (Tapiero H, Gate L, Tew K D., Biomed Pharmacother. 2001; 55:324-332).

Preparation of complexes of carbohydrates/polysaccharides such as dextran, dextrose, maltose, sucrose, and fructose with iron compounds have been disclosed in many patents and publications, which typically concern an absorbable composition in the GI tract used to increase systemic iron delivery to treat iron deficiency anemia.

Studies have shown that these iron-carbohydrates greatly enhance iron absorption in the GI tract and are useful for treating iron deficiency and anemia (Hall and Ricketts, Journal of Pharmacy and Pharmacology, 1968, 20:662-664; Pabón et al., Arch Latinoam Nutr. 1986, 36:688-700).

Spengler et al. in 1994 (Eur. J. Clin. Chem. Clin. Biochem., 1994, 32:733) describes a method for preparing an insoluble iron(III) oxide hydroxide porous support by linking $FeCl_3 \cdot 6H_2O$ to dextran using NaOH as the catalyst. WO 2009/078037 describes a process for manufacture of iron sucrose complex to treat anemia. U.S. Pat. No. 7,674,780 describes a process for preparing an iron-sucrose complex, substantially free of excipients, for providing an iron-sucrose complex co-precipitated with sucrose, and for providing iron-sucrose complexes in aqueous solution.

U.S. Publication 2008/0234226 mentions the use of iron (III) complex compounds with carbohydrates or derivatives thereof for the preparation of a medicament for oral treatment of iron deficiency states in patients with chronic inflammatory bowel disease, in particular Crohn's disease and colitis ulcerosa.

U.S. Publication 2010/0035830 describes iron-carbohydrate complex compounds which contain iron(II) in addition to iron(III), processes for their preparation, medicaments containing them, and the use thereof for treatment of iron deficiency anemia.

U.S. Pat. No. 5,624,668 describes ferric oxyhydroxide-dextran compositions for treating iron deficiency having ellipsoidal particles with a preferred molecular weight range of about 250,000 to 300,000 Daltons.

The textile industry uses particulates of iron oxides as pigments to dye fabrics. In addition, iron oxide is applied to textile fibers in an attempt to increase the conductivity of the synthetic fiber.

Biomass, either in its native state, or chemically modified, can be used to capture water pollutants and nutrients.

Studies have shown that iron adsorbed on synthetic filtration media or biomass can remove phosphates from water (Unnithan et al., J. Appl. Polym. Sci. 2002, 84:2541-2553; Han et al., 6th Inter-Regional Conference on Environment-Water, "Land and Water Use Planning and Management," Albacete, Spain, 2003, pp. 1-11). Treating refined aspen wood fiber with iron-salt solutions demonstrated limited capacities to remove (ortho)phosphate from test solutions, but pre-treating fiber with carboxymethyl cellulose followed by ferrous chloride treatment improved the phosphate-binding capacity (Eberhardt et al. Bioresource Technology 2006, 97:2371-2376).

U.S. Pat. No. 6,022,619 describes a method of forming textile composites comprising coatings of iron oxides deposited on textile substrates, a method for the deposition of iron(III) oxides in status nascendi from an aqueous solution so as to form a coherent coating on a textile substrate.

U.S. Publication 2009/0181592 describes a multicomponent fiber having a metal phobic component and a metal philic component that may be used in fabrics and other products manufactured therefrom for economically imparting at least one of an antistatic quality, antimicrobial and antifungal efficacy, and ultraviolet and/or electromagnetic radiation shielding.

U.S. Publication 2011/0086097 describes a manufacture process for producing an iron-containing phosphate adsorbent based on starch and soluble carbohydrates, in particular, a process for manufacturing and isolating an iron(III)-based phosphate adsorbent which purportedly exhibits pharmacological properties.

BRIEF SUMMARY

Provided herein are novel compositions that retain the beneficial characteristics of functional fiber components and at the same time change the nature of functional fiber components to compositions of matter that adsorb certain accessible targets in the gastrointestinal tract and in an extracorporeal system. In particular, metal ion compounds are attached to functional fiber components (also referred to herein after as fiber components) to alter or add further benefit to the nature of functional fiber components.

As such, provided herein are metal ion-functional fiber component complexes (also referred to herein after as metal ion fiber component complexes) such as iron-functional fiber component complex compositions having a high content of iron(II) and iron(III), magnesium-functional fiber component complex compositions, or compositions made of functional fiber component in a complex with metal ions such as zinc or lanthanum.

Exemplary functional fiber components include a single component or a mixture of two or more components selected from amylopectin, arabinoxylans, cellulose, carboxymethylcellulose, dextran, chitins, dextrins and resistant dextrins, gum Arabic, gum guar, inulin, lactulose, lignin, pectins, beta-glucans, starch, waxes, xylan, etc.

Gum Arabic, also known as *acacia* gum, chaar gund, char goond, or meska, is a natural gum made of hardened sap taken from two species of the *acacia* tree; Senegalia senegal and Vachellia seyal. The basic structural units of gum Arabic are galactose (~44%), rhamnose (~13%), arabinose (~27%), glucuronic acid and 4-O-methyl glucuronic acid (~16%) (Al-Assaf et al. Gum Arabic, Royal Society of Chemistry, 2012; Kapoor et al. Carbohyd Res 1991, 221:289-293). Gum Arabic from different species contains the same sugars in varying proportions (Glicksman and Sand, Gum Arabic in "Industrial Gums" (L. Whistler, editor), Academic press, 1973). The chemical structure of the gum has been widely studied revealing a multifractional material consisting mainly of a highly branched polysaccharide (Islam et al. Food Hydrocolloids 1997, 11:493-505). Gum Arabic is highly soluble in water, which is due to the high degree of branching and the small hydrodynamic volume (Williams et al. Food Hydrocolloids 1990, 4:305-311); it is stable over a wide range of pH from 3 to 9 (D'Angelo L L. Gums and Stabilisers for the Food Industry, Royal Society of Chemistry, 2010).

Exemplary metal ion compounds useful herein include, but are not limited to ions of metal compounds, such as lithium, sodium, potassium, rubidium, cesium, francium, beryllium, magnesium, calcium, strontium, barium, radium, scandium, yttrium, lanthanum, actinium, titanium, zirconium, hafnium, vanadium, niobium, tantalum, chromium, molybdenum, manganese, iron, cobalt, nickel, copper, zinc, aluminum, bismuth, etc.

Metal ion compounds useful herein include the different oxidation numbers of said metal ions as commonly known in chemistry. For example, iron compounds useful herein include both iron(II) and iron(III) salts including, but are not limited to iron(II) acetate, iron(II) citrate, iron(II) ascorbate, iron(II) oxalate, iron(II) oxide, iron(II) carbonate, iron(II) carbonate saccharate, iron(II) formate, iron(II) sulfate, iron (II) chloride, iron(III) chloride, iron(II) bromide, iron(II) iodide, iron(III) fluoride, iron(II) acetylacetonate, iron(III) phosphate, iron(III) pyrophosphate, and combinations thereof. Other examples include, but are not limited to salts of different metal ions similar to those of the iron compounds.

The metal ion-functional fiber component compositions according to the application are oligo- or polynuclear metal ion compositions in which the metal atoms are interacting with one another via oxygen atoms and/or hydroxyl groups, and wherein the metal ion is interacting with the functional fiber components in a complex and/or via carbon, oxygen, nitrogen, and/or hydrogen bridge bonds. The hydroxyl bridges also have a high binding affinity for metal ion(I), metal ion(II), metal ion(III), or metal ions which have an oxidation number of greater than III. The metal ion-functional fiber component compositions can also contain water bonded as a complex or via hydrogen bridge bonds.

The metal ion-functional fiber component compositions according to the application are characterized by their content of metal ion.

For example, the iron-functional fiber component compositions according to the application are characterized by their content of iron(II) and iron(III). This means that some of the iron is present in the oxidation state of $2^+$ and some in the oxidation state of $3^+$. These are therefore so-called "mixed valence" compositions, in which the metal ion is present in several oxidation states.

The content of metal ions in the compositions ranges from about 2 to about 50 wt. %. For example, in some embodiments with iron ions as the metal ions, the content of iron(II) and iron(III) in the total iron content is at least 2 wt. %. For example, the content of iron(II) and iron(III) in the total iron content can be 3 to 50 wt. %, or 3 to 25 wt. %, or 10 to 40 wt. %, or 15 to 30 wt. % or 20 to 50 wt %, or about 10 wt. %, or about 15 wt. %, or about 20 wt. %, or about 30 wt. %, or about 40 wt. %, or any other range or value within those ranges.

In some embodiments, the selected weight ratio of functional fiber components to metal ion compounds is from about 1:0.1 to about 1:100. For example, about 1:2, or about 1:3, or about 1:4, or about 1:5, or about 1:6, or about 1:7, or about 1:8, or about 1:9, or any other ratio or value. The content of functional fiber components by weight of the compositions is 10 to 98 wt. %, for example, for example, about 10 to 80 wt. %, about 50 to 90 wt. %, about 60 to 90 wt. %, about 70 to 85 wt. %, about 35 to 65 wt. %, about 40 to 60 wt. %, about 45 to 55 wt. %, or about 20 wt. %, or about 30 wt. %, or about 40 wt. %, or about 50 wt. % by weight, or any other range or value within those ranges.

The content of water in the metal ion-functional fiber component compositions can be up to 10 wt. %, depending on the drying conditions. Illustratively, the water content is about 2 to 8 wt. %, about 3 to 7 wt. %, about 2 to 5 wt. %, or about 5 to 10 wt. %, or any other range within those ranges.

In some embodiments, the metal ion-functional fiber component compositions comprise iron ions such as ferrous ($Fe^{2+}$) and/or ferric ($Fe^{3+}$) compounds and a functional fiber component in a complex or pharmaceutically acceptable salts thereof in a physiologically or pharmaceutically acceptable carrier. These compositions are useful for adsorbing undesirable agents including, but not limited to excess calcium, cholesterol, phosphate, potassium, sodium, as well as, toxins from infectious agents via in vivo, extracorporeal, ex vivo, or in vitro administration to a subject in need thereof.

Metal ions, which are present in the complex allow access to the analytes. In one embodiment, the metal ion-functional fiber component complex compositions comprise 2 to 50 wt. % of metal ions and 50 to 98 wt. % of one or more functional fiber components.

In one embodiment, the metal ion-functional fiber component complex compositions comprise 10 to 50 wt. % of metal ion and 50 to 90 wt. % of one or more functional fiber components.

In one embodiment, the metal ion-functional fiber component complex compositions comprise 10 to 40 wt. % of metal ion and 60 to 90 wt. % of one or more functional fiber components.

In one embodiment, the metal ion-functional fiber component complex compositions comprise 15 to 30 wt. % of metal ion and 70 to 85 wt. % of one or more functional fiber components.

In one embodiment the metal ion-functional fiber component complex has a density of 1.1 to 2.0 g/cm$^3$. In another embodiment the metal ion-functional fiber component complex has a density of 1.5 to 1.90 g/cm$^3$. In yet another embodiment the metal ion-functional fiber component complex has a density of >1.1 g/cm$^3$. For example, the iron-function fiber component complex has a density at 1.36 g/mL in a loose powder form (FIG. 5). By helium pycnometer, the density in a compressed form of the iron-gum Arabic composition is determined to be 1.95 g/mL The metal ion-functional fiber component complex is not soluble in water or ethanol or DMSO; and cannot be made so by adjusting the pH to acidic conditions. Thus, even at a pH below 2 the complex remains insoluble in water.

In one embodiment, the metal ion-functional fiber component complex composition is formulated as a medicament with an active pharmaceutical ingredient, a pharmaceutical composition comprising a compound or a pharmaceutically acceptable salt and a pharmaceutically acceptable carrier.

In another embodiment, the metal ion-functional fiber component complex composition is suitable for oral administration.

In one embodiment, a medicament or an elemental medical food suitable for mammals is provided comprising at least 10 mg of the metal ion-functional fiber component composition described herein. The medicament or medical food medical food can be in the form of a liquid solution; powder, bar, wafer, a suspension in an appropriate liquid or in a suitable emulsion, as detailed below. In some embodiments, the medicament or medical food may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents.

In another embodiment, a method for treating a patient suffering from abnormal mineral homeostasis with elevated calcium, phosphate, potassium, sodium in blood outside the normal range, comprising administering a therapeutically effective amount of the composition is provided.

In yet another embodiment, method for treating a patient suffering from hyperlipidemia, comprising administering a therapeutically effective amount of the composition is provided.

In another embodiment, a method for treating a patient suffering from toxins from infectious agents in the gastrointestinal tract comprising administering to a patient in need thereof a therapeutically effective amount of the composition is provided.

In another embodiment, a method for treating a patient suffering from abnormal metabolic parameters selected from glucose, insulin, GLP-1, glucagon, glycerol, triglycerides, cholesterol, NEFA and leptin levels, comprising administering an effective amount of the composition is provided.

In some aspects, the composition is administered in an amount of a total serving of at least 0.005 g/kg/day and up to about 50 g/kg/day of the medicament or elemental medical food to the patient daily.

In another aspect, a food supplement suitable for mammals comprising at least 10 mg of the metal ion-functional fiber component composition is provided. The food supplement can be in the form of a liquid solution, powder, bar, wafer, a suspension in an appropriate liquid or in a suitable emulsion, as detailed below. In some embodiments, the food supplement may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents.

In another embodiment, a method for treating or preventing a patient from abnormal mineral homeostasis with elevated calcium, phosphate, potassium, sodium in blood outside the normal range, and to maintain bone health comprising administering a therapeutically effective amount of the food supplement is provided.

In yet another embodiment, a method for maintaining bone health comprising administering to a subject an effective amount of the food supplement is provided.

In another embodiment, a method for maintaining a normal lipid profile and cardiovascular health comprising providing an effective amount of the food supplement to a subject is provided.

The disclosure provides a method for maintaining normal weight comprising providing an effective amount of the food supplement to a subject.

In a further embodiment, a method is provided for maintaining normal metabolic parameters such as glucose, insulin, GLP-1, glucagon, glycerol, triglycerides, cholesterol, NEFA and leptin levels, said method comprising providing an effective amount of the food supplement to a subject.

In certain embodiments, the food supplement is administered in an amount of at least 0.2 g per day and up to 1500 g per day of the food supplement to the subject daily.

In another embodiment, a method for preparing the disclosed compositions is provided. Generally, in one embodiment a metal ion salt, or a mixture of metal ion salts, is mixed together with a functional fiber component or a mixture of functional fiber components under acidic conditions at a pH in the range from about 1.0 to about 6.0 (for example, from about 1 to about 4, or from about 1 to about 3). To the mixture an alkali salt is added. The resulting solution is purified of excess debris, salts, impurities, etc., by any suitable method to produce a metal ion-functional fiber component complex with an elemental metal ion concentration between about 2% to about 50%.

In another embodiment, the selected weight ratio of functional fiber component to metal ion compounds is from about 1:0.1 to about 1:100. For example, about 1:0.2, or about 1:1, or about 1:5, or about 1:10, or about 1:20, or about 1:50, or about 1:80, or about 1:100, or any other ratio or value within these ranges.

In another embodiment, the acid used to achieve a pH in a range of about 1 to about 3 is selected from the group of hydrogen halides and their aqueous solutions including, but not limited to: hydrochloric acid (HCl), hydrobromic acid (HBr), hydroiodic acid (HI), halogen oxoacids such as hypochlorous acid (HClO), chlorous acid ($HClO_2$), chloric acid ($HClO_3$), perchloric acid ($HClO_4$), and corresponding compounds for bromine and iodine, sulfuric acid ($H_2SO_4$), fluorosulfuric acid ($HSO_3F$), nitric acid ($HNO_3$), phosphoric acid ($H_3PO_4$), fluoroantimonic acid ($HSbF_6$), fluoroboric acid ($HBF_4$), hexafluorophosphoric acid ($HPF_6$), chromic acid ($H_2CrO_4$), boric acid ($H_3BO_3$). Other acids are contemplated herein and are easily identifiable by one of skill in the art.

After functional fiber component(s) and metal ion compounds are mixed under acidic conditions, alkali salts can be optionally added to the functional fiber component/metal ion mixture to adjust the pH to be in the range of 1-6. In some aspects, the alkali salt is added to the functional fiber component/metal ion mixture to achieve a pH of the solution in a range of greater than about 3 to no greater than about 12. Alkali carbonates and alkali metal hydroxides are illustrative alkali substances or bases useful herein, though others are contemplated. The base can be selected from the group including, but not limited to LiOH, KOH, NaOH, $NaHCO_3$, $Na_2CO_3$, $Ca(OH)_2$, $Mg(OH)_2$, $Li_2CO_3$, $K_2CO_3$, $CaCO_3$, $MgCO_3$, and $Na_2CO_3$. The base can comprise any wt. % of the total weight of the metal ion-functional fiber component mixture, sufficient to alter the pH of the mixture to the desired range.

The temperature of the reaction mixture is in the range from about 20° C. to about 100° C., for example, about 30° C., about 40° C., about 50° C., about 60° C., about 70° C., about 80° C., about 90° C., or about 100° C. The time interval is in the range from about 30 minutes to about 48 hours (hr), for example, about 2 hr, about 3 hr, about 4 hr, about 6 hr, about 8 hr, about 12 hr, about 18 hr, about 24 hr, about 30 hr, about 36 hr, about 42 hr, or about 48 hr.

BRIEF DESCRIPTION OF THE DRAWINGS

FIG. 1 is a graph illustrating the physical appearance of the composition at each step during the process. Tube 1 (or Number 1): gum guar. Tube 2 (or Number 2): dextran. Tube 3 (or Number 3): amylopectin. Tube 4 (or Number 4): corn starch.

FIG. 27 is a graph illustrating a representative HPLC profile for the digoxin standard (A) vs. the digoxin sample treated with the iron-gum Arabic composition (B).

FIG. 28 is a graph illustrating the physical appearance of the composition at each step during the process. (FIG. 28A) Gum Arabic plus $MgCl_2$ in water at pH=2. (FIG. 28B) After addition of NaOH (pH=9). (C) The collected precipitate after drying.

DETAILED DESCRIPTION

Figure 1A:
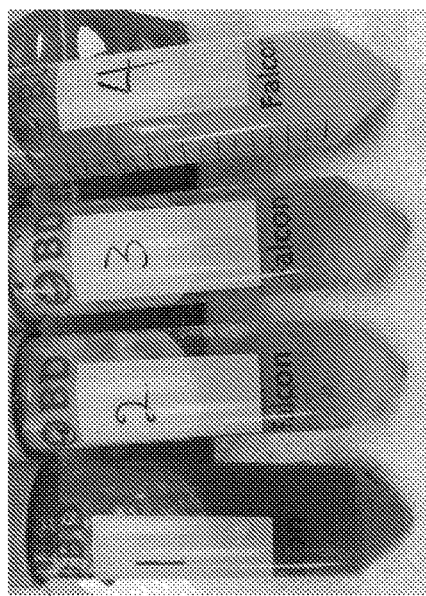
(FIG. 1A) The component in water.

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims. Thus, there are a variety of suitable formulations of the compositions described herein. These formulations are exemplary and are in no way limiting. Furthermore, one skilled in the art will appreciate that routes of administering the compositions and/or salts thereof include, but are not limited to, oral or alimentary administration. Although more than one route can be used, a particular route can provide a more immediate and more effective response than another route in a given situation.

One skilled in the art will recognize many methods and materials similar or equivalent to those described herein, which could be used in and are within the scope of the practice of the present invention. The present invention is in no way limited to the methods and materials described.

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

As used in this application, including the appended claims, the singular forms "a," "an," and "the" include plural references, unless the content clearly dictates otherwise, and are used interchangeably with "at least one" and "one or more." Thus, reference to "functional fiber components" includes mixtures of dietary fiber components, reference to "a metal ion complex" includes mixtures of metal ion complexes, and the like.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

Disclosed herein are metal ion compounds complexed to functional fiber components which alter or add further benefit to the nature of functional fiber components. As such, provided herein are metal ion-functional fiber component compositions having a high content of metal ion(I), metal ion(II), metal ion(III), and/or metal ion(Z) (M(Z)) (wherein M represents a metal ion and Z represents the oxidation number of the metal ion (positive charge) and M(Z) represents a metal having an oxidization level of Z). Exemplary functional fiber components include arabinoxylans, cellulose and carboxymethylcellulose, chitins, dextrins and resistant dextrins, glucans, gum Arabic, inulin, lactulose, lignin, pectins, starch, waxes, xylan, etc., and combinations thereof. The polymer complex can be amorphous, crystalline and contain microdomains of both amorphous and crystalline regions ranging from 10% to 90% amorphous and 10% to 90% crystalline. The location of the metal ion(I), metal ion(II) and/or metal ion(Z) can be in either the amorphous or crystalline regions or both.

As used herein "functional fiber components" (also referred to herein as "fiber components") include, but are not limited to a single component or a mixture of two or more components selected from—polysaccharides, such as amylopectin, arabinoxylans, cellulose, and many other dietary fiber components such as carboxymethylcellulose, dextran, chitins, dextrins and resistant dextrins, gum Arabic, gum guar, inulin, lactulose, lignin, pectins, beta-glucans, starch, waxes, xylan, etc. The functional fiber components may be naturally occurring, synthetic or a mixture thereof.

Exemplary metal ion compounds useful herein include, but are not limited to metals shown in the following table (lithium, sodium, potassium, rubidium, cesium, francium, beryllium, magnesium, calcium, strontium, barium, radium, scandium, yttrium, lanthanum, actinium, titanium, zirconium, hafnium, vanadium, niobium, tantalum, chromium, molybdenum, manganese, iron, cobalt, nickel, copper, zinc, aluminum, bismuth, etc.).

| Li | Be | | | | | | | | | | | | | | | |
|---|---|---|---|---|---|---|---|---|---|---|---|---|---|---|---|---|
| Na | Mg | | | | | | | | | | | Al | | | | |
| K | Ca | Sc | Ti | V | Cr | Mn | Fe | Co | Ni | Cu | Zn | Ga | | | | |
| Rb | Sr | Y | Zr | Nb | Mo | Tc | Ru | Rh | Pd | Ag | Cd | In | Sn | | | |
| Cs | Ba | La† | Hf | Ta | W | Re | Os | Ir | Pt | Au | Hg | Tl | Pb | Bi | Po | |
| Fr | Ra | Ac‡ | | | | | | | | | | | | | | |
| | | (La)† | Ce | Pr | Nd | Pm | Sm | Eu | Gd | Tb | Dy | Ho | Er | Tb | Yb | Lu |
| | | (Ac)‡ | Th | Pa | U | Np | Pu | Am | Cm | Bk | Cf | Es | Fm | Md | No | Lr |

Metal ion compounds useful herein include different oxidation numbers of the metal ions as well as different salt forms as commonly known in chemistry. For example, iron compounds useful herein include, but are not limited to iron(II) acetate, iron(II) citrate, iron(II) ascorbate, iron(II) oxalate, iron(II) oxide, iron(II) carbonate, iron(II) carbonate saccharate, iron(II) formate, iron(II) sulfate, iron(II) chloride, iron(III) chloride, iron(II) bromide, iron(II) iodide, iron(III) fluoride, iron(II) acetylacetonate, iron(III) phosphate, iron(III) pyrophosphate, and combinations thereof.

Exemplary magnesium compounds useful herein include, but are not limited to magnesium sulfate, magnesium hydroxide, magnesium chloride, magnesium oxide, magnesium gluconate, magnesium malate, magnesium orotate, magnesium glycinate, magnesium citrate, magnesium borate, magnesium salicylate, magnesium sulfate, magnesium bromide, magnesium stearate, magnesium carbonate, etc.

Exemplary calcium compounds useful herein include, but are not limited to calcium carbonate, calcium chloride, calcium gluconate, calcium stearate, calcium sulfate, etc.

Exemplary lanthanum compounds useful herein include, but are not limited to lanthanum oxide, lanthanum bromide, lanthanum chloride, lanthanum carbonate, lanthanum fluoride, etc.

Other examples include, but not limited to salts of different metal ions similar to those described above for the iron, magnesium, calcium and lanthanum compounds.

The metal ion-functional fiber component compositions or complexes according one embodiment are oligo- or polynuclear metal ion compositions in which the metal ion atoms are interacting with one another via oxygen atoms and/or hydroxyl groups, and wherein the metal ion is interacting with the functional fiber component as a complex and/or via carbon, nitrogen, and/or hydrogen bridge bonds. The hydroxyl bridges also have a high binding affinity for metal ion(I), metal ion(II) and/or metal ion(Z) (wherein (Z) represents the oxidation number or positive charge of the metal ion, indicated either by Roman numeral, i.e. Fe(II), or positive charge $Fe^{2+}$). The metal ion-functional fiber component compositions can also contain water bonded as a complex or via hydrogen bridge bonds.

The metal ion-functional fiber component compositions according to the invention are characterized by their content of metal ion(I), metal ion(II), metal ion(III), or metal ion with more than three electrical charges. This means that some of the metal ion is present in the oxidation level of $1^+$ or $2^+$ and some in the oxidation level of $3^+$ or more. These are therefore so-called "mixed valence" compounds, in which the metal ion is present in several oxidation levels side by side. The "oxidation state," or "oxidation number," is an indicator of the degree of oxidation of an atom in a chemical compound. Although they have slightly different meanings, for the most part it does not matter if the term oxidation state or oxidation number is used. Therefore as used herein these two terms are used interchangeably.

More specifically, oxidation state refers to the degree of oxidation of an atom in a molecule. Each atom of the molecule will have a distinct oxidation state for that molecule where the sum of all the oxidation states will equal the overall electrical charge of the molecule or ion. Each atom is assigned an oxidation state value based on predetermined rules based on electronegativity and periodic table groups.

Oxidation numbers, on the other hand are used in coordination complex chemistry. They refer to the charge the central atom would have if all ligands and electron pairs shared with the atom were removed. Thus, the oxidation number is the electrical charge that the central atom in a coordination compound would have if all the ligands and electron pairs were removed. Usually the oxidation number has the same value as the oxidation state.

As used herein, the oxidation number/state is represented by a Roman numeral. The plus sign is omitted for positive oxidation numbers. The oxidation number is seen as a superscript to the right of an element symbol (e.g., $Fe^{III}$) or in parentheses after the element name [e.g., Fe(III)] usually with no space between the element name and the parentheses. Also, as used herein the oxidation number is represented by a positive charge i.e. Fe (2+) or $Fe^{+2}$ and the like.

In some embodiments, the content of metal ion(I), metal ion(II) and/or metal ion(Z) (wherein Z represents the oxidation number of the metal ion) in the total metal ion content of the metal ion-functional fiber component composition is at least 2 wt. %. For example, the content of metal ion(I), metal ion(II) and/or metal ion(Z) (wherein Z represents the oxidation number of the metal ion) in the total metal ion content can be 2 to 50 wt. %, or 3 to 50 wt. % or 3 to 25 wt. %, or 20 to 50 wt. %, or 10 to 50 wt %, or 10 to 40 wt. % or 15 to 30 wt %, or about 10%, or about 20%, or about 30%, or about 40%, or any other range or value within those ranges.

For example, in some embodiments with iron ions as the metal ion, the content of iron(II) and iron(III) in the total iron content of the iron-functional fiber component composition is at least 2 wt. %. For example, the content of iron(II) and iron(III) in the total iron content can be 2 to 50 wt. %, or 3 to 50 wt. % or 3 to 25 wt. %, or 20 to 50 wt. %, or 10 to 50 wt %, or 10 to 40 wt. % or 15 to 30 wt %, or about 10%, or about 20%, or about 30%, or about 40%, or any other range or value within those ranges.

In some embodiments, the selected weight ratio of functional fiber component to metal ion compounds is from about 1:1 to about 1:10. For example, about 1:2, or about 1:3, or about 1:4, or about 1:5, or about 1:6, or about 1:7, or about 1:8, or about 1:9, or any other ratio or value. The content of functional fiber component by weight of the composition is 10 to 98 wt. %, for example, about 10 to 80 wt. %, about 50 to 90 wt %, about 60 to 90 wt %, about 70 to 85 wt %, about 35 to 65 wt. %, about 40 to 60 wt. %, about 45 to 55 wt. %, or about 20%, or about 30%, or about 40%, or about 50% by weight, or any other range or value within those ranges. The metal ion(I), metal ion(II), and/or metal ion(III) are on the surface of the functional fiber component and in the bulk functional fiber component; the selected weight ratio of surface vs. bulk metal ion content can be 10 to 90 wt. % or 90 to 10 wt. % and in between. The action of the metal ion-functional fiber component composition is not affected by the metal ion at one location compared to another.

The content of water in the metal ion-functional fiber component compositions can be up to 10 wt. %, depending on the drying conditions. Illustratively, the water content is about 2 to 8 wt. %, about 3 to 7 wt. %, about 2 to 5 wt. %, or about 5 to 10 wt. %, or any other range within those ranges.

In some embodiments, the metal ion-functional fiber component compositions comprise metal ion(I), metal ion (II) and/or metal ion(Z) (wherein Z represents the oxidation number of the metal ion) compounds and a mixture of functional fiber components in a complex or pharmaceutically acceptable salts thereof in a physiologically or pharmaceutically acceptable carrier. The compositions that make up a therapeutic formulation can be mixtures of non-metal ion containing functional fiber component and metal ion-containing functional fiber component. The amount of metal ion-containing functional fiber component is from 1 to 100 wt. % depending on the application. These compositions are useful for adsorbing undesirable agents including, but not limited to excess calcium, cholesterol, phosphate, potassium, sodium, as well as, toxins from infectious agents via in vivo, extracorporeal, ex vivo, or in vitro administration to a subject in need thereof. Said metal ion-functional fiber component compositions comprise at least 2 wt. % of metal ion (I/II/III) with 3 to 50 wt. % of metal ion (I/II/III), 10 to 80 wt. % of functional fiber component. In some aspects, said compositions further having been treated under alkaline conditions.

For example, in some embodiments, iron ion is the metal ion in the composition. The iron-functional fiber component compositions comprise ferrous ($Fe^{2+}$) and/or ferric ($Fe^{3+}$) compounds and a functional fiber component in a complex or pharmaceutically acceptable salts thereof in a physiologically or pharmaceutically acceptable carrier. The compositions that make up a therapeutic formulation can be mixtures of non-iron containing functional fiber component and iron (II) and iron(III)-containing functional fiber component. The amount of iron-containing functional fiber component is from 1 to 100 wt. % depending on the application. These compositions are useful for adsorbing undesirable agents including, but not limited to excess calcium, cholesterol, phosphate, potassium, sodium, as well as, toxins from infectious agents via in vivo, extracorporeal, ex vivo, or in vitro administration to a subject in need thereof. Said iron-functional fiber component compositions comprise at least 2 wt. % of iron(II/III) with 3 to 50 wt. % of iron(II/III), 10 to 80 wt. % of functional fiber component. In some aspects, said compositions further having been treated under alkaline conditions.

As used herein the term "minimal metal ion release" refers to less than 5% by wt. of metal ion release from compositions comprising metal ion-functional fiber component complex or a salt thereof under physiological condition.

For example, as used herein the term "minimal iron release" refers to less than 5% by wt. of iron release from compositions comprising iron-functional fiber component complex or a salt thereof under physiological condition.

For another example, as used herein the term "minimal magnesium release" refers to less than 5% by wt. of magnesium release from compositions comprising magnesium functional fiber component complex or a salt thereof under physiological condition.

The invention also provides a pharmaceutical composition comprising the metal ion-functional fiber component complex composition formulated as a medicament with an active pharmaceutical ingredient, a pharmaceutical composition comprising a compound or a pharmaceutically acceptable salt and a pharmaceutically acceptable carrier.

The carrier can be any of those conventionally used and is limited only by physico-chemical considerations, such as solubility and lack of reactivity with the active compound(s), and by the route of administration. It will be appreciated by one of skill in the art that, in addition to the following described pharmaceutical composition, the compounds of the present inventive methods can be formulated as inclusion complexes, such as cyclodextrin inclusion complexes, or liposomes.

The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular compound or salt thereof of the invention and other active agents or drugs used, as well as by the particular method used to administer the compound. Accordingly, there are a variety of suitable formulations of the pharmaceutical composition of the present inventive methods. The following formulations for oral, nasal, parenteral, subcutaneous, intrathecal, intravenous, intramuscular, interperitoneal, rectal, transdermal, sublingual, internasal, intranasal, ocular, and vaginal administration are exemplary and are in no way limiting. One skilled in the art will appreciate that these routes of administering the compound or salt thereof of the invention are known, and, although more than one route can be used to administer a particular compound, a particular route can provide a more immediate and more effective response than another route.

In one embodiment, a medicament or medical food suitable for mammals is provided comprising at least 10 mg of the metal ion-functional fiber component composition described herein. The medicament or medical food can be in the form of a liquid solution; powder, bar, wafer, a suspension in an appropriate liquid or in a suitable emulsion, as detailed below. In some embodiments, the medicament or medical food may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents.

As used herein the terms "medicament" or "pharmaceutical composition" encompass a substance or preparation used to treat disease or medical condition.

As used herein the term "medical food," as defined in section 5(b) of the Orphan Drug Act (21 U.S.C. 360ee (b)(3)) is "a food which is formulated to be consumed or administered enterally under the supervision of a physician and which is intended for the specific dietary management of a disease or condition for which distinctive nutritional requirements, based on recognized scientific principles, are established by medical evaluation."

Formulations suitable for oral administration are described herein for purposes of illustration. Oral formulations can include of (a) liquid solutions, such as an effective amount of the composition thereof dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; (e) nano or micro particles; and (f) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, *acacia*, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and *acacia* or tragacanth, as well as pastilles comprising the active ingredient in an inert base, such as gelatin and glycerin, or sucrose and *acacia*, emulsions, gels, and the like containing, in addition to the active ingredient, such excipients as are known in the art.

The composition can be consumed at any time during the day, e.g. as a meal, before, during, or after a meal, etc. Ultimately, the attending physician shall decide the optimal time for dosing.

The compositions of the invention described herein can be administered to an extracorporeal system to adsorb certain accessible targets in the extracorporeal system in vitro. Furthermore, the compositions of the invention can be administered to a subject in vivo or ex vivo.

The compositions of the invention can be administered to a cell, for example, to a cell of a subject. Subjects include, for example, bacteria, yeast, fungi, plants, and mammals. In some embodiments, the subject is a mammal. Mammals include, but are not limited to, the order Rodentia, such as mice, and the order Logomorpha, such as rabbits, the order Carnivora, including Felines (cats) and Canines (dogs), the order Artiodactyla, including Bovines (cows) and Swines (pigs), the order Perssodactyla, including Equines (horses), the order Primates, Ceboids, or Simioids (monkeys), the order Anthropoids (humans and apes). Illustratively the mammal is the human. Furthermore, the subject can be the unborn offspring of any of the forgoing subjects, including mammals (e.g., humans), in which case any screening of the subject or cells of the subject, or administration of compositions to the subject or cells of the subject, can be performed in utero.

The amount or dose of a composition should be sufficient to affect a therapeutic or prophylactic response in the subject over a reasonable time frame. The appropriate dose will depend upon the nature and severity of the disease or affliction to be treated or prevented, as well as by other factors. For instance, the dose also will be determined by the existence, nature and extent of any adverse side effects that might accompany the administration of the particular composition. Ultimately, the attending physician will decide the dosage of the composition of the present invention with which to treat each individual patient, taking into consideration a variety of factors, such as age, body weight, general health, diet, sex, composition to be administered, route of administration, and the severity of the condition being treated. An exemplary dose of a composition is the maximum that a patient can tolerate without incurring serious side effects. Typical doses might be, for example, about 0.005 g/kg/day to about 50 g/kg/day.

The compositions can be used for any purpose including, without limitation, the treatment, prevention, or diagnosis of a disease or condition, the screening of compounds that can be used to treat, prevent, or diagnose a disease or condition, or the research of the underlying mechanisms or causes of a disease or condition, which research can be used, for example, in the development of methods to treat, prevent, or diagnose the disease or condition. Without wishing to be bound by any particular theory, it is believed that the compositions of the invention are particularly useful with respect to diseases and conditions involving the adsorption of certain accessible targets in gastrointestinal tract or in the extracorporeal system.

"Diagnose", "diagnosing", "diagnosis", and variations thereof refer to the detection, determination, or recognition of a health status or condition of an individual based on one or more signs, symptoms, data, or other information pertaining to that individual. The health status of an individual can be diagnosed as healthy/normal (i.e., a diagnosis of the absence of a disease or condition) or diagnosed as ill/abnormal (i.e., a diagnosis of the presence, or an assessment of the characteristics, of a disease or condition). The terms "diagnose", "diagnosing", "diagnosis", etc., encompass, with respect to a particular disease or condition, the initial detection of the disease; the characterization or classification of the disease; the detection of the progression, remission, or recurrence or reactivation of the disease; and the detection of disease response after the administration of a treatment or therapy to the individual. The diagnosis of a disease or condition includes distinguishing individuals who have said disease or condition from individuals who do not.

"Prognose", "prognosing", "prognosis", and variations thereof refer to the prediction of a future course of a disease or condition in an individual who has the disease or condition (e.g., predicting patient survival), and such terms encompass the evaluation of disease response to the administration of a treatment or therapy to the individual. "Prognosing" and variants thereof can also mean predicting evidence of disease (EVD) or no evidence of disease (NED) in the individual at a future preselected time point. The date of prognosing can be referred to as time point 1 (TP1), and the preselected future time point may be referred to as time point 2 (TP2) and can include a specific future date or range of dates, for example post-treatment follow-up.

"Evaluate", "evaluating", "evaluation", and variations thereof encompass "diagnosing," "treating," "prognosing" and monitoring of recurrence in a treated individual. "Evaluating" can include any of the following: 1) diagnosing, i.e., initially detecting the presence or absence of a disease or condition; 2) prognosing at time point 1 (TP1), the future outcome of treatment at time point 2 (TP2), i.e., where TP2 may follow therapy; 3) detecting or monitoring disease progression or recurrence after apparent cure of said disease or condition i.e., wherein "monitoring after apparent cure" means testing an individual a time point after he or she has received successful treatment, and/or 4) detecting progression from latent infection to active disease.

"Treatment," as used herein refers to an intervention performed with the intention of preventing the development or altering the pathology of a disorder. Accordingly, "treatment" refers to both therapeutic and prophylactic or preventative measures. Those in need of treatment include those already with the disorder as well as those in which the disorder is to be prevented.

"Therapy" as used herein refers to an intervention performed with the intention of preventing the development or altering the pathology of a disorder. "Therapy" refers to various methods that target particular diseases with particular disease fighting agents. For example, a targeted therapy might involve providing to a subject in need thereof the metal ion-functional fiber component composition in a physiologically acceptable carrier for adsorbing undesirable agents including, but not limited to excessive amounts of calcium, cholesterol, phosphate, potassium, sodium, as well as, toxins from infectious agents via in vivo, extracorporeal, ex vivo, or in vitro administration As used utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

As used herein, the term "physiologically acceptable carrier" refers to any carrier or excipient commonly used with pharmaceuticals. Such carriers or excipients include, but are not limited to, oils, starch, sucrose and lactose.

A "pharmaceutically acceptable salt" or "salt" of a metal ion-functional fiber component composition is a product of the disclosed composition that contains an ionic bond, and is typically produced by reacting the disclosed compositions with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising the disclosed compositions in a form suitable for administration to a subject. A pharmaceutical composition of the invention is preferably formulated to be compatible with its intended route of administration.

As used herein the term "therapeutically effective amount" generally means the amount necessary to ameliorate at least one symptom of a disorder to be prevented, reduced, or treated as described herein. The phrase "therapeutically effective amount" as it relates to the compositions described herein shall mean the dosage that provides the specific pharmacological response for which the composition is administered in a significant number of subjects in need of such treatment. It is emphasized that a therapeutically effective amount that is administered to a particular subject in a particular instance will not always be effective in treating the conditions/diseases described herein, even though such dosage is deemed to be a therapeutically effective amount by those of skill in the art.

Thus, in one aspect a method of treating a disease that benefits from adsorption of certain accessible targets in gastrointestinal tract or in an extracorporeal system is provided. The method comprises administering to a patient in need thereof a therapeutically effective amount of the composition of the instant disclosure. The foregoing method is suitable for use in a subject or patient that is afflicted with a disease or at risk for developing a disease, such as a disease that benefits from adsorption of certain accessible targets in gastrointestinal tract or in an extracorporeal system. Such diseases include, for example, a bone disorder, cardiovascular disease, a cardiovascular complication associated with renal disease, endothelial dysfunction, hyperparathyroidism, hypercalcemia, hyperphosphatemia, an immune disorder, left ventricular hypertrophy, a proliferative disease, proteinuria, renal disease, viral infection, bacterial infection, musculoskeletal disorders, high blood pressure, hypertriglyceridemia, lipid disorders, hyperlipoproteinemia, hyperlipidemia, dyslipidemia, diabetes, hypercholesterolemia, multiple sclerosis, myelodysplastic syndrome, proximal myopathy, premature aging, metabolic syndrome, insulin resistance, obesity. One or more symptoms of the disease is prevented, reduced, or eliminated subsequent to administration of the composition, thereby effectively treating or preventing the disease to at least some degree.

The patient or subject can be any animal, domestic, livestock or wild, including, but not limited to cats, dogs, horses, pigs and cattle, and preferably human patients. As used herein, the terms patient and subject may be used interchangeably.

In another aspect a method for preparing the disclosed compositions is provided. Generally, in one embodiment a metal ion salt, or a mixture of metal ion salts, is mixed together with a functional fiber component under acidic conditions at a pH in the range from about 1.0 to about 6.0 (e.g. from about 1 to about 4, or from about 1 to about 3). To the mixture an alkali salt is added. The resulting material is purified of excess debris, salts, impurities, etc., by any suitable method to produce a metal ion-functional fiber component complex with an elemental metal ion concentration between about 2% to about 50%.

In another aspect, a metal ion-functional fiber component complex is prepared by a process comprising the steps of: (a) mixing one or more functional fiber components and a metal ion compound, at a pH <7; (b) maintaining a temperature of reaction mixture of step (a) between ambient and 100° C.; (c) cooling the reaction mixture of step (b) to ambient temperature; (d) adjusting the pH using base until precipitates are formed; (e) washing until pH is neutral; and (f) isolating the metal ion-functional fiber component complex formed, wherein the metal ion content is in an amount of from 2 to 50 wt %.

The acid used to achieve a pH in a range of about 1 to about 6 are selected from the group of hydrogen halides and their solutions including, but not limited to: hydrochloric acid (HCl), hydrobromic acid (HBr), hydroiodic acid (HI), halogen oxoacids such as hypochlorous acid (HClO), chlorous acid ($HClO_2$), chloric acid ($HClO_3$), perchloric acid ($HClO_4$), and corresponding compounds for bromine and iodine, sulfuric acid ($H_2SO_4$), fluorosulfuric acid ($HSO_3F$), nitric acid ($HNO_3$), phosphoric acid ($H_3PO_4$), fluoroantimonic acid ($HSbF_6$), fluoroboric acid ($HBF_4$), hexafluorophosphoric acid ($HPF_6$), chromic acid ($H_2CrO_4$), boric acid ($H_3BO_3$). Other acids are contemplated herein and are easily identifiable by one skilled in the art.

After functional fiber component and metal ion compounds are mixed under acidic conditions, alkali salts can be added to the functional fiber component/metal ion mixture to adjust the pH to be between 1 and 6. In various embodiments, the pH is adjusted to be in the range of greater than about 3 and less than about 12. Alkali carbonates and alkali metal hydroxides are illustrative alkali substances useful herein, though others are contemplated. The base can be selected from the group including, but not limited to LiOH, KOH, NaOH, $NaHCO_3$, $Na_2CO_3$, $Ca(OH)_2$, $Mg(OH)_2$, $Li_2CO_3$, $K_2CO_3$, $CaCO_3$, $MgCO_3$, and $Na_2CO_3$. The base can comprise any wt. % of the total weight of the metal ion-functional fiber component mixture, sufficient to alter the pH of the mixture.

The temperature of the reaction mixture is in the range from about 20° C. to about 100° C., for example, about 30° C., about 40° C., about 50° C., about 60° C., about 70° C., about 80° C., about 90° C., or about 100° C. The time interval is in the range from about 30 minutes to about 48 hr, for example, about 2 hr, about 3 hr, about 4 hr, about 6 hr, about 8 hr, about 12 hr, about 18 hr, about 24 hr, about 30 hr, about 36 hr, about 42 hr, or about 48 hr.

The following examples are provided for illustrative purposes only and are not intended to limit the scope of the application as defined by the appended claims. All examples described herein were carried out using standard techniques, which are well known and routine to those of skill in the art.

EXAMPLES

Example 1

Mixed 1 gram (g) gum guar (Sigma G4129), or 1 g dextran (Sigma 31392), or 1 g amylopectin (Sigma A8515), or 1 g corn starch (Sigma S4180) into 27.5 ml of water. Pre-heated at 60° C.

Prepared an aqueous solution of $FeCl_3$ ($FeCl_3.6\ H_2O$, Sigma F2877) in water at 0.37 g/ml, at a pH in the range of 1-2.

Added 2 ml of $FeCl_3$ (0.37 g/ml in water) into the fiber component mixture. Added water to the final volume of 30 ml (pH at 1-2). Allowed the mixture to shake in a shaker at 60° C. for 1 hour (hr).

FIG. 1A shows the appearance of the component in water before addition of $FeCl_3$. Gum guar absorbed water and became gel-like, almost solid and difficult to mix. Dextran and amylopectin were soluble in water. Corn starch formed a suspension.

Figure 1B:
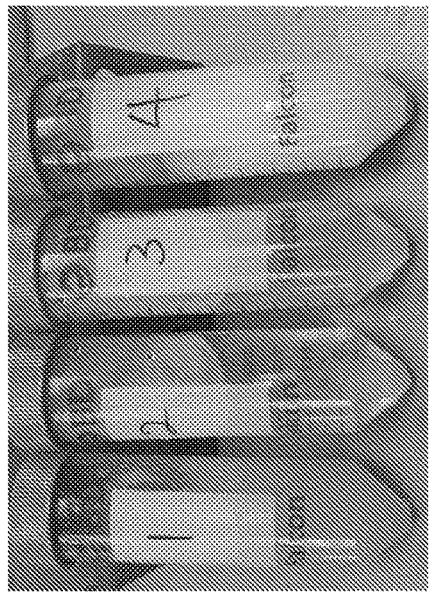
(FIG. 1B) after addition of $FeCl_3$ plus 1 hour of incubation.

FIG. 1B shows the appearance of the component after addition of $FeCl_3$ plus 1 hr of incubation at 60° C. Except a change in color, the status of each component (gel-like, soluble and suspension) remained the same. It was not possible to mix the gum guar preparation well.

Cooled the mixture to be <30° C. Added NaOH until pH was ~7.

Figure 1C:
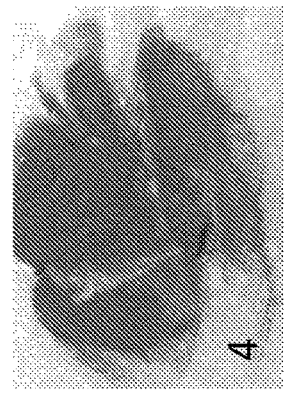
(FIG. 1C) The filtered material after wash.

After addition of NaOH, precipitates formed in each tube. Tube 1 (gum agar) already appeared as a gel-like material before adding NaOH. The amount of precipitate varied. FIG. 1C shows the appearance of the filtered material after wash; very little precipitate was recovered in the dextran or amylopectin preparation.

Washed the precipitated material with water by filtration until the filtrate was clear. Again, Tube 1 (gum agar) was difficult to handle and might not be washed adequately.

Dried the material using a food dehydrator for 24 hr. Less than 0.1 g was recovered from dextran; less than 0.5 g was recovered from amylopectin; 1+ g was recovered from gum guar or corn starch.

Ground the material using a nut grinder.

With 0.1 gram of the dried composition from gum guar, amylopectin and corn starch, added 5 ml of a 20 mM phosphate solution (1.37 ml of 85% phosphoric acid, 3.18 g of sodium carbonate and 4.68 g of NaCl in 1 liter of water, pH=7.0) to each sample and incubated at room temperature for 3 and 24 hr. Centrifuged and collected the supernatant. The dextran preparation was not tested because there was not enough material.

Determined the phosphate level in the supernatants using the phosphate colorimetric assay (Catalog #K410-500 from BioVision). Calculated the phosphate bound and normalized the amount of phosphate bound by the quantity of the composition used (i.e. 0.1 g).

TABLE 1

Summary of the phosphate binding ability of the compositions

| Composition | Phosphate bound at 3 hr | Phosphate bound at 24 hr |
|---|---|---|
| Gum guar* | 0.80 mmol per g of dry composition | 0.76 mmol per g of dry composition |
| Amylopectin | 0.19 mmol per g of dry composition | 0.38 mmol per g of dry composition |
| Corn Starch | 0.12 mmol per g of dry composition | 0.12 mmol per g of dry composition |

*The result for the gum guar preparation may not be accurate due to the difficulty in preparing the sample.

Figure 2:
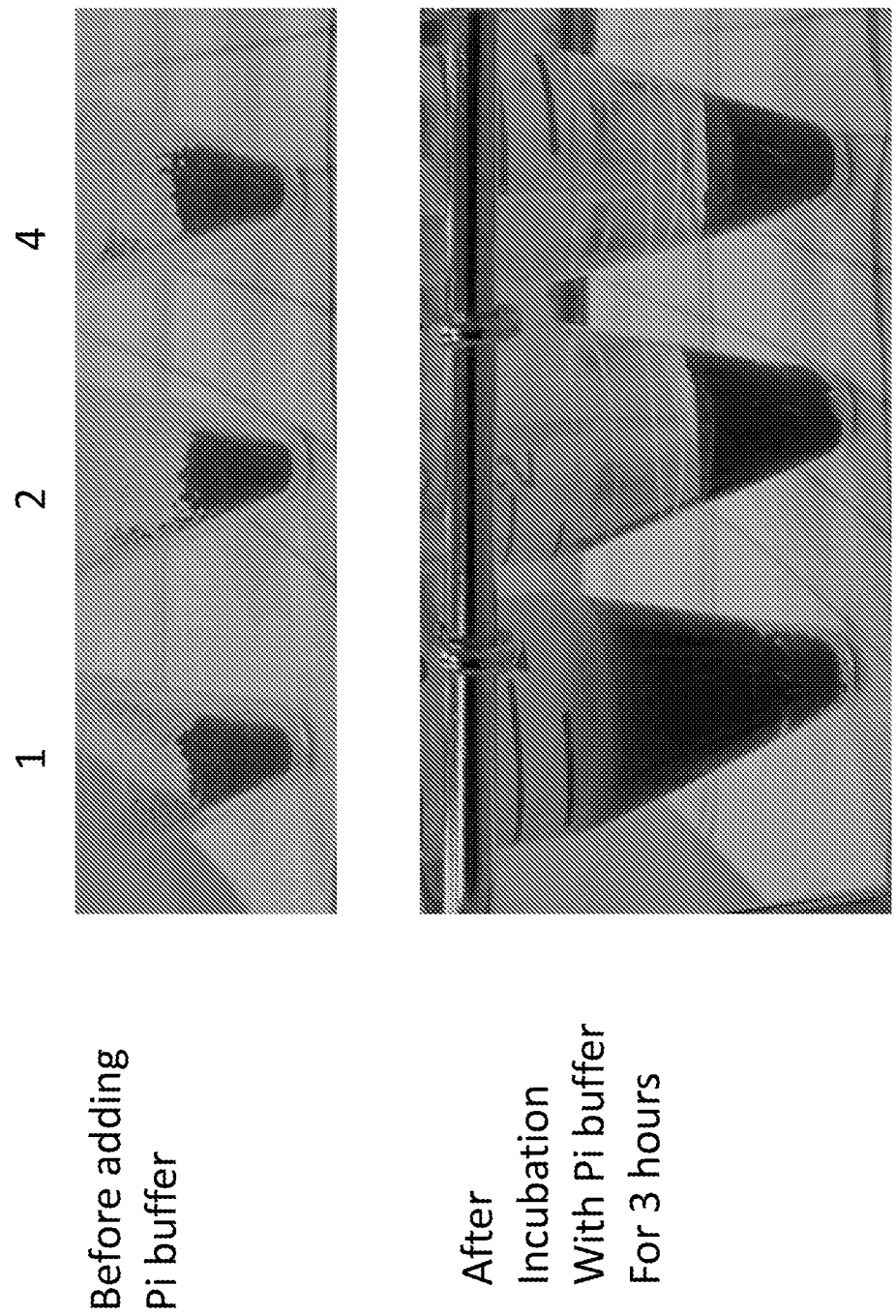
FIG. 2 illustrates the physical appearance of the composition at 0.1 gram in the dry state and after the incubation with the phosphate buffer for 3 hr. Tube 1: gum guar. Tube 3: amylopectin. Tube 4: corn starch.

FIG. 2 shows the physical appearance of the compositions at 0.1 gram in the dry state and after the incubation with the phosphate buffer for 3 hr. The swell volume of the compositions at 3 hr after exposure to the phosphate buffer was: 1.3 ml for gum guar, 0.3 ml for amylopectin and 0.25 ml for corn starch.

Example 2

Mixed 1 g xylan (Sigma x4252), or 1 g dextrin (Roquette 338111 W Nutriose FM06), or 1 g inulin (Sigma 370959) into 15 ml of water. Pre-heated at 60° C. Xylan formed a suspension; dextrin and inulin were soluble in water.

Added 2 ml of $FeCl_3$ (0.37 g/ml in water) into the fiber component mixture. Added water to the final volume of 20 ml (pH at 1-2). Allowed the mixture to shake in a shaker at 60° C. for 1 hr.

Cooled the mixture to be <30° C. Added NaOH until pH was between 7 and 8.

After addition of NaOH, precipitates formed in each tube. However, the amount of precipitate varied. Very little precipitate was recovered in the dextrin or inulin preparation.

Washed the precipitated material with water by filtration until the filtrate was clear.

Dried the material using a food dehydrator for 24 hr. Less than 0.1 g was recovered from inulin; less than 0.5 g was recovered from dextrin; 1+ g was recovered from xylan.

Ground the material using a nut grinder.

With 0.1 gram of the dried composition from xylan and dextrin, added 5 ml of a 20 mM phosphate solution (as described in Example 1) to each sample and incubated at room temperature for 3 hr. Centrifuged and collected the supernatant. The inulin preparation was not tested because there was not enough material.

Determined the phosphate level in the supernatants using the phosphate colorimetric assay (Catalog #K410-500 from BioVision).

TABLE 2

Summary of the phosphate binding ability of the compositions

| Composition | Phosphate bound at 3 hr |
|---|---|
| Xylan | 0.14 mmol per g of dry composition |
| Dextrin | 0.04 mmol per g of dry composition |

The swell volume of the compositions at 3 hr after exposure to the phosphate buffer was: 0.3 ml for xylan and 0.12 ml for dextrin.

Example 3

Mixed 1 g dietary fiber (e.g. Ultimate Fiber from Nature's Secret), or 1 g gum Arabic (Sigma G9752 or Sigma 30888), or 1 g pectin (Sigma 76282) into 27.5 ml of water. Pre-heat at 60° C. The dietary fiber formed a suspension; gum Arabic was soluble; pectin was gel-like, almost solid and difficult to mix.

Added 1 ml of $FeCl_3$ (0.37 g/ml in water) into the fiber or fiber component mixture. Added water to the final volume of 30 ml (pH at 1-2). Allowed the mixture to shake in a shaker at 60° C. for 1 hr. It was not possible to mix the pectin preparation well.

Cooled the mixture to be <30° C. Added NaOH until pH was between 8 and 10. Precipitates formed in each tube. Tube 3 (pectin) already appeared as a gel-like material before adding NaOH.

Washed the precipitated material with water by filtration until the filtrate was clear. Again, Tube 3 (pectin) was difficult to handle and might not be washed adequately.

Dried the material using a food dehydrator for 24 hr. Ground the material using a nut grinder.

With 0.1 gram of the dried composition, added 5 ml of a 20 mM phosphate solution (as in Example 1) to each sample and incubated at room temperature for 24 hr. Centrifuged and collected the supernatant.

Determined the phosphate level in the supernatants using the phosphate colorimetric assay (Catalog #K410-500 from BioVision). Normalized the amount of phosphate bound by the quantity of the composition used (i.e. 0.1 g).

TABLE 3

Summary of the phosphate binding ability of the compositions

| Composition | Phosphate bound at 24 hr |
|---|---|
| Dietary fiber | 0.17 mmol per g of dry composition |
| Gum Arabic | 0.43 mmol per g of dry composition |
| Pectin* | 0.28 mmol per g of dry composition |

*The result for the pectin preparation may not be accurate due to the difficulty in preparing the sample.

Example 4

Mixed 1 g cellulose (Sigma C6288), or 1 g lignin (Sigma 370959), or 0.8 g of gum Arabic plus 0.2 g of lignin, or 0.5 g of gum Arabic plus 0.5 g of lignin, or 0.5 g of gum Arabic plus 0.4 g of lignin plus 0.1 g of cellulose into 27.5 ml of water. Pre-heated at 60° C. All samples formed a suspension.

Added 1 ml of $FeCl_3$ (0.37 g/ml in water) into the fiber component mixture. Added water to the final volume of 30 ml (pH at 1-2). Allowed the mixture to shake in a shaker at 60° C. for 1 hr.

Cooled the mixture to be <30° C. Added NaOH until pH was between 6 and 7. In addition to the particles in suspension, more precipitates formed in each tube.

Washed the precipitated material with water by filtration until the filtrate was clear.

Dried the material using a food dehydrator for 24 hr. Ground the material using a nut grinder.

With 0.1 gram of the dried composition, added 5 ml of a 20 mM phosphate solution (as in Example 1) to each sample and incubated at room temperature for 3 and 24 hr. Centrifuged and collected the supernatant.

Determined the phosphate level in the supernatants using the phosphate colorimetric assay (Catalog #K410-500 from BioVision). Normalized the amount of phosphate bound by the quantity of the composition used (i.e. 0.1 g).

TABLE 4

Summary of the phosphate binding ability of the compositions

| Composition | Phosphate bound at 3 hr | Phosphate bound at 24 hr |
|---|---|---|
| Cellulose | 0 mmol per g of dry composition | 0.14 mmol per g of dry composition |
| Lignin | 0 mmol per g of dry composition | 0 mmol per g of dry composition |
| Gum Arabic + lignin at 4:1 | 0.17 mmol per g of dry composition | 0.21 mmol per g of dry composition |
| Gum Arabic + lignin at 1:1 | 0.06 mmol per g of dry composition | 0.07 mmol per g of dry composition |
| Gum Arabic + lignin + cellulose at 5:4:1 | 0.03 mmol per g of dry composition | 0.05 mmol per g of dry composition |

Example 5

Mixed 1 g gum Arabic plus 0.1 g of cellulose, or 1 g gum Arabic plus 0.1 g of cellulose and 0.1 g dextrin into 15 ml of water. Pre-heated at 60° C.

Added 2 ml of $FeCl_3$ (0.37 g/ml in water) into the fiber component mixture. Added water to the final volume of 20 ml (pH at 1-2). Allowed the mixture to shake in a shaker at 60° C. for 1 hr.

Cooled the mixture to be <30° C. Added NaOH until pH was ~7.

Washed the precipitated material with water by filtration until the filtrate was clear.

Dried the material using a food dehydrator for 24 hr. Ground the material using a nut grinder.

With 0.1 gram of the dried composition, added 5 ml of a 20 mM phosphate solution (as in Example 1) to each sample and incubated at room temperature for 24 hr. Centrifuged and collected the supernatant.

Determined the phosphate level in the supernatants using the phosphate colorimetric assay (Catalog #K410-500 from BioVision). Normalized the amount of phosphate bound by the quantity of the composition used (i.e. 0.1 g).

TABLE 5

Summary of the phosphate binding of the compositions

| Composition | Phosphate bound at 24 hr |
|---|---|
| Gum Arabic + cellulose | 0.49 mmol per g of dry composition |
| Gum Arabic + cellulose + dextrin | 0.48 mmol per g of dry composition |

Example 6

Mixed 1 g gum Arabic into 15 ml of water. Pre-heated at 60° C.

Added 0, 0.4, 1, 2, 4 ml of $FeCl_3$ (0.37 g/ml in water) into the fiber component mixture. Added water to the final volume of 20 ml (pH ranging from 1 to 2 with $FeCl_3$ and pH=4 without $FeCl_3$). Allowed the mixture to shake in a shaker at 60° C. for 1 hr.

Cooled the mixture to be <30° C. Added NaOH until pH was between 6 and 7.

No precipitate was formed in Tube 1 without the addition of $FeCl_3$. Washed the precipitated materials in the other tubes with water by filtration until the filtrate was clear.

Dried the material using a food dehydrator for 24 hr. Ground the material using a nut grinder.

With 0.1 gram of the dried composition, added 5 ml of a 20 mM phosphate solution (as in Example 1) to each sample and incubated at room temperature for 24 hr. Centrifuged and collected the supernatant.

Determined the phosphate level in the supernatants using the phosphate colorimetric assay (Catalog #K410-500 from BioVision). Normalized the amount of phosphate bound by the quantity of the composition used (i.e. 0.1 g)

Figure 3A:
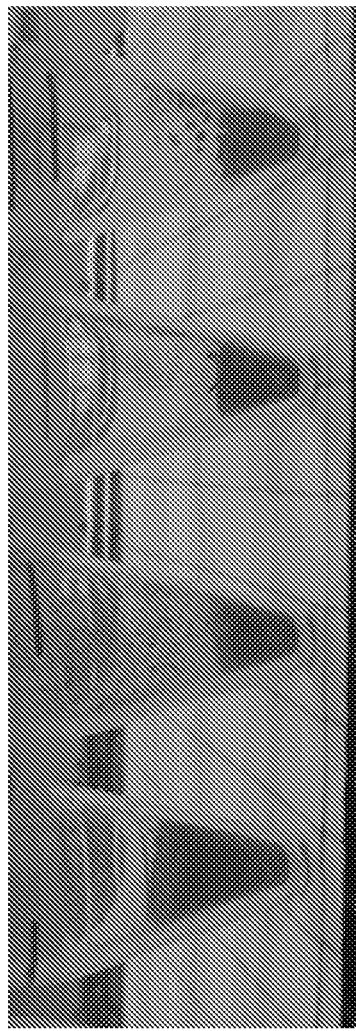
FIG. 3 is a graph illustrating the physical appearance of the dried composition at 0.1 g per sample (FIG. 3A), and the appearance of the composition after incubating with the phosphate buffer for 3 hour at room temperature (FIG. 3B). Tube 2: 0.4 ml of $FeCl_3$. Tube 3: 1 ml of $FeCl_3$. Tube 4: 2 ml of $FeCl_3$. Tube 5: 4 ml of $FeCl_3$.

FIG. 3A shows the appearance of the dried composition at 0.1 g per sample.

Figure 3B:
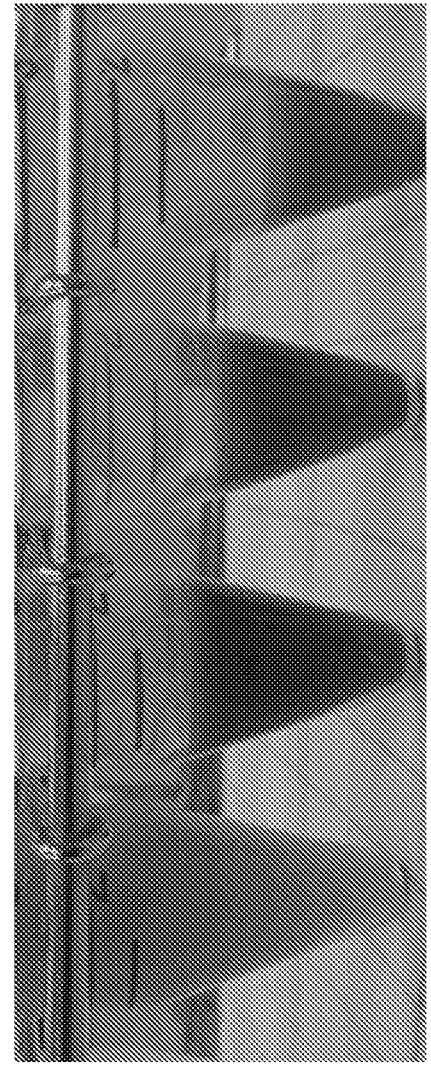

FIG. 3B shows the appearance of the composition after incubating with the phosphate buffer for 3 hr.

TABLE 6

Summary of the swell volume of each composition at different time points after incubating with the phosphate buffer at room temperature

| Tube #* | 20 min | 1 hr | 2 hr | 3 hr | 24 hr |
|---|---|---|---|---|---|
| 2 | 2 ml | 2 ml | 2 ml | 2 ml | 2 ml |
| 3 | 0.7 ml | 0.7 ml | 0.75 ml | 0.85 ml | 1.3 ml |
| 4 | 0.5 ml | 0.5 ml | 0.55 ml | 0.6 ml | 0.8 ml |
| 5 | 0.4 ml | 0.4 ml | 0.4 ml | 0.4 ml | 0.4 ml |

*Tube # 2-5 indicated the samples with the addition of 0.4, 1, 2, 4 ml of $FeCl_3$ (0.37 g/ml in water), respectively. Tube #1 was not assayed because there was no precipitate to be collected.

TABLE 7

Summary of the phosphate binding of the compositions

| Tube # | Phosphate bound at 24 hr, per g of dry composition | Phosphate bound at 24 hr, per ml of swell volume |
|---|---|---|
| 2 | 0.19 mmol | 0.009 mmol |
| 3 | 0.39 mmol | 0.030 mmol |
| 4 | 0.42 mmol | 0.057 mmol |
| 5 | 0.41 mmol | 0.104 mmol |

Figure 4A:
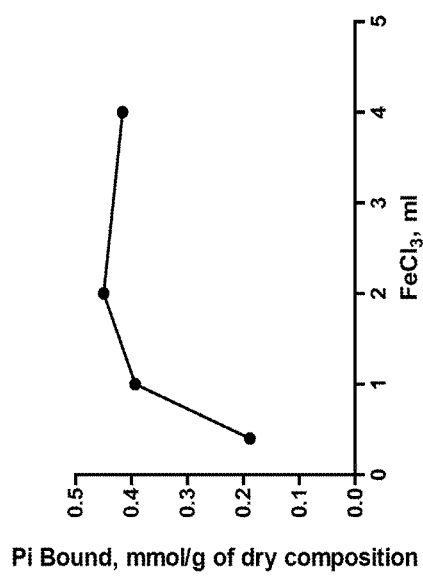
FIG. 4 is a graph illustrating the phosphate-binding capacity of the iron-gum Arabic composition per g of dry composition (FIG. 4A) or per ml of swell volume (FIG. 4B).
Figure 4B:
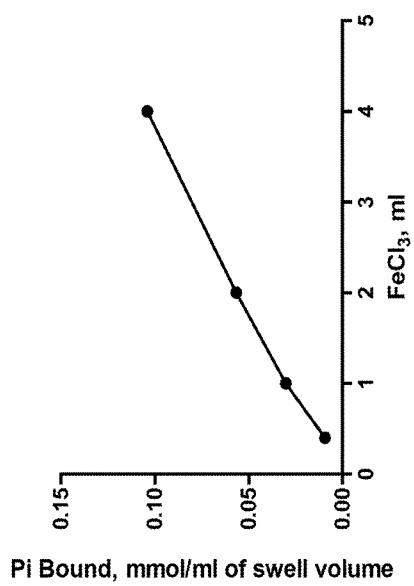

FIGS. 4A and 4B show the phosphate binding capacity of the compositions at different amounts of $FeCl_3$.

Example 7

Mixed 1 g gum Arabic into 15 ml of water. Pre-heated at 60° C.

Added 10 ml of $FeCl_3$ (0.37 g/ml in water) into the fiber component mixture. Added water to the final volume of 20 ml (pH at 1-2). Allowed the mixture to shake in a shaker at 60° C. for 1 hr.

Cooled the mixture to be <30° C. Added NaOH until pH was ~4.

Washed the precipitated material with water by filtration until the filtrate was clear and pH was ~7.

Dried the material using a food dehydrator for 24 hr. Ground the material using a nut grinder.

With 0.1 gram of the dried composition, added 5 ml of a 20 mM phosphate solution (as in Example 1) and incubated at room temperature for 24 hr. Centrifuged and collected the supernatant.

Determined the phosphate level in the supernatants using the phosphate colorimetric assay (Catalog #K410-500 from BioVision). Normalized the amount of phosphate bound by the quantity of the composition used (i.e. 0.1 g)

The swell volume of the composition at different time points after incubating with the phosphate buffer at room temperature: 20 min, 0.25 ml; 1 hr, 0.25 ml; 2 hr, 0.3 ml; 3 hr, 0.3 ml; 24 hr, 0.3 ml.

The phosphate binding results of the compositions at 24 h were 0.41 mmol per g of dry composition and 0.137 mmol per ml of swell volume.

Example 8

Mixed 1 g carboxymethylcellulose, or 1 g gum Arabic plus 0.1 g of cellulose and 0.1 g of lignin, or 1 g gum Arabic plus 0.1 g of cellulose and 0.1 g of dextrin and 0.1 g of lignin into 15 ml of water. Carboxymethylcellulose was gel-like and difficult to handle; the other samples formed a suspension. Pre-heated at 60° C.

Added 4 ml of $FeCl_3$ (0.37 g/ml in water) into the fiber component mixture. Added water to the final volume of 20 ml. Allowed the mixture to shake in a shaker at 60° C. for 1 hr.

Cooled the mixture to be <30° C. Added NaOH until pH was between 6 and 7.

Washed the precipitated material with water by filtration until the filtrate was clear.

Dried the material using a food dehydrator for 24 hr. Ground the material using a nut grinder.

With 0.1 gram of the dried composition, added 5 ml of a 20 mM phosphate solution (as in Example 1) to each sample and incubated at room temperature for 3 hr. Centrifuged and collected the supernatant.

Determined the phosphate level in the supernatants using the phosphate colorimetric assay (Catalog #K410-500 from BioVision). Normalized the amount of phosphate bound by the quantity of the composition used (i.e. 0.1 g).

TABLE 8

Summary of the phosphate binding of the compositions

| Composition | Phosphate bound at 3 hr |
|---|---|
| Carboxymethylcellulose* | 0.31 mmol per g of dry composition |
| Gum Arabic + cellulose + lignin | 0.24 mmol per g of dry composition |
| Gum Arabic + cellulose + lignin + dextrin | 0.42 mmol per g of dry composition |

*The result for the carboxymethylcellulose preparation may not be accurate due to the difficulty in preparing the sample.

Determined the iron level in the supernatants using the QuantiChrom™ Iron Assay Kit by BioAssay System (catalog # DIFE-250). Normalized the amount of iron level by the quantity of the composition used (i.e. 0.1 g).

TABLE 9

Summary of the iron levels in the supernatants of the compositions

| Composition | Iron level at 3 hr |
|---|---|
| Carboxymethylcellulose | 198 μg per g of dry composition |
| Gum Arabic + cellulose + lignin | 19 μg per g of dry composition |
| Gum Arabic + cellulose + lignin + dextrin | 40 μg per g of dry composition |

Example 9

Mixed 0.9 g of gum Arabic plus 0.1 g of gum guar, or 0.8 g of gum Arabic plus 0.2 g of gum guar, or 0.9 g of gum Arabic plus 0.1 g of gum guar plus 0.1 g of amylopectin, or 0.9 g of gum Arabic plus 0.1 g of gum guar plus 0.1 g of corn starch, or 1 g gum Arabic alone into 25 ml of water. Pre-heated at 60° C. All samples formed a suspension.

Added 4 ml of $FeCl_3$ (0.37 g/ml in water) into the fiber component mixture. Added water to the final volume of 30 ml (pH at 1-2). Allowed the mixture to shake in a shaker at 60° C. for 1 hr.

Cooled the mixture to be <30° C. Added NaOH until pH was 8-10.

Washed the precipitated material with water by filtration until the filtrate was clear.

Dried the material using a food dehydrator for 24 hr. Ground the material using a nut grinder.

With 0.1 gram of the dried composition, added 5 ml of a 20 mM phosphate solution (as in Example 1) to each sample and incubated at room temperature for 3 hr. Centrifuged and collected the supernatant.

Determined the phosphate level in the supernatants using the phosphate colorimetric assay (Catalog #K410-500 from BioVision). Normalized the amount of phosphate bound by the quantity of the composition used (i.e. 0.1 g).

TABLE 10

Summary of the phosphate binding of the compositions

| Composition | Phosphate bound at 3 hr |
|---|---|
| 0.9 g gum Arabic + 0.1 g of gum guar | 0.31 mmol per g of dry composition |
| 0.8 g gum Arabic + 0.2 g of gum guar | 0.25 mmol per g of dry composition |
| 0.9 g gum Arabic + 0.1 g of gum guar + 0.1 g of amylopectin | 0.21 mmol per g of dry composition |
| 0.9 g gum Arabic + 0.1 g of gum guar + 0.1 g of corn starch | 0.22 mmol per g of dry composition |
| 1 g gum Arabic | 0.32 mmol per g of dry composition |

Example 10

Dissolved 50 g gum Arabic completely in water at 60° C.

Added 200 ml $FeCl_3$ (in solution as in Example 1). Added water to 1 liter (final volume).

Allowed the mixture to shake in a shaker at 60° C. for 1 hr.

Cooled the mixture to be <30° C. Added NaOH until pH was between 6 and 7.

Washed the precipitated material with water by filtration until the filtrate was clear and pH was neutral.

Dried the material using a food dehydrator for 24 hr. Ground the material using a nut grinder. About 55 g of Composition 1 was obtained.

Figure 5:
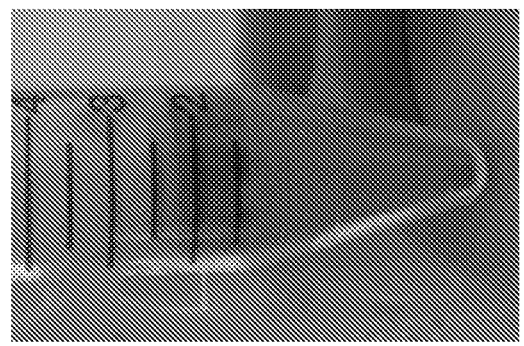
FIG. 5 illustrates the physical appearance of the iron-gum Arabic composition.

FIG. 5 shows that the volume of 3 g of the dried material in the loose powder form was at 2.2 ml. The density was at 1.36 g/ml (g/cm$^3$). By helium pycnometer, the density was determined to be 1.95 g/cm$^3$.

By inductively coupled plasma optical emission spectrometry (ICP-OES), the iron content in the dry composition (named Composition 1) was determined to be 21% (i.e. 0.21 g of iron in 1 g of dry composition).

To 0.1 gram of the dried composition, added 5 ml of a 20 mM phosphate solution (as in Example 1) and incubated at room temperature for 3 and 24 hr. Centrifuged and collected the supernatant.

In a different study, to 0.1 gram of the dried composition, added 5 ml of simulated gastric fluid (0.2% (w/v) NaCl, 0.7% (v/v) HCl, without pepsin) and sonicated for 5 min at 60° C. by a cell distruptor at the maximal speed. Centrifuged and collected the supernatant immediately after the sonication or 4 days after the sonication.

Determined the iron level in the supernatants using the QuantiChrom™ Iron Assay Kit, Catalog # DIFE-250 (BioAssay Systems, Hayward, Calif.).

TABLE 11

Summary of the iron level in the supernatant of the composition

| Time | Iron level in phosphate solution | Iron level in gastric fluid |
|---|---|---|
| At 3 hr | 24 µg per g of dry composition | — |
| At 24 hr | 41 µg per g of dry composition | — |
| Immediate after sonication | — | 1033 µg per g of dry composition |
| 4 days after sonication | — | 1089 µg per g of dry composition |

The iron released into the phosphate solution at 24 hr was calculated to be 0.02%.

Figure 6:
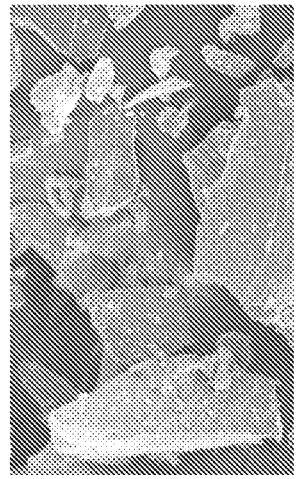
FIG. 6 a graph illustrating the SEM pictures at different magnifications of the iron-gum Arabic composition. A: X150. B: X300.
Figure 6:
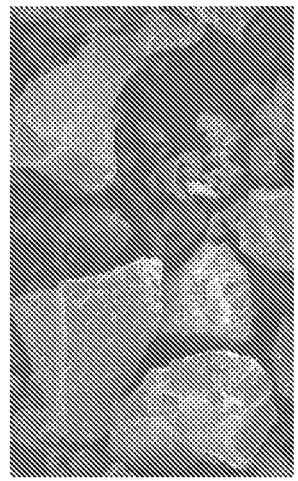

FIG. 6 is a graph illustrating the SEM pictures at different magnifications of the composition. A: X150. B: X300.

Example 11

Dissolved 50 g gum Arabic in water at 60° C. Mixed in 5 g cellulose, 5 g lignin and 5 g dextrin.

Added 200 ml $FeCl_3$ (in solution as in Example 1). Added water to 1 liter (final volume).

Allowed the mixture to shake in a shaker at 60° C. for 1 hr.

Cooled the mixture to be <30° C. Added NaOH until pH was between 6 and 7.

Washed the precipitated material with water by filtration until the filtrate was clear and pH was neutral.

Dried the material using a food dehydrator for 24 hr. Ground the material using a nut grinder. The yield was 56 g.

With 0.1 gram of the dried composition (named Composition 2), added 5 ml of a 20 mM phosphate solution (as in Example 1) and incubated at room temperature for 24 hr. Centrifuged and collected the supernatant.

Determined the phosphate or iron level in the supernatants as in Example 8.

TABLE 12

Summary of the phosphate binding and the iron levels in the supernatants of the samples

| Time | Phosphate bound | Iron level |
|---|---|---|
| At 24 hr | 0.31 mmol per g of dry composition | 58 µg per g of dry composition |

By helium pycnometer, the density of composition 2 was determined to be 1.90 g/cm$^3$.

Example 12

Prepared iron-gum Arabic (Composition 1) as described in Example 10. Prepared a large scale of iron-fiber (starting with 50 g of dietary fiber; Composition 3) as described in Example 3. Mixed the dry powder of the composition with a high phosphate diet (490 g normal powder rat chow (Teklad LM-485, Harlan, Mich., US) containing 0.7% phosphorus and 1% calcium plus 3.23 g $KH_2PO_4$+1.67 g $K_2HPO_4$) so that the amount of the composition was at 0.04-5% by weight of the total mixture. Mixed the mixture thoroughly.

As a control, prepared a mixture with Renagel (sevelamer hydrochloride) or Renvela (sevelamer carbonate) powder and normal rat chow and $KH_2PO_4$+$K_2HPO_4$ with the amount of sevelamer at 0.2-5% by weight of the total mixture. Mixed the mixture thoroughly.

Male, Sprague Dawley, rats were placed in metabolic cages with 1 rat per cage. Urine and feces samples were collected for 24 hr. Blood samples were collected from each rat for serum preparation.

Rats were fed with the diet containing high phosphates and different preparations as mentioned above.

After four days, the rats were placed in metabolic cages with 1 rat per cage. Urine and feces samples were collected for 24 hr. Blood samples were collected from each rat to prepare serum. Serum calcium (Ca) was measured using the Stanbio LiquiColor calcium assay kit (Catalog #0150-250, Stanbio, Boerne, Tex.). Serum and urine phosphorus/phosphate was determined using the BioVision phosphate colorimetric assay as mentioned above. Two grams from each 24-hr feces sample were ashed at 800° C. for 30 minutes. Ash was extracted with 5 ml of 12N HCl by vortexing and shaking at room temperature for ~60 min. The supernatant was collected by centrifugation and neutralized using an equal volume of 12N NaOH. The mixture was again centrifuged and the supernatant was collected for phosphate determination. Total urinary and fecal phosphate levels during a 24-hr period were calculated. The serum iron levels were determined using the QuantiChrom™ Iron Assay Kit (Catalog # DIFE-250, BioAssay Systems, Hayward, Calif.).

Figure 7:
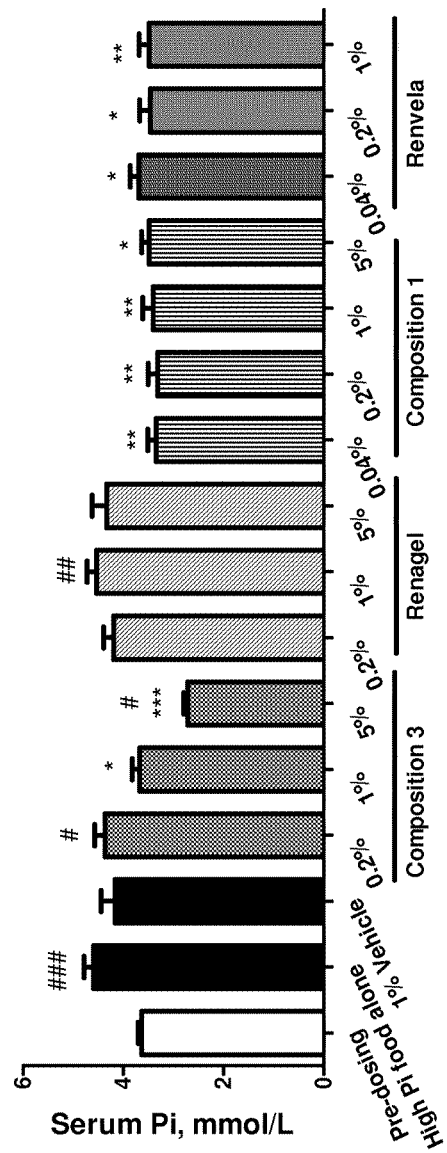
FIG. 7 is a graph illustrating serum phosphorus/phosphate (Pi) levels in rats fed a phosphate-enriched diet containing Vehicle (1% unprocessed gum Arabic), the iron-gum Arabic composition, Composition 3, sevelamer (Renvela or Renagel), or High Pi food alone (no treatment). #p<0.05, ##p<0.01, ###p<0.001 vs. Pre-dosing; *p<0.05, p<0.01, *p<0.001 vs. High Pi food alone

FIG. 7 shows the serum phosphate concentration in the rats fed the different food preparations.

Figure 8:
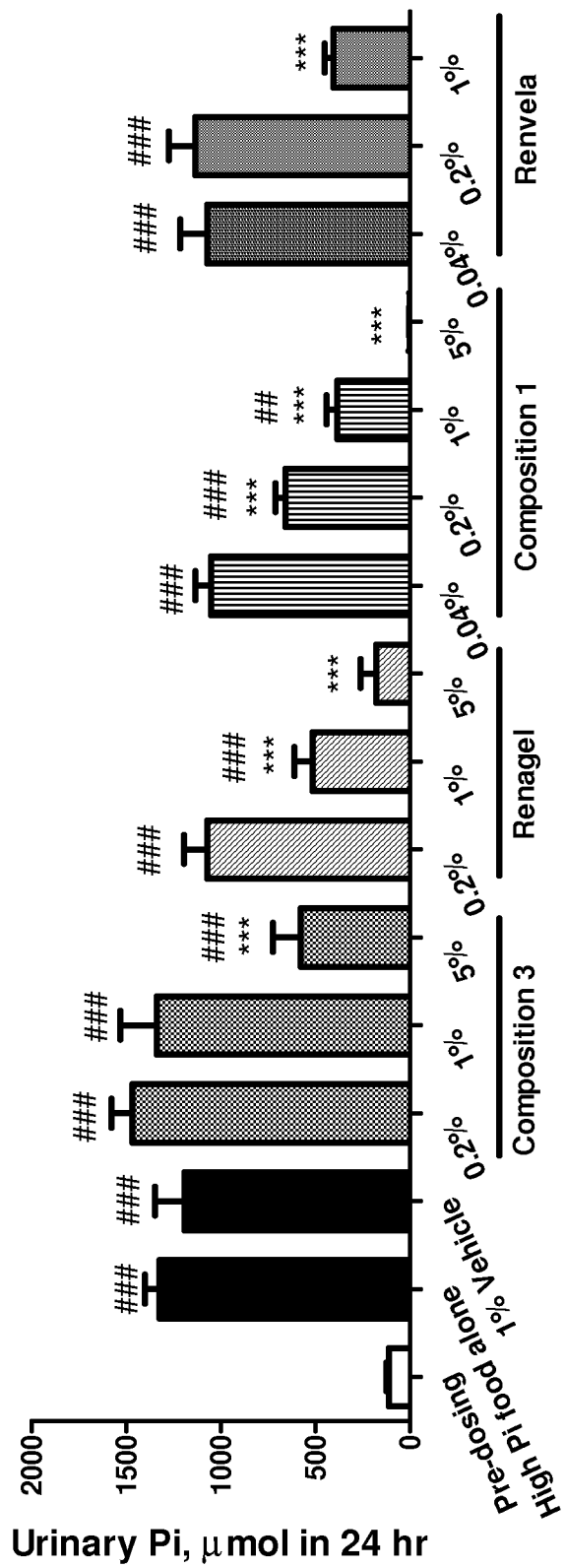
FIG. 8 is a graph illustrating urinary phosphorus/phosphate (Pi) levels in rats fed a phosphate-enriched diet containing Vehicle (1% unprocessed gum Arabic), the iron-gum Arabic composition, Composition 3, sevelamer (Renvela or Renagel), or High Pi food alone (no treatment). ##p<0.01, ###p<0.001 vs. pre-dosing; ***p<0.001 vs. High Pi food alone.

FIG. 8 shows the urinary phosphate concentration in the rats fed the different food preparations.

Figure 9:
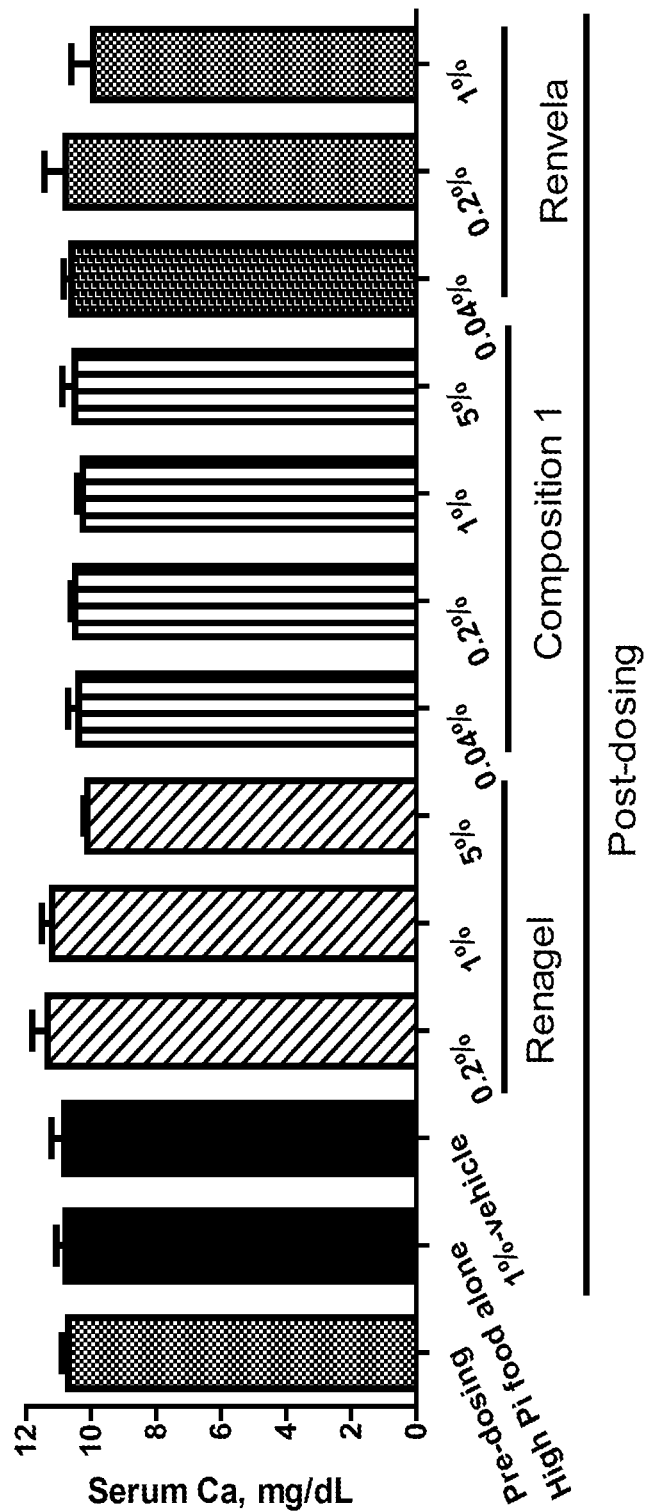
FIG. 9 is a graph illustrating serum calcium levels in rats fed a phosphate-enriched diet containing Vehicle (1% unprocessed gum Arabic), the iron-gum Arabic composition, sevelamer, or High Pi food alone (no treatment).

FIG. 9 shows the serum calcium concentration in the rats fed the different food preparations.

Figure 10:
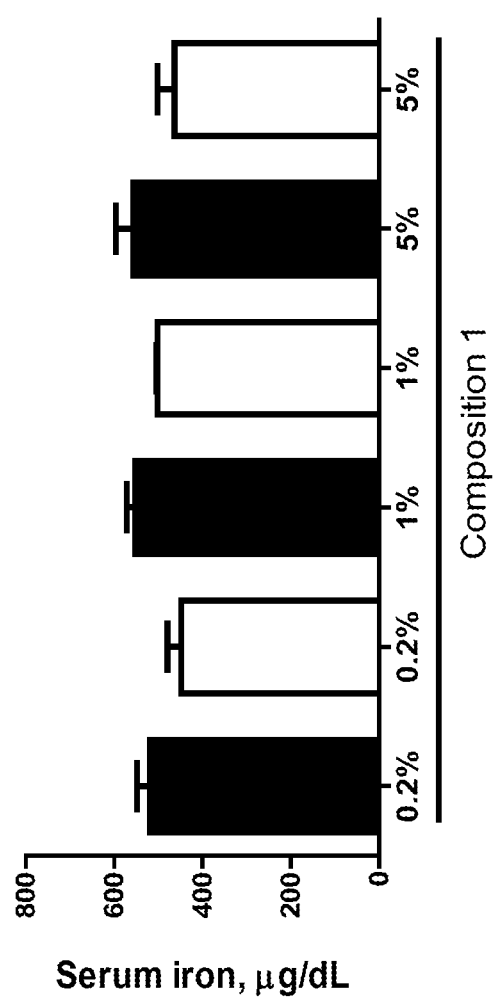
FIG. 10 is a graph illustrating serum iron levels in rats fed a phosphate-enriched diet containing the iron-gum Arabic composition. Solid bar: Pre-treatment. White bar: Post-treatment.

FIG. 10 shows the serum iron levels in the rats before treatment and after the iron-gum Arabic composition treatment. There was no significant difference in the serum iron levels.

Figure 11:
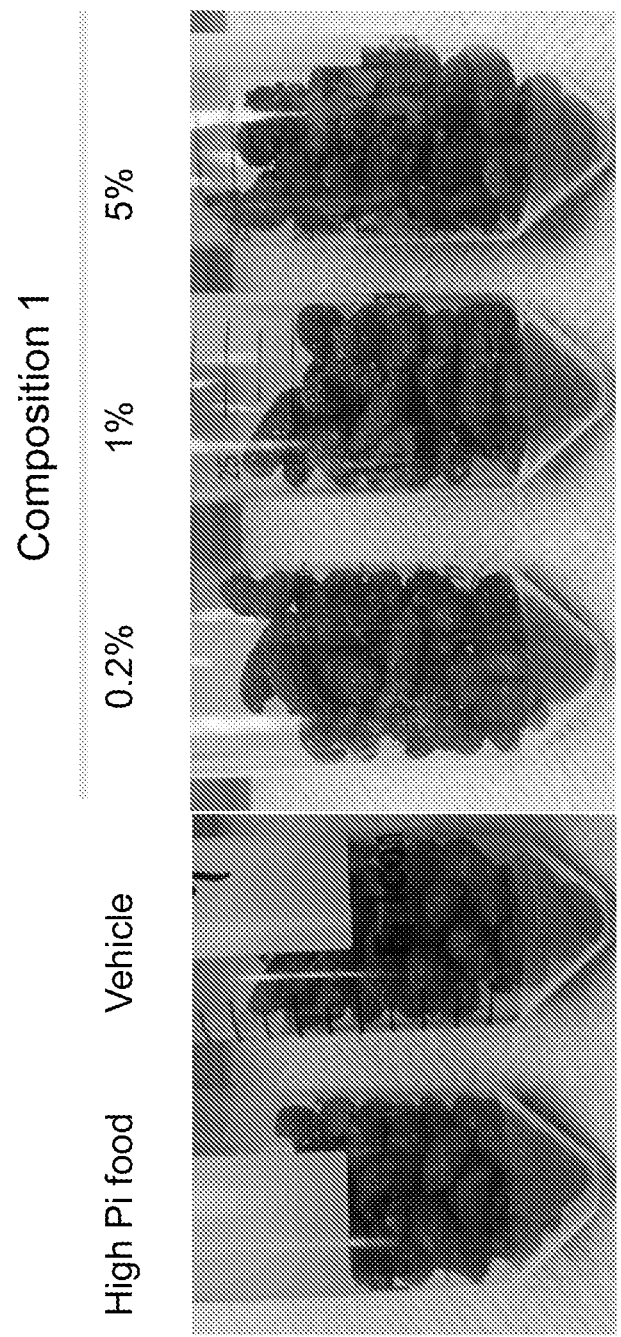
FIG. 11 shows the physical appearance of feces samples collected from rats treated with Vehicle (1% unprocessed gum Arabic), the iron-gum Arabic composition, or High Pi food alone (no treatment).

FIG. 11 shows the physical appearance of feces samples collected from rats treated with Composition 1.

Figure 12:
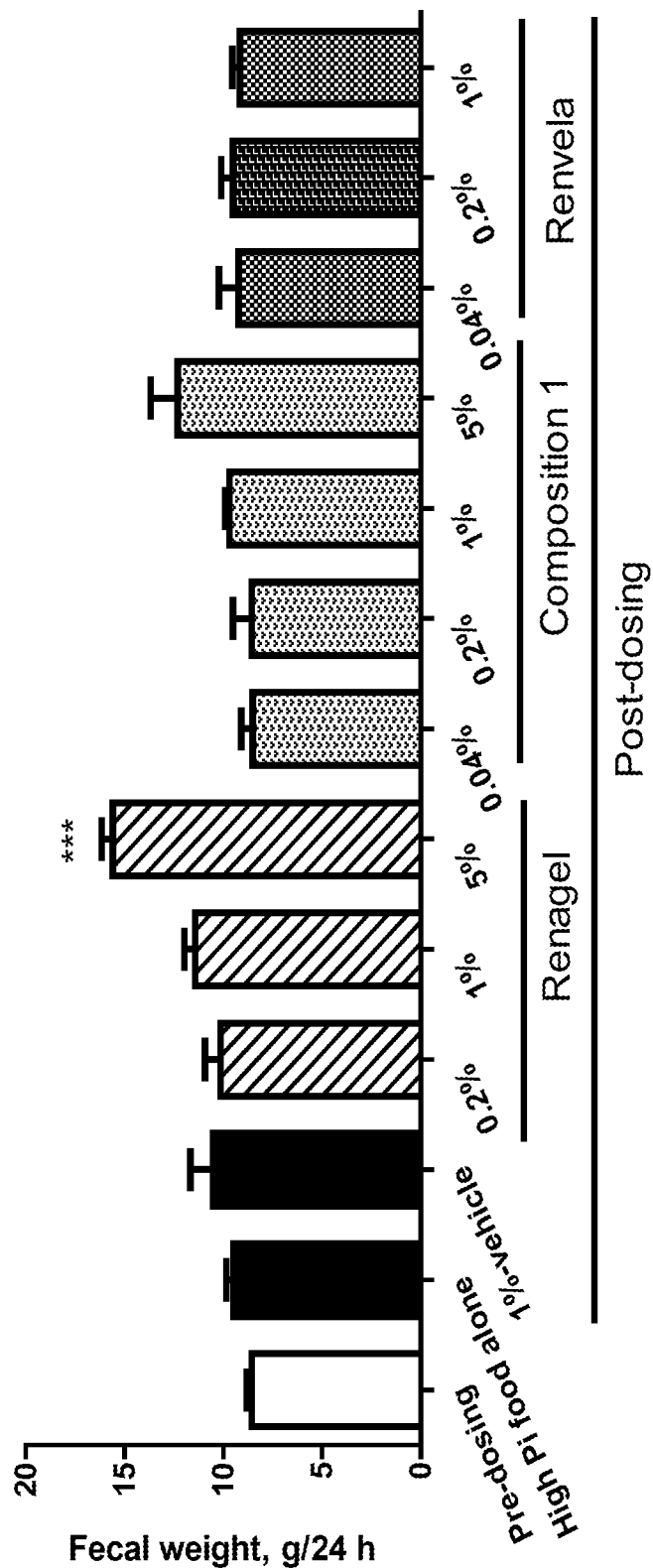
FIG. 12 is a graph illustrating fecal weights in rats fed a phosphate-enriched diet treated with Vehicle (1% unprocessed gum Arabic), the iron-gum Arabic composition, sevelamer, or High Pi food alone (no treatment). ***p<0.001 vs. High Pi food alone.

FIG. 12 shows that significant changes in fecal weights were only observed in the 5% Renagel groups.

Figure 13:
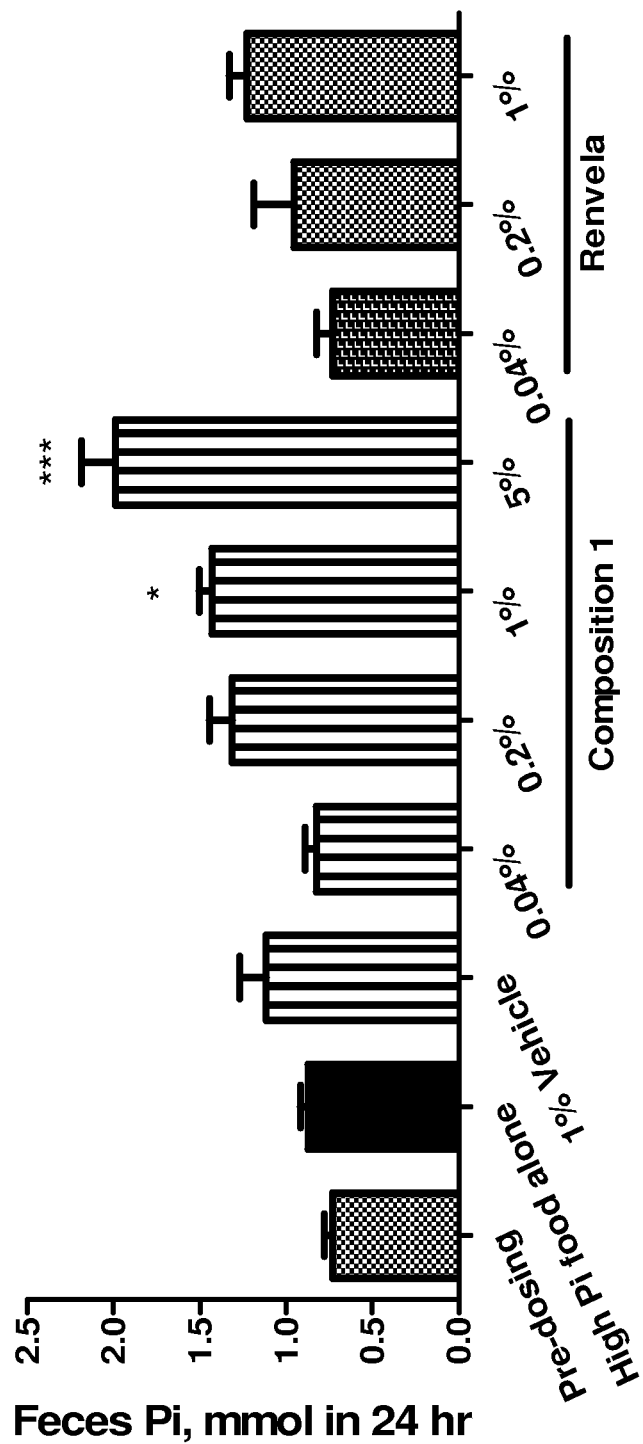
FIG. 13 is a graph illustrating fecal phosphate levels in rats fed a phosphate-enriched diet treated with Vehicle (1% unprocessed gum Arabic), the iron-gum Arabic composition, sevelamer, or High Pi food alone (no treatment). *p<0.05, ***p<0.001 vs. High Pi food alone.

FIG. 13 shows that the fecal phosphate levels were significantly higher in the groups treated with Composition 1 in a dose-dependent manner.

Example 13

Prepared Composition 1 as described in Example 10. Mixed the dry powder of the composition with a high phosphate diet (490 g normal powder rat chow (Teklad LM-485, Harlan, Mich., US) containing 0.7% phosphorus and 1% calcium plus 3.23 g $KH_2PO_4$+1.67 g $K_2HPO_4$) so that the amount of the composition was at 0.2% or 1% by weight of the total mixture. Mixed the mixture thoroughly.

As a control, prepared a mixture with Renvela (sevelamer carbonate) powder and normal rat chow and $KH_2PO_4$+$K_2HPO_4$ with the amount of sevelamer at 0.2 or 1% by weight of the total mixture. Mixed the mixture thoroughly.

The 5/6 nephrectomized rats were prepared and handled as previously described (Wu-Wong et al. Br J Pharmacol 2011; 164:551-60; Am J Nephrol 2013; 37:310-9). Briefly, the nephrectomy was performed on male, Sprague Dawley rats weighing ~200 g with a standard two-step surgical ablation procedure. At 6 weeks after the second surgery when uremia was established (as indicated by elevated serum creatinine and BUN levels), rats were fed a high phosphate diet (normal powder rat chow plus $KH_2PO_4$+$K_2HPO_4$ as described above) containing the iron-gum Arabic composition or Renvela (as described above) in food for 4 weeks. Untreated, age-matched Sham rats served as a control group. Blood was drawn on Day 0 (24 hr before dosing), Day 14, and Day 28. Each animal was placed in a metabolic cage on Day 0 and also on Day 14, and Day 28 and urine and feces samples were collected during a period of 24 h.

Serum and urine Ca (calcium) was measured using the Stanbio LiquiColor calcium assay kit as described above. Serum and urine creatinine were measured using a chemistry analyzer. Serum BUN concentrations were measured using the Stanbio enzymatic BUN assay kit (Catalog #2050-450). Serum and urine phosphorus/phosphate was determined using the BioVision phosphate colorimetric assay as described above. Two grams from each 24-hr feces sample were ashed at 800° C. for 30 minutes. Ash was extracted with 5 ml of 12N HCl by vortexing and shaking at room temperature for ~60 min. The supernatant was collected by centrifugation and neutralized using an equal volume of 12N NaOH. The mixture was again centrifuged and the supernatant was collected for phosphate determination. Total urinary and fecal phosphate levels during a 24-hr period were calculated. Serum iron levels were determined using the QuantiChrom™ Iron Assay Kit as described above.

Differences among groups were assessed using a one-way ANOVA followed by a Dunnett's post-hoc test. A t-test was used to assess before-treatment and after-treatment differences within the same group. A sample size of n=8-12 was used in each group.

Figure 15:
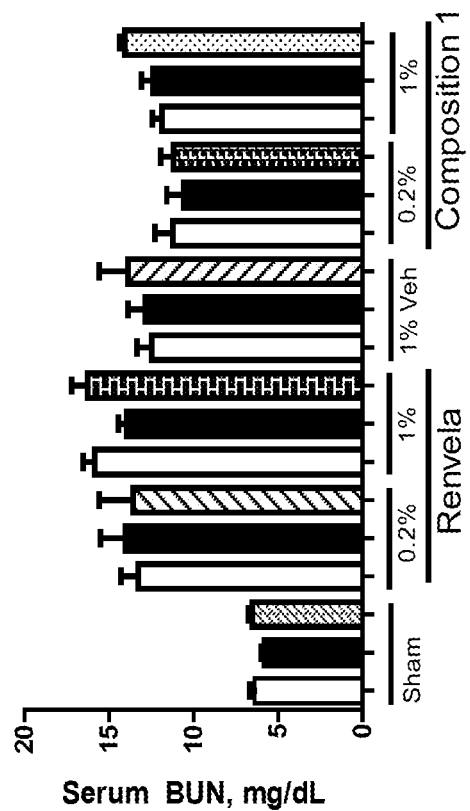
FIG. 15 is a graph illustrating the serum BUN levels in the 5/6 NX uremic rats fed a phosphate-enriched diet containing Vehicle (1% unprocessed gum Arabic), the iron-gum Arabic composition, sevelamer. Untreated, age-matched Sham rats served as a control group. Open bar: pre-dosing. Solid bar: Week 2 after dosing. Patterned bar: Week 4 after dosing.
Figure 14:
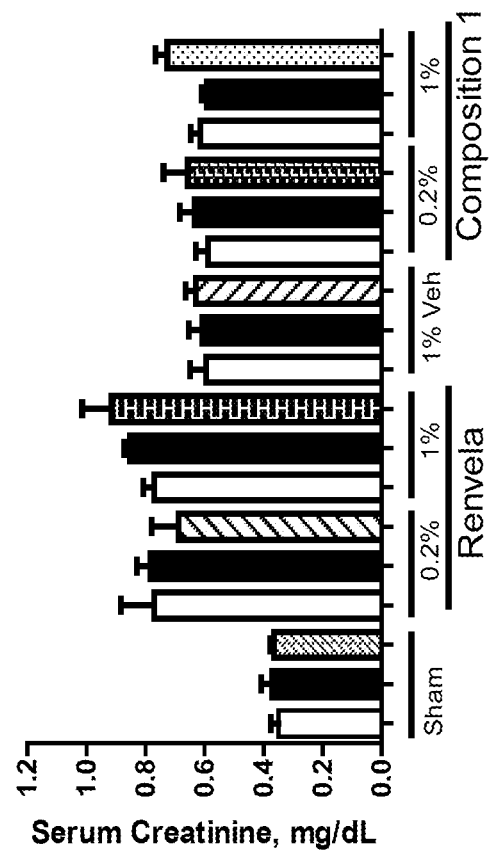
FIG. 14 is a graph illustrating the serum creatinine levels in the 5/6 nephrectomized (NX) uremic rats fed a phosphate-enriched diet containing Vehicle (1% unprocessed gum Arabic), the iron-gum Arabic composition, sevelamer. Untreated, age-matched Sham rats served as a control group. Open bar: pre-dosing. Solid bar: Week 2 after dosing. Patterned bar: Week 4 after dosing.

FIGS. 14 and 15 show that the serum creatinine and BUN levels were elevated significantly in the 5/6 NX rats, indicating a uniform uremic state. Treatment with Renvela or the iron-gum Arabic composition at the indicated doses had no significant effects (vs. pre-dosing in the same group).

Figure 16:
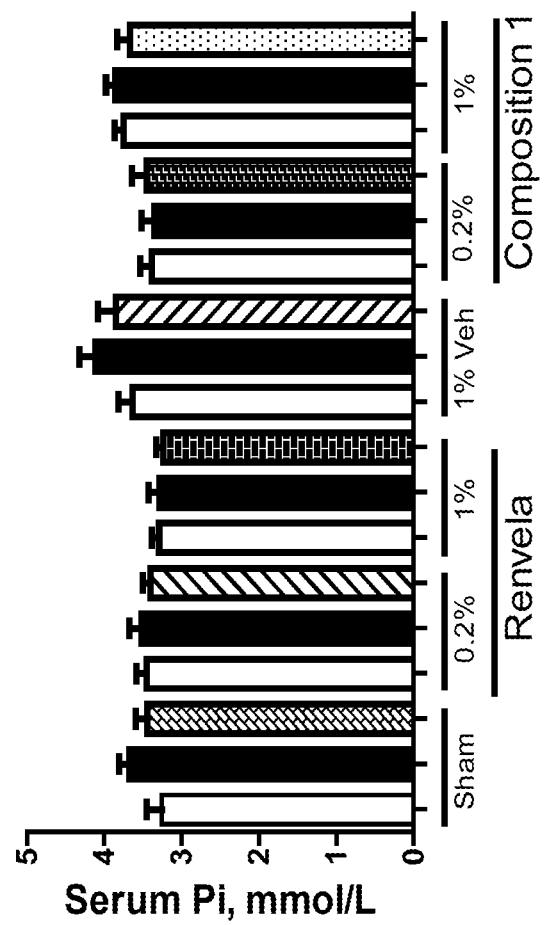
FIG. 16 is a graph illustrating serum phosphorus/phosphate (Pi) levels in the 5/6 NX uremic rats fed a phosphate-enriched diet containing Vehicle (1% unprocessed gum Arabic), the iron-gum Arabic composition, sevelamer. Untreated, age-matched Sham rats served as a control group. Open bar: pre-dosing. Solid bar: Week 2 after dosing. Patterned bar: Week 4 after dosing.

FIG. 16 shows the serum phosphate concentration in the rats fed the different food preparations. Serum phosphate levels trended high in the Sham and Vehicle-treated groups (vs. pre-dosing). Treatment with Renvela or the iron-gum Arabic composition at the indicated doses maintained the same serum Pi level as the pre-dosing level.

Figure 17:
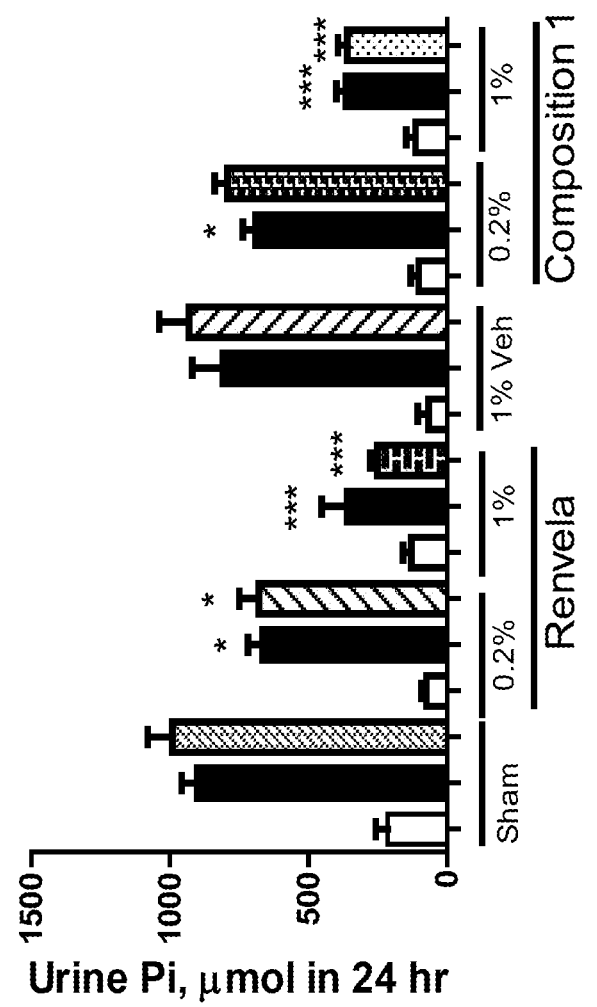
FIG. 17 is a graph illustrating urinary phosphorus/phosphate (Pi) levels in the 5/6 NX uremic rats fed a phosphate-enriched diet containing Vehicle (1% unprocessed gum Arabic), the iron-gum Arabic composition, sevelamer. Untreated, age-matched Sham rats served as a control group. Open bar: pre-dosing. Solid bar: Week 2 after dosing. Patterned bar: Week 4 after dosing. *p<0.05, ***p<0.001 vs. Sham, same time point

FIG. 17 shows the urinary phosphate concentration in the rats fed the different food preparations.

Figure 18:
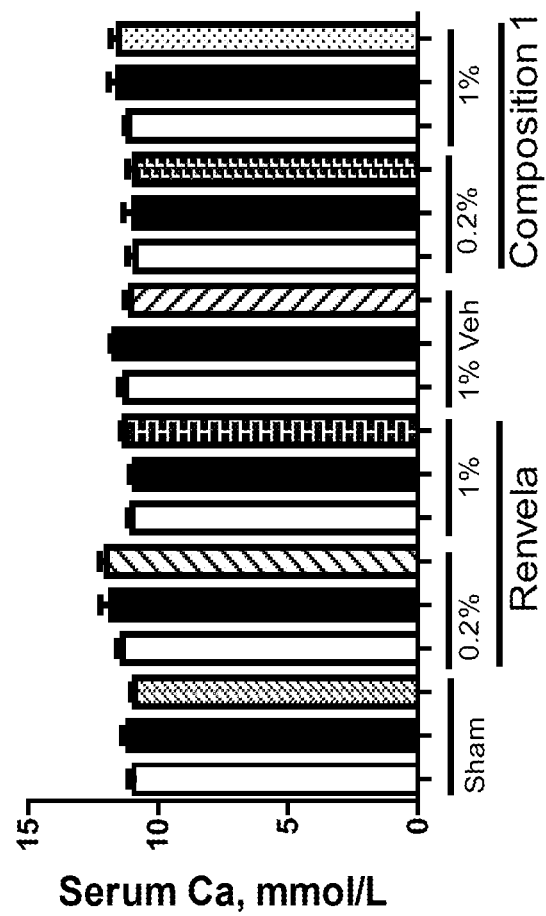
FIG. 18 is a graph illustrating serum calcium levels in the 5/6 NX uremic rats fed a phosphate-enriched diet containing Vehicle (1% unprocessed gum Arabic), the iron-gum Arabic composition, sevelamer. Untreated, age-matched Sham rats served as a control group. Open bar: pre-dosing. Solid bar: Week 2 after dosing. Patterned bar: Week 4 after dosing.

FIG. 18 shows the serum calcium concentration in the rats fed the different food preparations.

Figure 19:
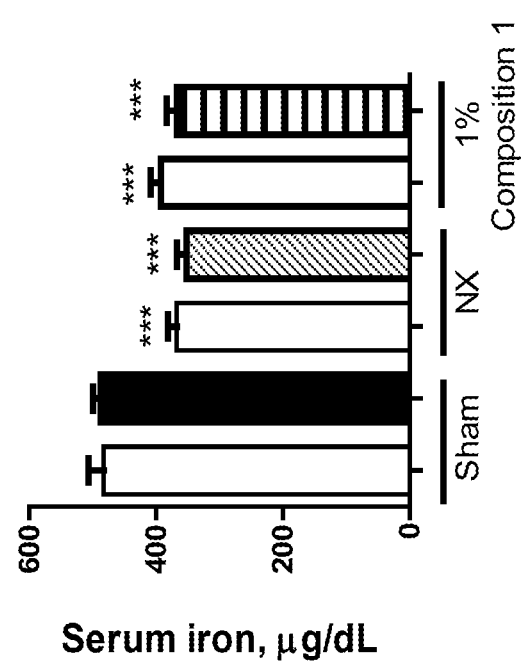
FIG. 19 is a graph illustrating serum iron levels in the 5/6 NX uremic rats fed a phosphate-enriched diet containing Vehicle (1% unprocessed gum Arabic) or 1% of the iron-gum Arabic composition. Untreated, age-matched Sham rats served as a control group. Open bar: pre-dosing. Solid and patterned bar: Week 4 after dosing. ***p<0.001 vs. Sham-predosing.

FIG. 19 shows the serum iron levels were significantly lower in the NX rats; no significant change in serum iron was observed in the group treated with 1% iron-gum Arabic composition (vs. the NX group).

Figure 20:
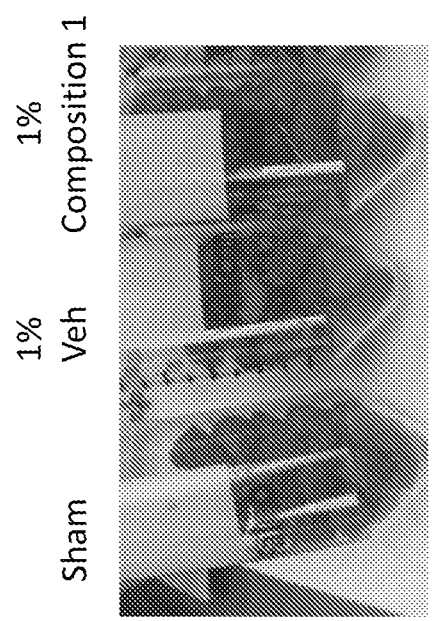
FIG. 20 shows the physical appearance of feces samples collected from the 5/6 NX uremic rats fed a phosphate-enriched diet containing Vehicle (1% unprocessed gum Arabic) or 1% of the iron-gum Arabic composition. Untreated, age-matched Sham rats served as a control group.

FIG. 20 shows the physical appearance of feces samples collected from rats treated with the iron-gum Arabic composition.

Figure 21:
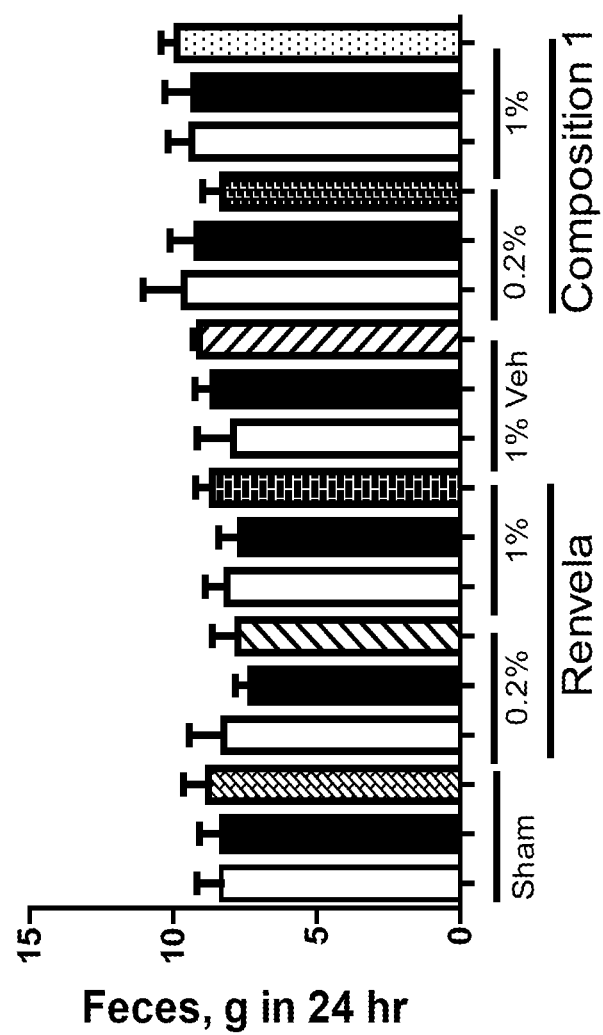
FIG. 21 is a graph illustrating fecal weights in the 5/6 NX uremic rats fed a phosphate-enriched diet containing Vehicle (1% unprocessed gum Arabic), the iron-gum Arabic composition, sevelamer. Untreated, age-matched Sham rats served as a control group. Open bar: pre-dosing. Solid bar: Week 2 after dosing. Patterned bar: Week 4 after dosing.

FIG. 21 shows that there were no significant changes in fecal weights.

Figure 22:
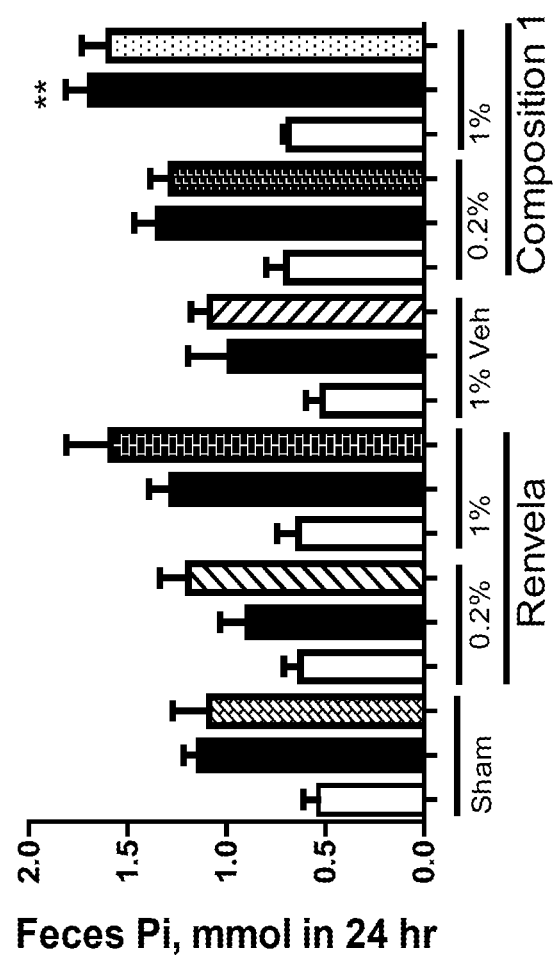
FIG. 22 is a graph illustrating fecal phosphate levels in the 5/6 NX uremic rats fed a phosphate-enriched diet containing Vehicle (1% unprocessed gum Arabic), the iron-gum Arabic composition, sevelamer. Untreated, age-matched Sham rats served as a control group. Open bar: pre-dosing. Solid bar: Week 2 after dosing. Patterned bar: Week 4 after dosing. **p<0.01 vs. sham, same time point.

FIG. 22 shows that the fecal phosphate levels were significantly higher in the groups treated with the iron-gum Arabic composition.

Example 14

Took 0.1 gram of dry Composition 1. Added 5 ml of simulated gastric fluid (0.2% (w/v) NaCl, 0.7% (v/v) HCl, without pepsin). Incubated at 37° C.

As a control, 0.1 g of sevelamer (Renvela) in powder form in the place of the iron-gum Arabic composition was prepared simultaneously.

Figure 23:
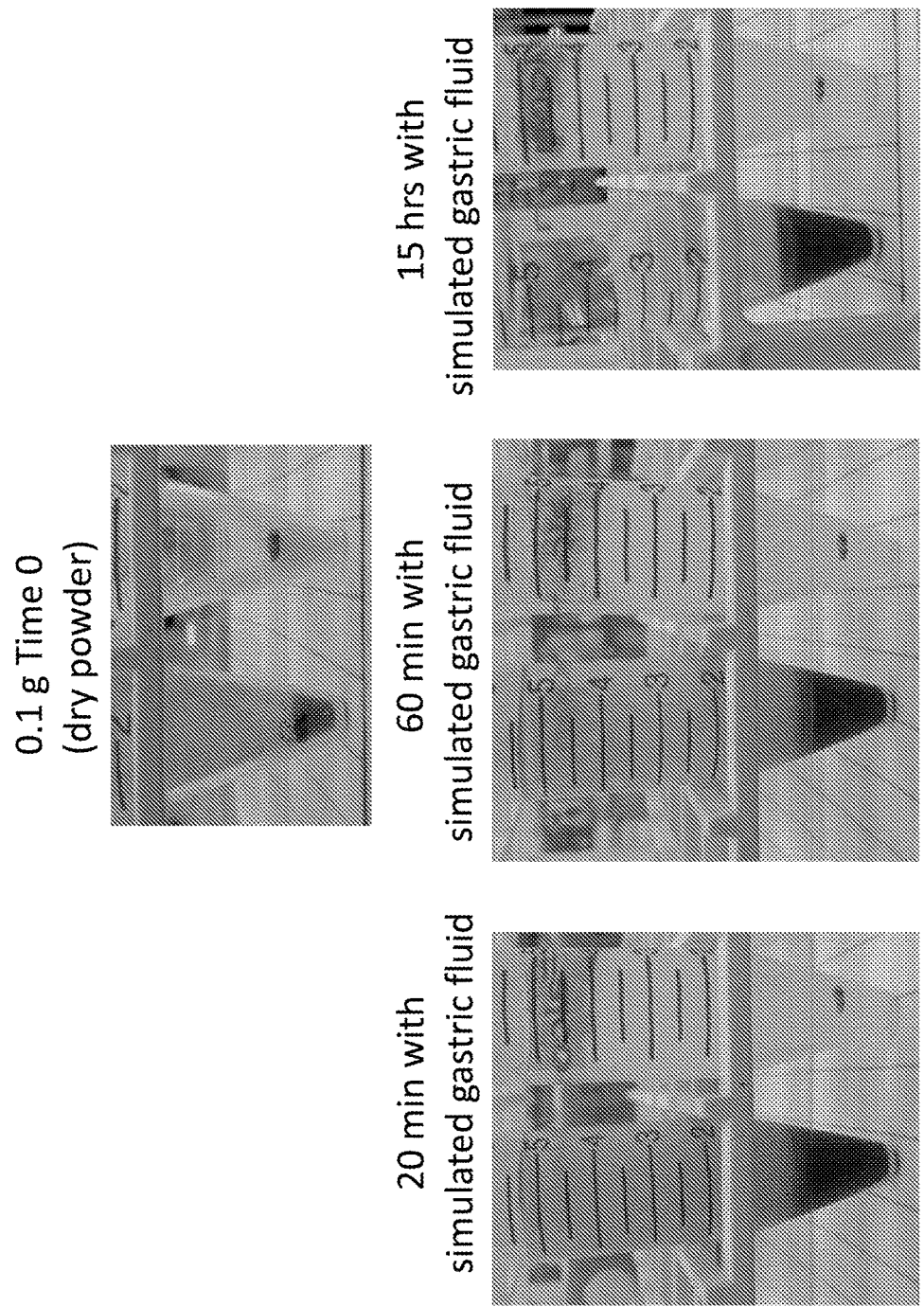
FIG. 23 shows the physical appearance of the iron-gum Arabic composition (left) vs. sevelamer (Renvela, right) at different time points after incubating with simulated gastric fluid at 37° C.

FIG. 23 shows the physical appearance of the iron-gum Arabic composition vs. sevelamer at different time points during the incubation at 37° C.

The volume ($cm^3$) of the iron-gum Arabic composition vs. sevelamer at 60 min after exposure to simulated gastric fluid: 0.4 vs. 4.1 $cm^3$. Large swelling volume is potentially associated with GI discomfort.

Example 15

Prepared the phosphate solution as described in Example 1 with the pH ranging from 2 to 9, and with a 20 mM final phosphate concentration.

Added 0.1 gram of dry Composition 1 to 5 mL of the phosphate buffers at different pH. Measured the pH again. Incubated at room temperature for 24 hr. Centrifuged and collected the supernatant for phosphate determination by the phosphate colorimetric assay (Catalog #K410-500 from BioVision).

TABLE 13

Summary of the phosphate binding for Composition 1

| pH (Final) | Phosphate bound at 2 hr |
|---|---|
| 1.92 | 0.49 mmol per g of dry composition |
| 2.30 | 0.49 mmol per g of dry composition |
| 5.54 | 0.34 mmol per g of dry composition |
| 8.12 | 0.32 mmol per g of dry composition |

Example 16

Prepared three batches of the iron-gum Arabic composition as in Example 10 except that the third batch was partially washed (indicated by the presence of color in the filtrate).

The samples were analyzed by the XPS (X-ray Photoelectron Spectroscopy). XPS experiments were performed using the Kratos Axis-165 instrument. Samples were irradiated by a monochromatic Al-$K_\alpha$ X-ray source (15 kV, 10 mA) at an angle of 30 degrees from the sample surface. Photoelectrons were detected by 8 channeltrons of the concentric hemispherical analyzer over an area of 700×300 microns, with a spectrometer take-off angle of zero. The detection was achieved using the constant analyzer energy (CAE) mode.

Survey scans were acquired with a pass-energy of 160 eV, 1.0 eV step-size and 100 msec dwell time; while narrow scans were acquired with a pass-energy of 20 eV, 0.1 eV step-size and 200 msec. All scans were performed with the charge-neutralization system running. Charge-referencing were done with the adventitious carbon peak position of 284.8 eV. The XPS analysis chamber base-Pressure was better than 2E-10 Torr, while working-Pressure was better than 3E-9 Torr.

Figure 24A:
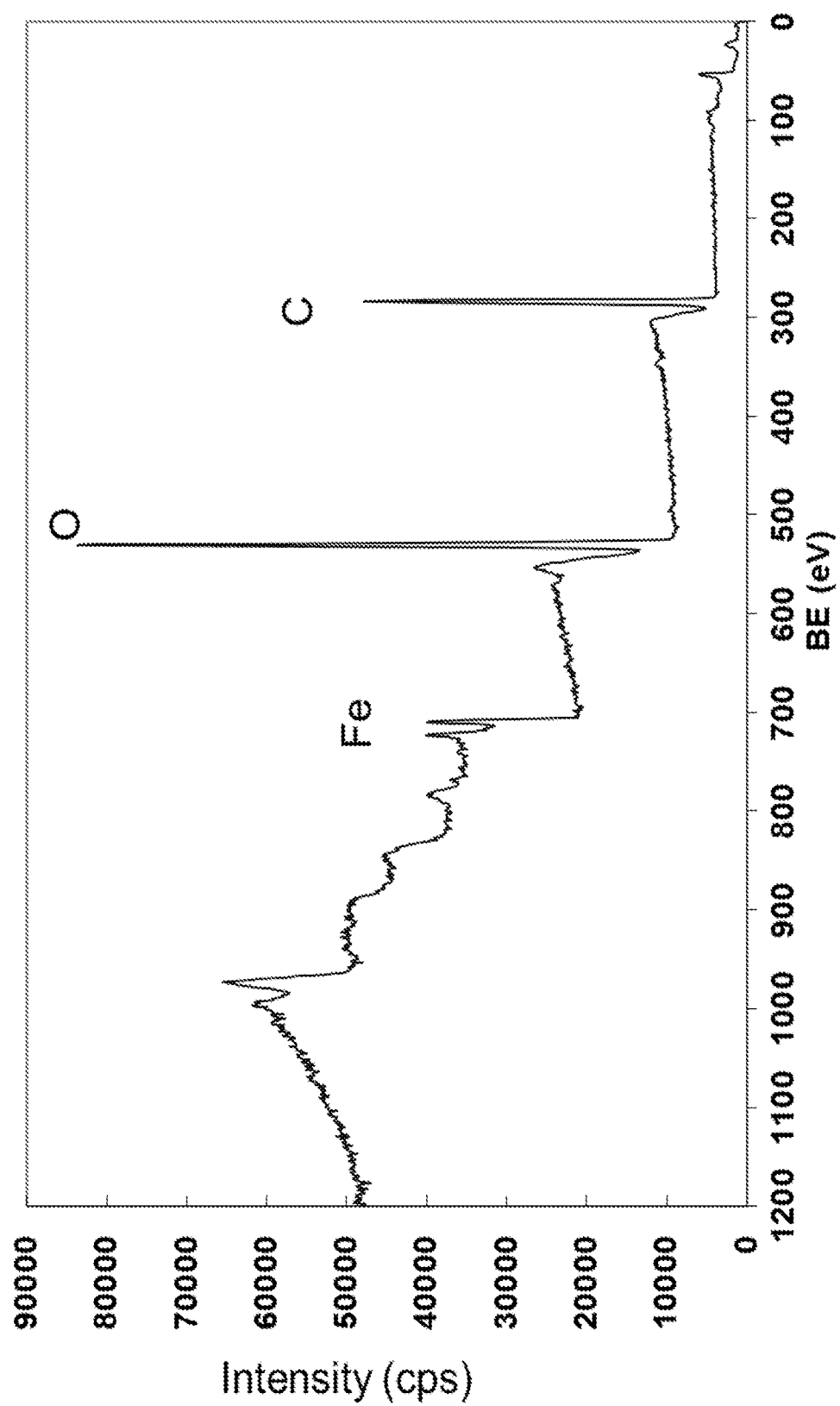
(FIG. 24A) the survey spectrum, (FIG. 24B) C 1s, (FIG. 24C) Fe 2p.

FIG. 24A shows the survey spectra for the first batch of the iron-gum Arabic composition from the XPS analysis. The semi-quantitation data are listed in Table 14.

TABLE 14

Results of analysis of Fe(III)-gum Arabic composition (Batch 1)

| Peak | Position BE (eV) | FWHM (eV) | Raw Area (CPS) | RSF | Atomic Mass | Atomic Conc, % | Mass Conc, % |
|---|---|---|---|---|---|---|---|
| Fe 2p | 710.000 | 5.347 | 199770.0 | 2.957 | 55.846 | 6.36 | 21.86 |
| C 1s | 284.000 | 3.762 | 175115.0 | 0.278 | 12.011 | 57.52 | 42.55 |
| O 1s | 531.000 | 3.986 | 306640.0 | 0.780 | 15.999 | 36.12 | 35.59 |

Figure 24B:
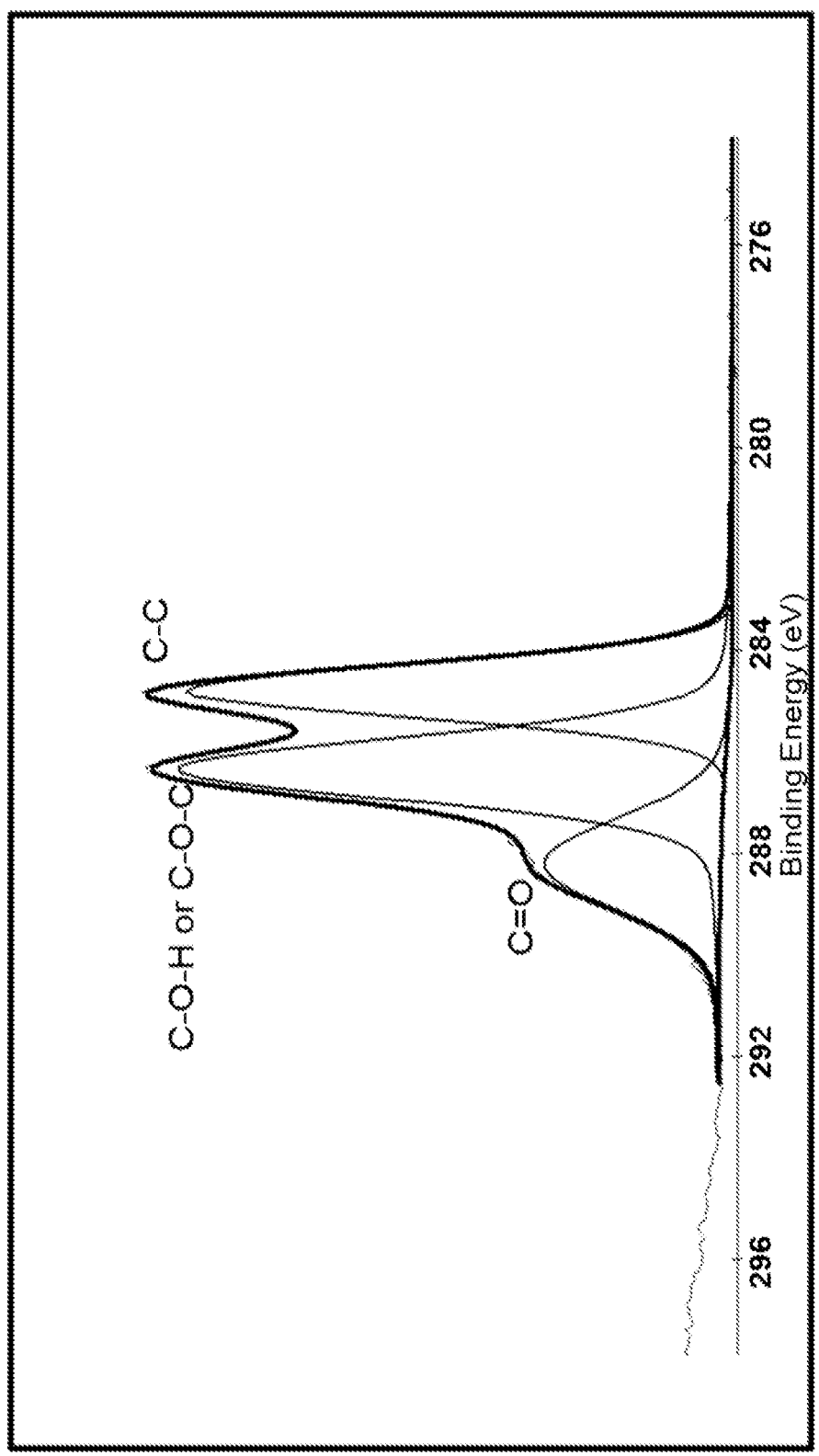
FIG. 24 shows spectra from XPS analysis of the iron-gum Arabic composition.

FIG. 24B shows the C is spectrum for the iron-gum Arabic composition. The result is consistent with the chemical composition of gum Arabic as the main component of the complex.

Figure 24C:
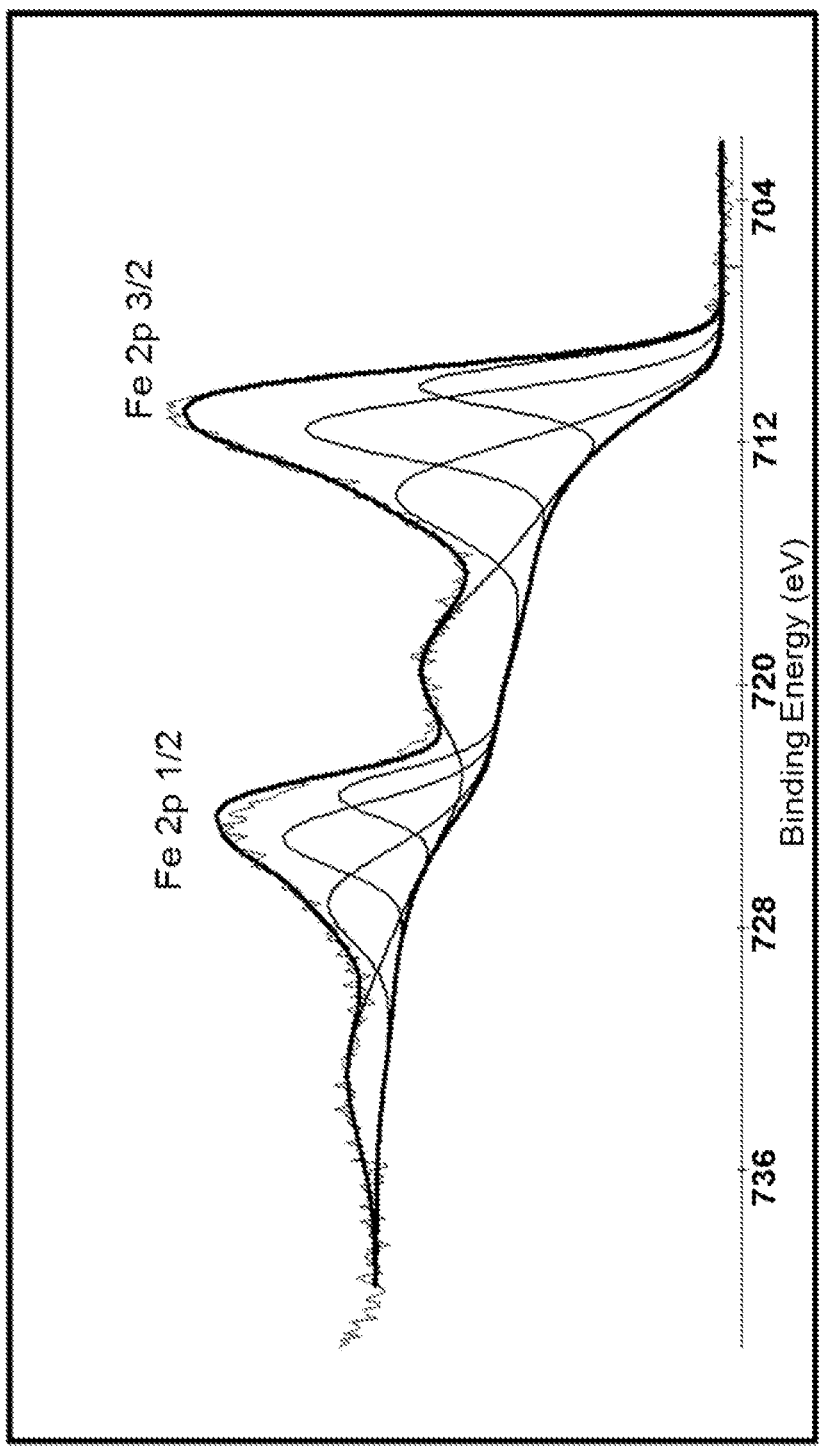

FIG. 24C shows the Fe 2p spectrum. The result indicates the presence of iron ion, and the potential interaction between iron ion and oxygen or carbon.

Similar results were obtained for the second batch of the iron-gum Arabic composition. The semi-quantitation data are listed in Table 15.

TABLE 15

Results of analysis of Fe(III)-gum Arabic composition (Batch 2)

| Peak | Position BE (eV) | FWHM (eV) | Raw Area (CPS) | RSF | Atomic Mass | Atomic Conc, % | Mass Conc, % |
|---|---|---|---|---|---|---|---|
| Fe 2p | 709.000 | 5.208 | 163865.0 | 2.957 | 55.846 | 6.06 | 20.88 |
| C 1s | 284.000 | 3.623 | 145160.0 | 0.278 | 12.011 | 55.42 | 41.08 |
| O 1s | 531.000 | 3.586 | 281352.5 | 0.780 | 15.999 | 38.52 | 38.04 |

The semi-quantitation data for the third batch of the iron-gum Arabic composition are listed in Table 16.

TABLE 16

Results of analysis of Fe(III)-gum Arabic composition (Batch 3)

| Peak | Position BE (eV) | FWHM (eV) | Raw Area (CPS) | RSF | Atomic Mass | Atomic Conc, % | Mass Conc, % |
|---|---|---|---|---|---|---|---|
| Fe 2p | 710.000 | 6.482 | 19842.5 | 2.957 | 55.846 | 4.13 | 14.32 |
| C 1s | 285.000 | 3.704 | 24335.0 | 0.278 | 12.011 | 52.32 | 39.00 |
| O 1s | 531.000 | 3.496 | 50605.0 | 0.780 | 15.999 | 39.02 | 38.74 |
| Cl 2p | 198.000 | 4.095 | 2830.0 | 0.891 | 35.460 | 1.89 | 4.17 |
| Na 1s | 1070.000 | 3.049 | 6400.0 | 1.685 | 22.990 | 2.64 | 3.77 |

The semi-quantitation data for gum Arabic alone (without processing) are listed in Table 17.

TABLE 17

Results of analysis of gum Arabic composition without processing

| Peak | Position BE (eV) | FWHM (eV) | Raw Area (CPS) | RSF | Atomic Mass | Atomic Conc, % | Mass Conc, % |
|---|---|---|---|---|---|---|---|
| C 1s | 284.000 | 3.438 | 193320.0 | 0.278 | 12.011 | 61.37 | 54.39 |
| O 1s | 531.000 | 2.994 | 339340.0 | 0.780 | 15.999 | 38.63 | 45.61 |

Example 17

Mixed 0.5 g gum Arabic into 10 ml of water.

Added 2 ml of $FeCl_3$ (0.37 g/ml in water) into the fiber component. Added water to the final volume of 14 ml (pH at 1-2). Allowed the mixture to shake in a shaker at room temperature for 1 hr.

Added NaOH until pH was ~7.

Washed the precipitated material with water by filtration until the filtrate was clear.

Dried the material using a food dehydrator for 24 hr. Ground the material using a nut grinder.

With 0.1 gram of the dried composition, added 5 ml of a 20 mM phosphate solution (as in Example 1) and incubated at 37° C. for 3 hr. Centrifuged and collected the supernatant.

Determined the phosphate or iron level in the supernatants as in Example 8.

The swell volume of the composition after incubating with the phosphate buffer for 3 hr: 0.65 ml.

TABLE 18

Summary of the phosphate binding and the iron level in the supernatant of the composition

| Phosphate bound | Iron level |
|---|---|
| 0.23 mmol per g of dry composition | 8.4 µg per g of dry composition |

Example 18

Mixed 0.5 g gum Arabic into 10 ml of water. Added 2 ml of $FeCl_3$ (0.37 g/ml in water) into the fiber component. Added water to the final volume of 14 ml (pH at 1-2). Immediately added NaOH until pH was ~7. There was a formation of precipitates. Allowed the mixture to shake in a shaker at 60° C. for 1 hr. Cooled the mixture to be <30° C.

Washed the precipitated material with water by filtration until the filtrate was clear.

Dried the material using a food dehydrator for 24 hr. Ground the material using a nut grinder.

With 0.1 gram of the dried composition, added 5 ml of a 20 mM phosphate solution (as in Example 1) and incubated at 37° C. for 3 hr. Centrifuged and collected the supernatant.

Determined the phosphate level in the supernatant as in Example 8.

Phosphate bound was determined to be 0.22 mmol per g of dry composition.

Example 19

Sample 1: Mixed 0.5 g gum Arabic into 10 ml of water. Added 2 ml of $FeCl_2$ (Sigma 372870, 0.37 g/ml in water) into the fiber component. Added water to the final volume of 14 ml (pH at 3.0). Allowed the mixture to shake in a shaker at 60° C. for 1 hr. Cooled the mixture to be <30° C. Added NaOH until pH was ~7.

Sample 2: Mixed 0.5 g gum Arabic into 10 ml of water. Added 2 ml of iron(II) acetate (Sigma 339199, 0.37 g/ml in water) into the fiber component. Added water to the final volume of 14 ml (pH at 3.5). Allowed the mixture to shake in a shaker at 60° C. for 1 hr. Cooled the mixture to be <30° C. Added NaOH until pH was ~7.

Sample 3: Mixed 0.5 g gum Arabic into 10 ml of water. Added 2 ml of iron(II) L-ascorbate (Sigma A0207, 0.37 g/ml in water) into the fiber component. Added water to the final volume of 14 ml (pH at 4.6). Allowed the mixture to shake in a shaker at 60° C. for 1 hr. Cooled the mixture to be <30° C. Added NaOH and watched for the formation of precipitates. Very little precipitates were formed even at pH 13.

Sample 4: Mixed 0.5 g gum Arabic into 10 ml of water. Added 2 ml of $FeSO_4$ (Sigma 215422, 0.37 g/ml in water) into the fiber component. Added water to the final volume of 14 ml (pH at 3.7). Allowed the mixture to shake in a shaker at 60° C. for 1 hr. Cooled the mixture to be <30° C. Added NaOH and watched for the formation of precipitates. Very little precipitates were formed even at pH 13.

Sample 5: Mixed 0.5 g gum Arabic into 10 ml of water. Added 2 ml of iron(III) citrate (Sigma F6129, 0.37 g/ml in water) into the fiber component. Added water to the final volume of 14 ml (pH at 1.1). Allowed the mixture to shake in a shaker at 60° C. for 1 hr. Cooled the mixture to be <30° C. Added NaOH until pH was ~7.

Sample 6: Mixed 0.5 g gum Arabic into 10 ml of water. Added 2 ml of Fe phosphate (Sigma 436011, 0.37 g/ml in water) into the fiber component. Added water to the final volume of 14 ml (pH at 4.8). Allowed the mixture to shake in a shaker at 60° C. for 1 hr. Cooled the mixture to be <30° C. Added NaOH and watched for the formation of precipitates. Very little precipitates were formed even at pH 12.

Sample 7: Mixed 0.5 g gum Arabic into 10 ml of water. Added 2 ml of iron(III) pyrophosphate (Sigma P6526, 0.37 g/ml in water) into the fiber component. Added water to the final volume of 14 ml (pH at 6.1). Allowed the mixture to shake in a shaker at 60° C. for 1 hr. Cooled the mixture to be <30° C. Added NaOH until pH was ~7.

Washed the precipitated material with water by filtration until the filtrate was clear.

Dried the material using a food dehydrator for 24 hr. Ground the material using a nut grinder.

With 0.1 gram of the dried composition, added 5 ml of a 20 mM phosphate solution (as in Example 1) and incubated at 37° C. for 3 hr. Centrifuged and collected the supernatant.

For $FeSO_4$ (Sample 4), since very little precipitates were formed and only 0.05 g of dry material was recovered, 0.05 gram of the dried composition was mixed with 2.5 ml of a 20 mM phosphate solution (as in Example 1) and incubated at 37° C. for 3 hr. Centrifuged and collected the supernatant.

Determined the phosphate level in the supernatants as in Example 8.

TABLE 19

Summary of the phosphate levels in the supernatants of the compositions

| Sample # | Phosphate bound |
|---|---|
| Sample 1 | 0.19 mmol per g of dry composition |
| Sample 2 | 0.17 mmol per g of dry composition |
| Sample 3 | 0.13 mmol per g of dry composition |
| Sample 4 | 0.24 mmol per g of dry composition |
| Sample 5 | 0.11 mmol per g of dry composition |
| Sample 6 | 0 mmol per g of dry composition |
| Sample 7 | 0 mmol per g of dry composition |

Example 20

Mixed 0.5 g gum Arabic into 10 ml of water. Neutralized 2 ml of $FeCl_3$ (0.37 g/ml in water) with NaOH until pH was ~7. There was a formation of precipitates. Combined the fiber component with the neutralized Fe solution. Added water to the final volume of 14 ml. Allowed the mixture to shake in a shaker at 60° C. for 1 hr. Cooled the mixture to be <30° C. Washed the precipitated material with water by filtration until the filtrate was clear. Very little precipitates were retained.

Dried the material using a food dehydrator for 24 hr. Ground the material using a nut grinder.

With 0.1 gram of the dried composition, added 5 ml of a 20 mM phosphate solution (as in Example 1) and incubated at 37° C. for 3 hr. Centrifuged and collected the supernatant.

Determined the phosphate level in the supernatants as in Example 8.

Phosphate bound was determined to be 0.09 mmol per g of dry composition.

Example 21

The dry iron-gum Arabic composition from Example 13 was analyzed further by FT/IR spectroscopy (Fourier Transform Infrared; JASCO FT/IR-4100). Plain gum Arabic was used as a control. The result is consistent with the chemical composition of gum Arabic as the main component of the complex.

Figure 25A:
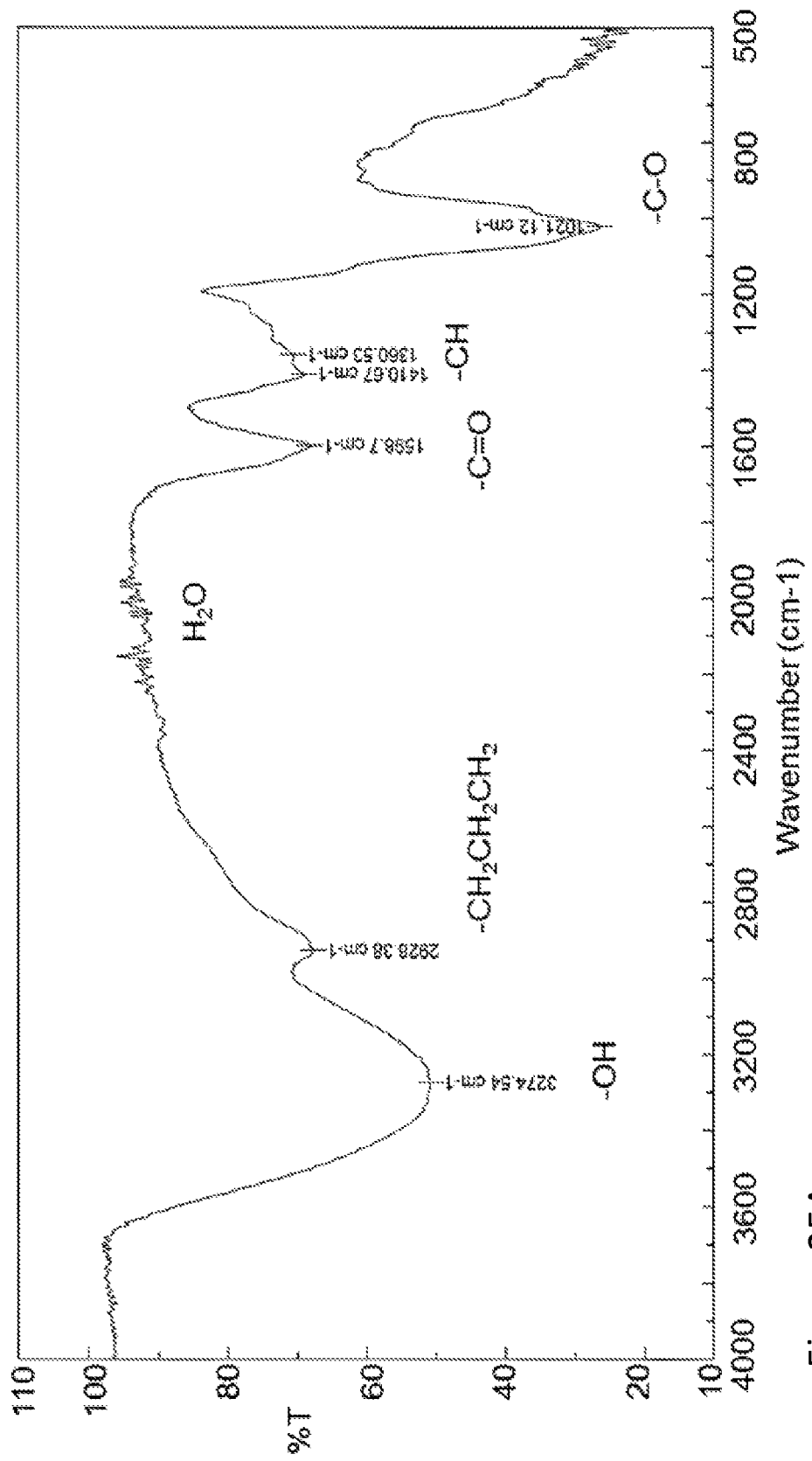
FIG. 25 illustrates the FT/IR spectroscopy of (FIG. 25A) the iron-gum Arabic composition and (FIG. 25B) the gum Arabic alone.
Figure 25B:
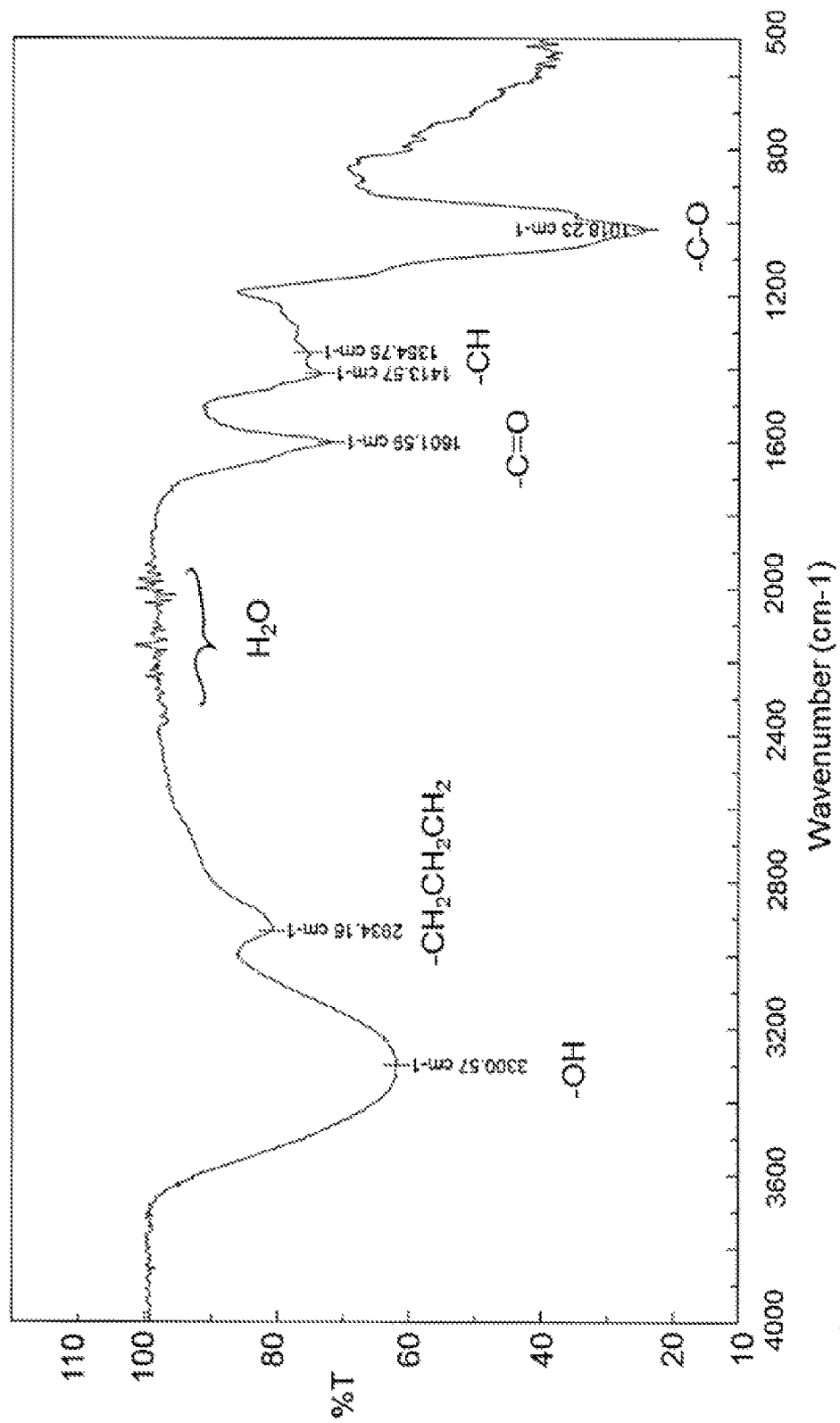

A representative result is shown in FIG. 25.

Example 22

The iron-gum Arabic composition can be analyzed by solid phase NMR.

The dry iron-gum Arabic composition from Example 13 was analyzed by a 750 MHz solid-state NMR spectroscopy (Model 750 spinning at 30 kHz plus).

Figure 26B:
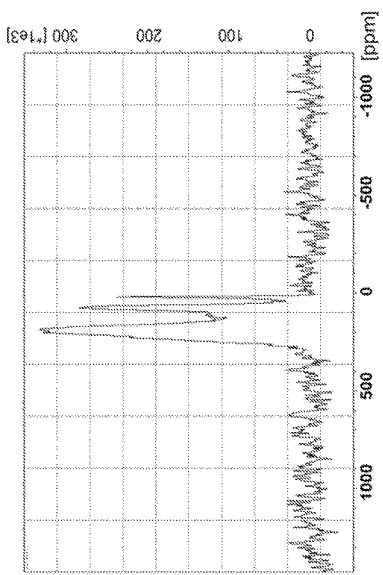
FIG. 26 shows the $^{13}$C-NMR results from solid-state NMR spectroscopy.
(FIG. 26A) the iron-gum Arabic composition and (FIG. 26B) unprocessed gum Arabic.
Figure 26A:
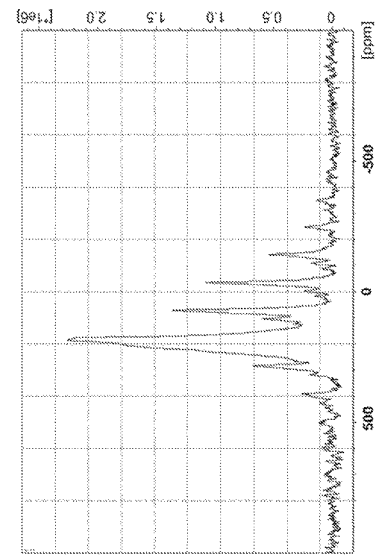

FIG. 26 shows the solid $^{13}$C-NMR spectra for Composition 1 (iron-gum Arabic) vs. gum Arabic (unprocessed).

The iron-gum Arabic composition was not only insoluble in water, but also insoluble in ethanol and DMSO.

Example 23

Studies were conducted in vitro to examine the potential drug interaction effect of the iron-gum Arabic composition.

An enalapril or ciprofloxacin stock solution at 10 mg/ml in water was prepared. The dry iron-gum Arabic composition from Example 11 or Renvela at 0.1 g/tube was incubated with 1.5 ml water plus 0.5 ml of enalapril or ciprofloxacin stock solution (5 mg per sample) for 1 hr at room temperature (RT=22° C.). The samples were centrifuged and the supernatants collected. The precipitates were washed with 2 ml water per sample for 3 times. The supernatants were pooled. A tube with enalapril or ciprofloxacin only was prepared as the standard. All samples were adjusted to the same volume as the standard tube. An aliquot of 2 ml per sample was prepared for HPLC analysis.

For warfarin and digoxin, a stock solution at 5 mg/ml in ethanol was prepared. The iron-gum Arabic composition, or Renvela at 0.1 g/tube was incubated with 1 ml of warfarin or digoxin stock solution (5 mg per sample) for 1 hr at room temperature (RT=22° C.). The samples were centrifuged and the supernatants collected. The precipitates were washed with 2 ml ethanol per sample for 3 times. The supernatants were pooled. A tube with warfarin or digoxin only was prepared as the standard. All samples were adjusted to the same volume as the standard tube.

Samples were centrifuged at 12,000×g for 10 min and the supernatant was evaporated to dryness and reconstituted in 1 ml of initial LC solvent, and 10 µl was injected into the HPLC system.

The apparatus employed was a Shimadzu LC-20AD HPLC-PDA-ITTOF. The HPLC consists of a degasser, binary pumping system, auto sampler with a 50 µl sample loop. Standards were scanned by PDA (Photo Diode Array) using a deuterium lamp for UV and Tungsten lamp for visible light to determine the absorbance wavelength for each compound. The PDA scanned all UV light between 200-400 nm. A linear gradient starting at a 5:95% (0.1% formic acid/acetonitrile, v/v) was ramped to 95:5% (acetonitrile/0.1% formic acid, v/v) over 10 min, then re-equilibrated for 5 min at initial conditions. LC solutions version 3.5 (Shimadzu) was used. All solvents are LC-MS grade (0.2 µm filtered), the water is from our in house Siemens filtration system (18.2 mΩ). The flow rate was 0.3 ml/ml. Total run time was 15 min. A Waters C18 BEH column (2.1×50 mm, 1.8 um) was utilized.

The compound of interest was confirmed by mass spectrometry at 100-1000 m/z (a Shimadzu ion trap-time of flight).

FIG. 27 shows a representative HPLC profile for the digoxin standard vs. the iron-gum Arabic composition-treated digoxin sample. The results are summarized in Table 20.

TABLE 20

Results of HPLC profile for digoxin standard vs the iron-gum Arabic standard

| Drug | Sample | Area under Curve | Effect |
|---|---|---|---|
| Enalapril | STD | 25848840 | — |
|  | Composition 1 | 23874466 | No effect |
|  | Renvela | 22181036 | No effect |
| Ciprofloxacin | STD | 26472485 | — |
|  | Composition 1 | 20228182 | 24% absorption |
|  | Renvela | 11108859 | >50% absorption |
| Warfarin | STD | 33626573 | — |
|  | Composition 1 | 35539988 | No effect |
|  | Renvela | 35082215 | No effect |
| Digoxin | STD | 11543124 | — |
|  | Composition 1 | 12199043 | No effect |
|  | Renvela | 13742646 | No effect |

The in vitro results are consistent with the current understanding that Renagel (or Renvela) capsules at approximately 2.8 g decrease the bioavailability of ciprofloxacin by approximately 50% in healthy subjects, but has no effect on digoxin, enalapril and warfarin (information cited from Renagel or Renvela package insert).

Example 24

Mixed 0.5 g gum Arabic into 15 ml of water. Added MgCl$_2$ (EM Science MX0045, 1 g of MgCl$_2$ in 2 ml of water) into the fiber component. Added HCl till pH at 1-2. Added water till the final volume was 20 ml. The mixture was completely soluble in water. Allowed the mixture to incubate at 60° C. for 1 hr. Cooled the mixture to be <30° C.

Added NaOH. After addition of NaOH, precipitates formed starting at pH=3. More precipitates were formed at pH=6 or 9.

Washed the precipitated material with 50 ml of water for three times. Collected precipitates by centrifugation.

Dried the material using a food dehydrator.

With 0.1 gram of the dried composition, added 5 ml of a 20 mM phosphate solution (as in Example 1) and incubated at room temperature for 16 hr. Centrifuged and collected the supernatant.

Determined the phosphate level in the supernatants using the phosphate colorimetric assay (Catalog #K410-500 from BioVision). Normalized the amount of phosphate bound by the quantity of the composition used (i.e. 0.1 g)

FIG. 28A shows the appearance of gum Arabic plus MgCl$_2$ in water; the materials were completely soluble in water.

FIG. 28B shows the appearance of the component after addition of NaOH until pH was 9.

FIG. 28C shows the appearance of the dried precipitate.

Table 21 summarizes the phosphate binding results.

TABLE 21

Phosphate binding of Mg-gum Arabic

| Composition | Phosphate bound |
|---|---|
| Mg-gum Arabic | 0.13 mmol per g of dry composition |

Example 25

Mixed 0.5 g gum Arabic into 15 ml of water. Pre-heated at 60° C.

Added 0.5 g, 1 g, 2 g, 4 g of $MgCl_2$ (in 2 ml water) into the fiber component mixture (pH ranging from 4 to 5). Added HCl till pH at 1-2. Added water till the final volume was 22.5 ml. The mixture was completely soluble in water. Allowed the mixture to incubate at 60° C. for 1 hr. Cooled the mixture to be <30° C.

Added NaOH until pH was 9.

Washed the precipitated material with 50 ml of water for three times. Collected precipitates by centrifugation.

Dried the material using a food dehydrator.

With 0.05 gram of the dried composition, added 5 ml of a 20 mM phosphate solution (as in Example 1) to each sample and incubated at 37° C. for 3 hr. Centrifuged and collected the supernatant.

Determined the phosphate level in the supernatants using the phosphate colorimetric assay (Catalog #K410-500 from BioVision). Normalized the amount of phosphate bound by the quantity of the composition used (i.e. 0.05 g).

TABLE 22

Summary of phosphate binding of the compositions.

| Tube # | Phosphate bound at 3 hr, per g of dry composition |
|---|---|
| 1 | 0.26 mmol |
| 2 | 0.55 mmol |
| 3 | 0.32 mmol |
| 4* | 0.46 mmol |

*Tube # 1-4 indicated the samples with the addition of 0.5 g, 1 g, 2 g, 4 g of $MgCl_2$

Example 26

Mixed 0.5 g gum Arabic into 15 ml of water. Pre-heated at 60° C.

Added 1 g of different metal ions (as shown in Table 23) in 2 ml water into the fiber component mixture. Determined the pH of the mixture.

TABLE 23

Reactant Amounts and pH of the mixture

| Source | Metal ion (M) | g | ml | pH |
|---|---|---|---|---|
| CX0180-1 (EM science) | $CaCl_2$ | 1 g | 2 ml | ~4 |
| P217 (Fisher Chem) | KCl | 1 g | 2 ml | ~5 |
| 344702 (Sigma) | $MgPO_4$ | 1 g | 2 ml | 6-7 |
| 230391 (Sigma) | $MgSO_4$ | 1 g | 2 ml | ~5 |
| CDS000001 (Sigma) | Mg citrate | 1 g | 2 ml | ~4 |
| 204986 (Sigma) | $ZnSO_4$ | 1 g | 2 ml | 4-5 |
| 480762 (Sigma) | Zn citrate | 1 g | 2 ml | 5-6 |
| C4124 (Sigma) | Chromium picolinate | 1 g | 2 ml | 4-5 |
| 233706 (Sigma) | Vanadyl sulfate | 1 g | 2 ml | 2-3 |

Added HCl till pH at 1-2. Added water till the final volume was 20 ml. The mixtures with Zn citrate and chromium picolinate were not completely soluble; all the other samples were completely soluble in water. Allowed the mixture to incubate at 60° C. for 1 hr. Cooled the mixture to be <30° C.

Added NaOH until pH was >7, or until the formation of precipitates was visible. There was no formation of precipitates in the samples with $CaCl_2$, KCl, and Mg citrate even at pH >10.

Washed the precipitated material with 50 ml of water for three times. Collected precipitates by centrifugation.

Dried the material using a food dehydrator.

With 0.1 gram of the dried composition, added 5 ml of a 20 mM phosphate solution (as in Example 1) to each sample and incubated at room temperature for 24 hr. Centrifuged and collected the supernatant.

Determined the phosphate level in the supernatants using the phosphate colorimetric assay (Catalog #K410-500 from BioVision). Normalized the amount of phosphate bound by the quantity of the composition used (i.e. 0.05 g).

TABLE 24

Summary of phosphate binding of the metal ion-fiber component compositions

| Metal ion (in gum Arabic) | Phosphate bound, per g of dry composition |
|---|---|
| $MgPO_4$ | 0.02 mmol |
| $MgSO_4$ | 0.67 mmol |
| $ZnSO_4$ | 0.30 mmol |
| Zn citrate | 0.60 mmol |
| Chromium picolinate | 0.13 mmol |
| Vanadyl sulfate | 0.12 mmol |

Example 27

Mixed 0.5 g gum Arabic into 15 ml of water. Pre-heated at 60° C. Added a mixture of different metal ions in 2 ml water (as shown in Table 25) into the fiber component mixture. Determined the pH of the mixture.

TABLE 25

Metal ion mixture

| First metal ion | Second metal ion | pH |
|---|---|---|
| 0.5 g $FeCl_3$ | 0.5 g $CaCl_2$ | <2 |
| 1 g lanthanum carbonate (Sigma 325767) | — | ~7 |
| 0.5 g $FeCl_3$ | 0.5 g $MgPO_4$ | <2 |
| 0.5 g $FeCl_3$ | 0.5 g Zn citrate | <2 |

Added HCl to the lanthanum carbonate sample till pH at 1-2. Added water to each sample till the final volume was 20 ml. The mixture with lanthanum carbonate was not completely soluble; all the other samples were completely soluble in water. Allowed the mixture to incubate at 60° C. for 1 hr. Cooled the mixture to be <30° C.

Added NaOH until pH was >7, or until the formation of precipitates was visible. There was very little formation of precipitates in the sample with Zn citrate.

Washed the precipitated material with 50 ml of water for five times. Collected precipitates by centrifugation.

Dried the material using a food dehydrator.

With 0.1 gram of the dried composition, added 5 ml of a 20 mM phosphateh solution (as in Example 1) to each sample and incubated at room temperature for 24 hr. Centrifuged and collected the supernatant.

Determined the phosphate level in the supernatants using the phosphate colorimetric assay (Catalog #K410-500 from BioVision). Normalized the amount of phosphate bound by the quantity of the composition used (i.e. 0.05 g).

TABLE 26

Summary of phosphate binding of the mixed
metal ion-fiber component compositions

| Metal ion (in gum Arabic) | Phosphate bound at 24 hr, per g of dry composition |
|---|---|
| $FeCl_3/MgCl_2$ | 0.54 mmol |
| Lanthanum carbonate | 0.46 mmol |
| $FeCl_3/MgPO_4$ | 0.57 mmol |
| $FeCl_3$ | 0.44 mmol |

Example 28

Sample #4 from Example 26 was analyzed by the XPS as described above.

Figure 29A:
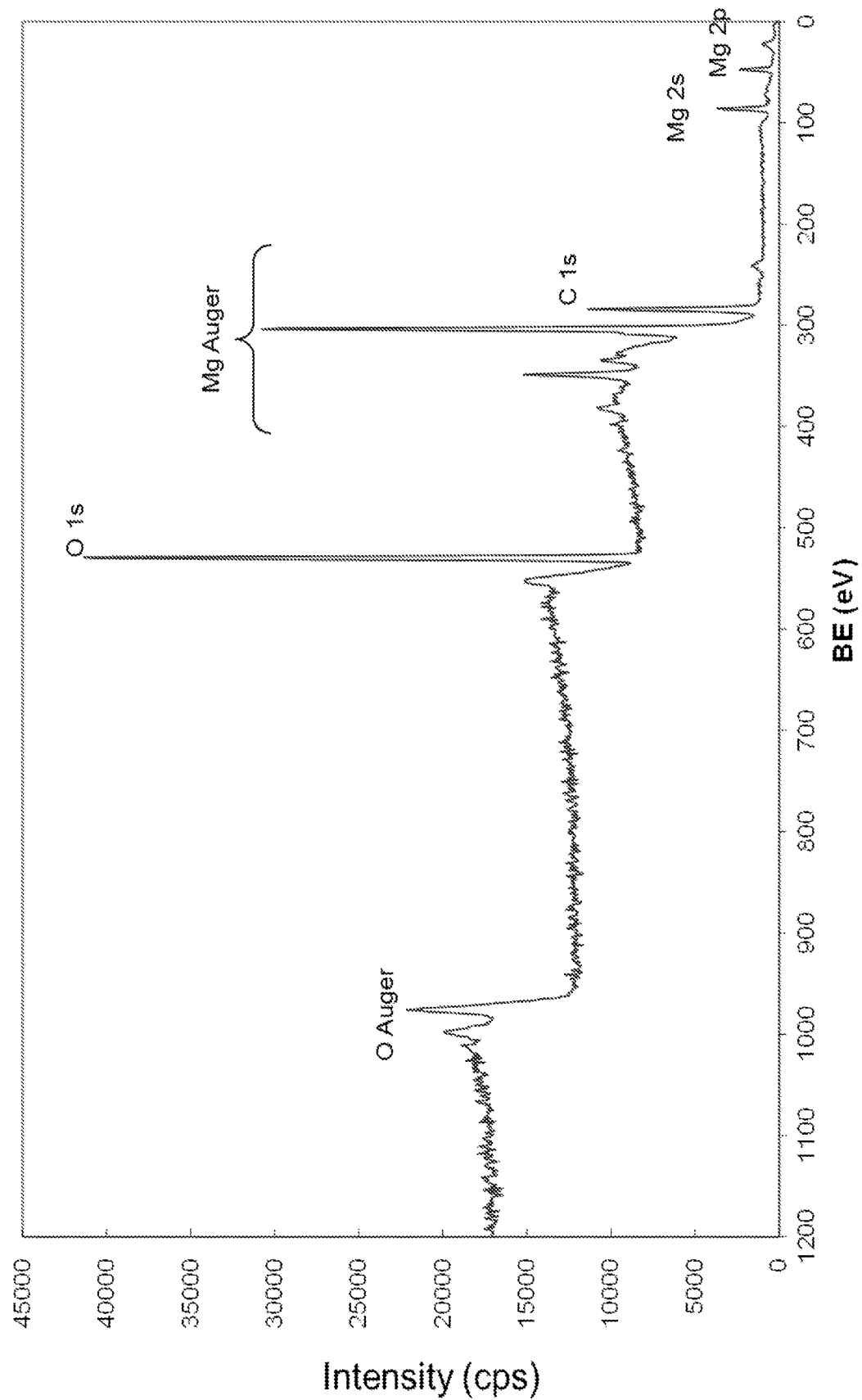
(FIG. 29A) the survey spectrum, (FIG. 29B) C 1s, (FIG. 29C) Mg 2p.

FIG. 29A shows the survey spectra from the XPS analysis. The semi-quantitation data are listed in Table 27.

TABLE 27

XPS analysis results for Sample #4 (from Example 26)

| Peak | Position BE (eV) | FWHM (eV) | Raw Area (CPS) | RSF | Atomic Mass | Atomic Conc, % | Mass Conc, % |
|---|---|---|---|---|---|---|---|
| Mg 2p | 48.000 | 2.826 | 5668.7 | 0.168 | 24.31 | 10.41 | 16.60 |
| O 1s | 529.000 | 3.702 | 127748.9 | 0.780 | 15.999 | 48.93 | 51.36 |
| C 1s | 284.000 | 3.536 | 38075.7 | 0.278 | 12.011 | 40.67 | 32.05 |

Figure 29B:
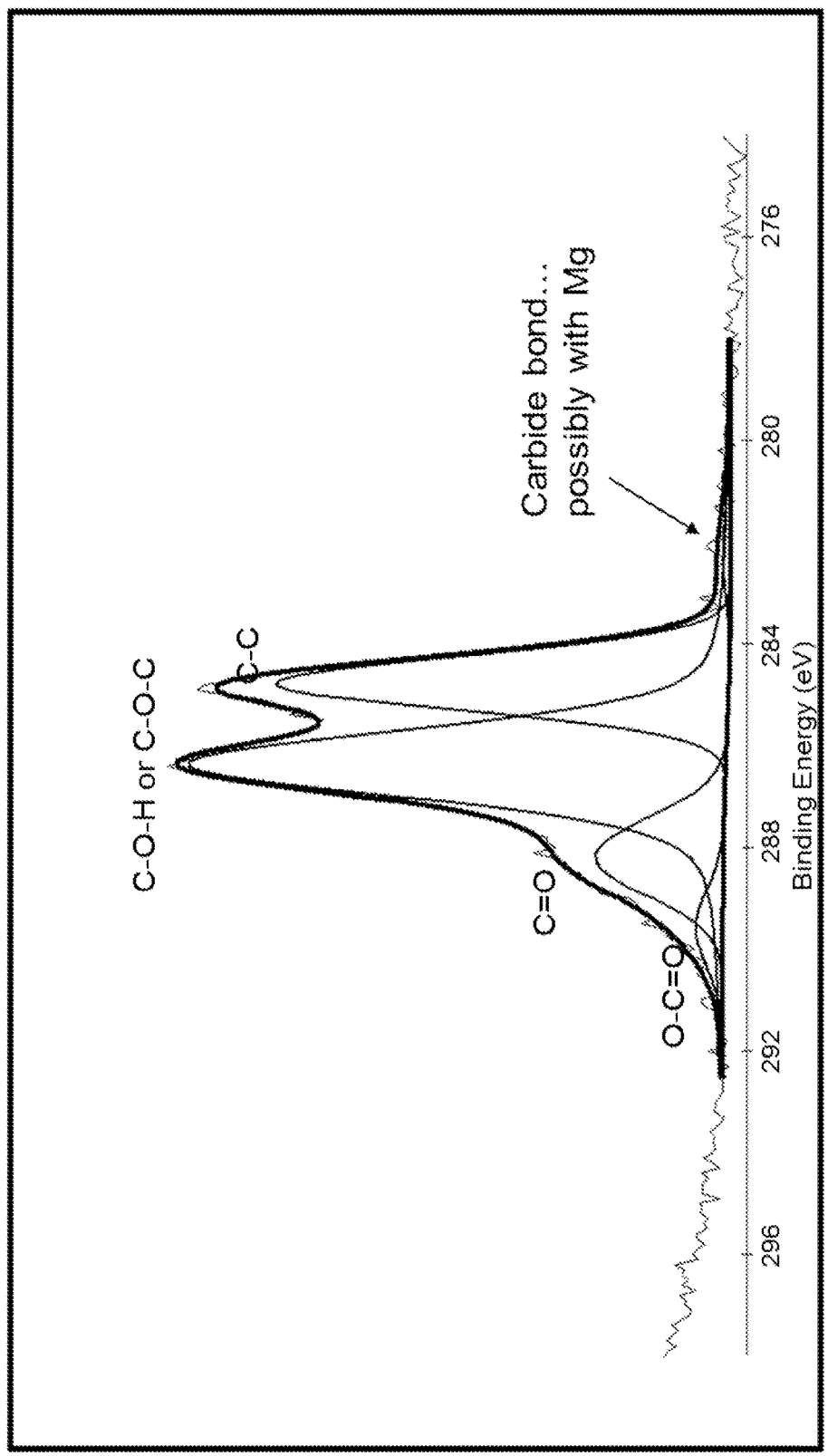
FIG. 29 shows spectra from XPS analysis of Mg-gum Arabic composition.

FIG. 29B shows the C 1s spectrum. The result is consistent with the chemical composition of gum Arabic as the main component of the complex.

Figure 29C:
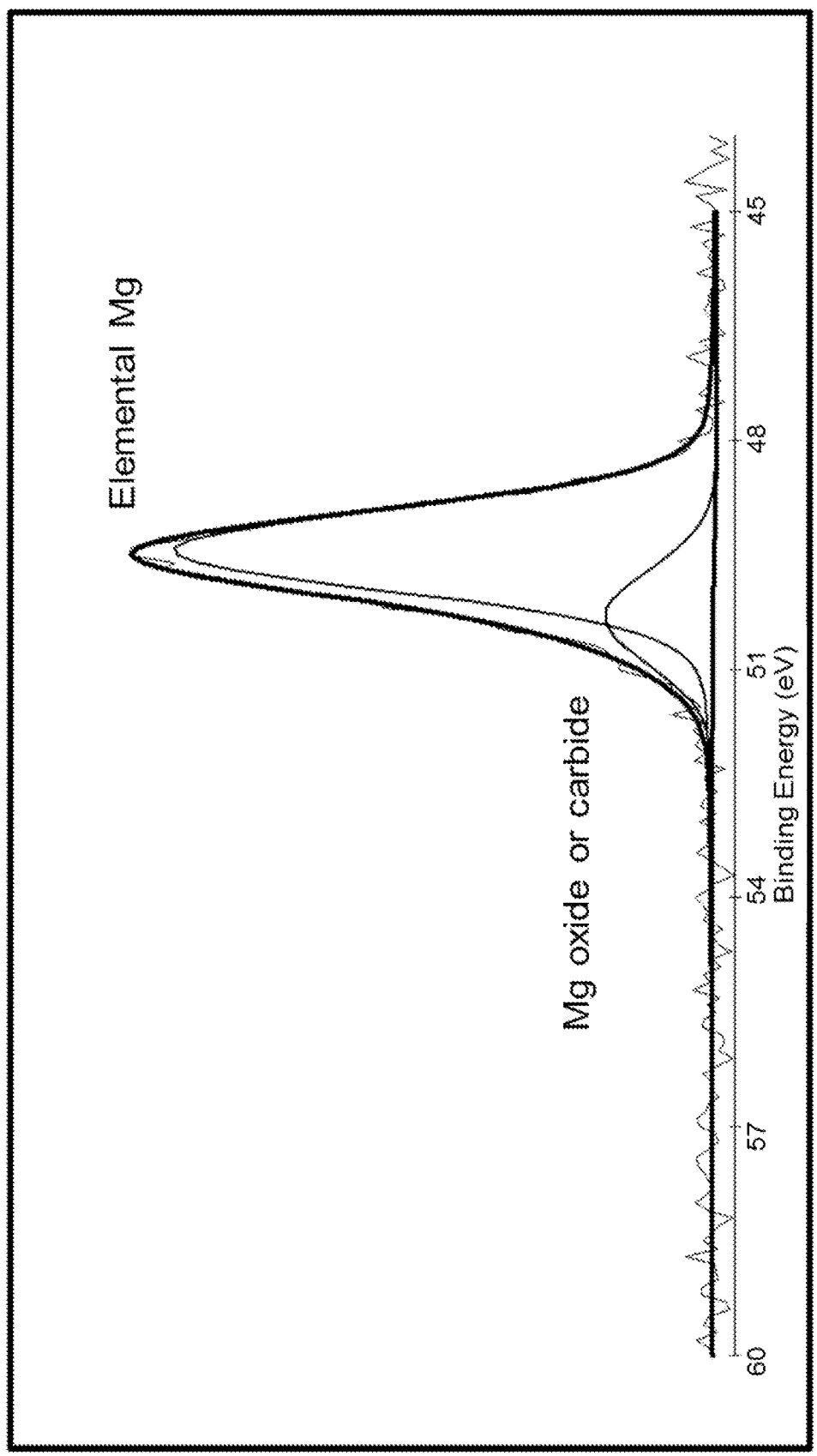

FIG. 29C shows the Mg 2p spectrum. The result indicates the presence of magnesium ion, and the potential interaction between magnesium ion and oxygen or carbon.

Example 29

0.1 gram of Sample #4 from Example 26 was incubated with 5 ml of a 20 mM phosphate solution (as in Example 1) at room temperature for 24 hr. Centrifuged and collected the supernatant.

Determined the Mg level in the supernatant using the Stanbio LiquiColor magnesium assay kit (Catalog #0130, Stanbio, Boerne, Tex.).

The Mg released into the supernatant was 2.2 mg/g of dry composition, which was calculated to be 1.32%.

Example 30

$^{57}$Fe Mössbauer spectroscopy was used to study Composition 1. The measurements were performed using a MS4 spectrometer operating in the constant acceleration mode in transmission geometry. For low temperature measurements a Janis SVT-400 cryostat was used. A 100 mCi $^{57}$Co in Rh held at room temperature (RT) was used as source. Three measurements were done; i) at RT with zero external magnetic field, ii) at 80 K with zero external magnetic field, and iii) at 80 K with 77 mT external magnetic field perpendicular to the incoming γ-rays. All centroid shifts, δ, are given with respect to metallic α-iron at RT. The spectra were least square fitted using Recoil software (Lagarec et al., Mössbauer Spectral Analysis Software for Windows, 1.0; Department of Physics, University of Ottawa: Canada, 1998).

The parameters from these fittings, which are centroid shift (δ), quadrupole splitting ($\Delta E_Q$), Lorentzian linewidth (Γ) and intensity (I) are summarized in Table 28 (Estimated errors are in I±3%, and in δ and $\Delta E_Q$±0.005 mm/s, and in Γ±0.01 mm/s).

TABLE 28

Results of analysis of Composition 1 by
$^{57}$Fe Mössbauer spectroscopy

| Sample | Composition 1 | | |
|---|---|---|---|
| Temp | T = 300 K | T = 80 K | T = 80 K |
| Field | | | B = 77 mT |
| $\delta_1$ (mm/s) | 0.350 | 0.465 | 0.465 |
| $\Delta E_{Q1}$ (mm/s) | 0.981 | 1.025 | 1.071 |
| $\Gamma_1$ (mm/s) | 0.40 | 0.46 | 0.51 |
| $I_1$ (%) | 32 | 42 | 42 |
| $\delta_2$ (mm/s) | 0.352 | 0.460 | 0.462 |
| $\Delta E_{Q2}$ (mm/s) | 0.578 | 0.590 | 0.590 |
| $\Gamma_2$ (mm/s) | 0.37 | 0.43 | 0.51 |
| $I_2$ (%) | 58 | 58 | 58 |

Figure 30:
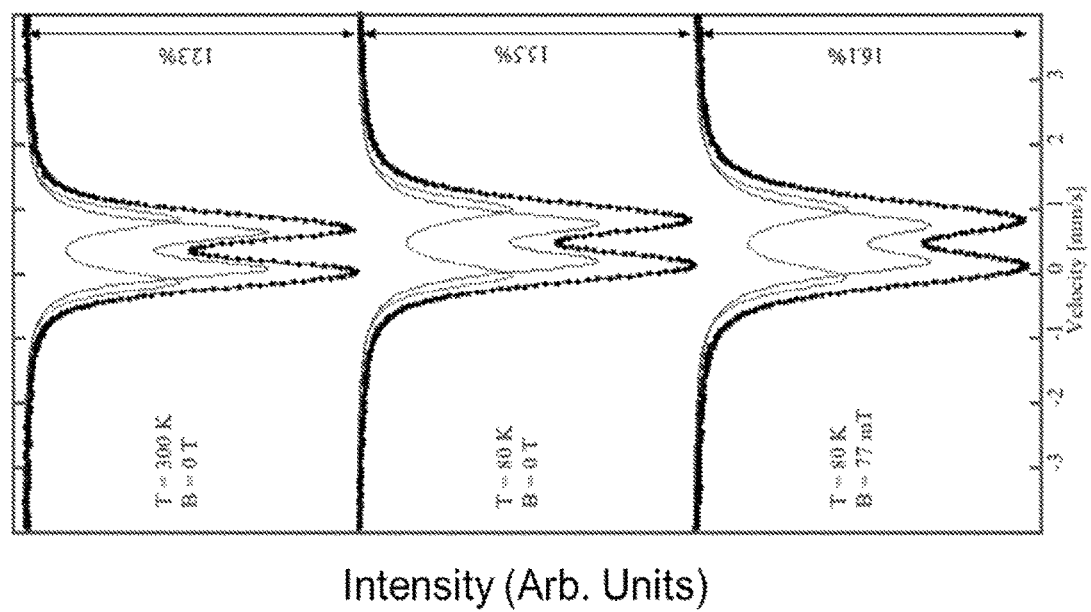
FIG. 30 illustrates the $^{57}$Fe Mössbauer spectra.

The spectra are depicted in FIG. 30.

δ in Mössbauer spectroscopy is a good indicator of the oxidation state of the Fe atom via measuring of the s-electron density at the $^{57}$Fe nucleus. For example high-spin $Fe^{+3}$ vs. $Fe^{+2}$ have δ of about 0.25 mm/s vs. 0.70 mm/s in FeS clusters at RT (Amon et al., Nature, 1957, 180:182). In $[Fe_4S_4]^{+2}$, where there are two pairs of $Fe^{+2}Fe^{+3}$, there is one delocalized electron hopping between the $Fe^{+2}$ and $Fe^{+3}$ giving rise to a pair of delocalized $Fe^{+2.5}Fe^{+2.5}$ with δ of about 0.50. The δ value of 0.351 mm/s indicates that all Fe atoms in this sample are in high-spin $Fe^{+3}$ state. $Fe^{3+}$ is likely associated with oxygen to provide electronegativity.

Various embodiments of this invention are described herein. Variations may become apparent to those of ordinary skill in the art upon reading the foregoing description. The inventors expect skilled artisans to employ such variations as appropriate, and the inventors intend for the invention to be practiced otherwise than as specifically described herein. Accordingly, the inventors contemplate all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A water-insoluble composition comprising a metal ion M in an oxidation number of Z (M(Z)) or mixtures thereof complexed to gum Arabic, with at least 2 wt % of metal ion bound in the complex, wherein Z is an integer selected from 1 to 8 (I to VIII) or pharmaceutically acceptable salts thereof.

2. The composition of claim 1, wherein the metal ion (M) is selected from the group consisting of lithium, sodium, potassium, rubidium, cesium, francium, beryllium, magnesium, calcium, strontium, barium, radium, scandium, yttrium, lanthanum, actinium, titanium, zirconium, hafnium, vanadium, niobium, tantalum, chromium, molybdenum, manganese, iron, cobalt, nickel, copper, zinc, aluminum, bismuth and mixtures thereof.

3. The composition of claim 1, wherein the metal ion (M) is iron in the form of a Fe (II) and/or Fe(III) salt selected from the group consisting of iron(II) acetate, iron(III) acetate, iron(II) citrate, iron(III) citrate, iron(II) ascorbate, iron(III) ascorbate, iron(II) oxalate, iron(III) oxalate, iron(II) oxide, iron(III) oxide, iron(II) carbonate, iron(III) carbonate, iron(II) carbonate saccharate, iron(III) carbonate saccharate, iron(II) formate, iron(III) formate, iron(II) sulfate, iron(III) sulfate, iron(II) chloride, iron(III) chloride, iron (II) bromide, iron (III) bromide, iron (II) iodide, iron (III) iodide, iron (II) fluoride, iron (III) fluoride, iron(II) acetylacetonate, iron(III) acetylacetonate, iron (II) phosphate, iron (III) phosphate, iron (II) pyrophosphate, iron (III) pyrophosphate, and combinations thereof.

4. The composition of claim 1, wherein the oxidation number of the metal ion is selected from +1, +2 and +3 or mixtures thereof.

5. The composition of claim 1 comprising Fe(II) and/or Fe(III) complexed to gum Arabic, wherein the both the Fe(II) and/or Fe(III) are bound to gum Arabic without iron release/availability to affect systemic iron levels.

6. The composition of claim 1, wherein the composition is a water-insoluble metal ion gum Arabic complex, having a density of >1.1 g/ml in a loose powder form and a density of >1.5 g/mL in its compressed dry form.

7. The composition of claim 1, wherein gum Arabic is water soluble before reacting with metal ions.

8. The composition of claim 1, wherein the metal ion-gum Arabic component complex comprises at least 2 wt % of the one or more metal ions and at least 10 wt % of gum Arabic, 2 to 50 wt % of the metal ions and 50 to 98 wt % of gum Arabic, 10 to 50 wt % of the metal ions and 50 to 90 wt % of gum Arabic, 10 to 40 wt % of the metal ions and 60 to 90 wt % of gum Arabic, or 15 to 30 wt % of the metal ions and 70 to 85 wt % of gum Arabic.

9. The composition of claim 1, wherein the complex is crystalline, amorphous or comprises microdomains of both amorphous and crystalline regions ranging from 10% to 90% amorphous and 10% to 90% crystalline.

10. The composition of claim 1, wherein said metal ion-gum Arabic complex is capable of binding minerals, ions, toxins, metabolites within a pH range of about 1 to about 12, and/or wherein said metal ion-gum Arabic complex is capable of binding excess phosphates and toxins in GI tract, and/or wherein the metal ion-gum Arabic complex is stable at a pH 1 to 12, and remains efficacious at a pH range between 1 to 12.

11. A process for preparing a metal ion-gum Arabic complex comprising the steps of: (a) mixing gum Arabic and a metal ion compound or a mixture of metal ion compounds, at a pH <7; (b) maintaining a temperature of reaction mixture of step (a) between ambient and 100° C.; (c) cooling the reaction mixture of step (b) to be <40° C.; (d) adjusting the pH using base until precipitates are formed; and (e) washing until pH is neutral; and (f) isolating the metal ion-gum Arabic complex formed, wherein the metal ion content is in an amount of from 2 to 50 wt %.

12. The process of claim 11, wherein the pH at step (a) is between about 1 and about 4, and wherein a pH <7 is reached by addition of an acid selected from the group consisting of: hydrochloric acid (HCl), hydrobromic acid (HBr), hydroiodic acid (HI), hypochlorous acid (HClO), chlorous acid ($HClO_2$), chloric acid ($HClO_3$), perchloric acid ($HClO_4$), and corresponding acids for bromine and iodine, sulfuric acid ($H_2SO_4$), fluorosulfuric acid ($HSO_3F$), nitric acid ($HNO_3$), phosphoric acid ($H_3PO4$), fluoroantimonic acid ($HSbF_6$), fluoroboric acid ($HBF_4$), hexafluorophosphoric acid ($HPF_6$), chromic acid ($H_2CrO_4$), and boric acid ($H_3BO_3$) and/or wherein the step (d) comprises addition of a base selected from LiOH, KOH, NaOH, $NaHCO_3$, $Na_2CO_3$, $Ca(OH)_2$, $Mg(OH)_2$, $Li_2CO_3$, $K_2CO_3$, $CaCO_3$, and $MgCO_3$, and/or wherein the reaction mixture is optionally exposed to pressure during step (b).

13. A pharmaceutical composition comprising (i) a compound or a pharmaceutically acceptable salt thereof of claim 1 and (ii) a pharmaceutically acceptable carrier.

14. The composition of claim 1, wherein the composition is formulated as a nutritional supplement, a beverage, a snack bar, or a cereal, or a medicament, or a medical food, suitable for oral administration.

15. The composition of claim 13 in a method of treating a subject suffering from hyperphosphatemia, hyperkalemia, hypercalcemia, hyperlipidemia, toxins from infectious agents, fluid and salt overload, abnormal mineral homeostasis with elevated calcium, phosphate, potassium, sodium in blood outside the normal range, or abnormal metabolic parameters selected from glucose, insulin, GLP-1, glucagon, glycerol, triglycerides, cholesterol, NEFA and leptin levels, the method comprising administering to the subject an effective amount of the composition, wherein the effective amount is about 0.005 g/kg/day to about 50 g/kg/day.

16. The composition of claim 1, formulated for use according to extracorporeal, ex vivo, or in vitro administration to a subject in need thereof, the composition being optionally embedded in an extracorporeal system for adsorbing excess calcium, cholesterol, phosphate, potassium, sodium, or toxins.

17. An elemental medical food or food supplement comprising at least 10 mg of the composition of claim 1 in a physiological carrier, optionally formulated as a liquid solution, a pill, a tablet, a powder, a bar, a wafer, a suspensions in an appropriate liquid, or a suitable emulsion, and optionally further comprising one or more ingredients selected from the group consisting of natural flavors, artificial flavors, major trace and ultra-trace minerals, minerals, vitamins, oats, nuts, spice, milk, egg, salt, flour, lecithin, xanthan gum, and sweetening agents.

18. An elemental medical food or food supplement suitable for mammals comprising at least 10 mg of the metal ion-gum Arabic composition according to claim 1 for maintaining bone health, gastrointestinal tract health, normal mineral homeostasis with calcium, phosphate, potassium, sodium in blood in the normal range, a normal lipid profile and cardiovascular health, or normal weight or normal metabolic parameters (glucose, insulin, GLP-1, glucagon, glycerol, triglycerides, cholesterol, NEFA and leptin levels in the normal range) the method comprising providing an effective amount of the food supplement to a subject.

* * * * *

UNITED STATES PATENT AND TRADEMARK OFFICE
CERTIFICATE OF CORRECTION

Page 1 of 1

PATENT NO.        : 9,796,792 B2
APPLICATION NO.   : 14/765087
DATED             : October 24, 2017
INVENTOR(S)       : Jinshyun Ruth Wu-Wong It is certified that error appears in the above-identified patent and that said Letters Patent is hereby corrected as shown below:

In the Specification

Column 1, Line 16, immediately prior to the FIELD OF THE INVENTION, add the following:
--STATEMENT OF GOVERNMENT INTEREST
This invention was made with support under Grant Number DK096698 awarded by the National Institutes of Health. The Government has certain rights in the invention.--

Signed and Sealed this
Nineteenth Day of June, 2018

Andrei Iancu
*Director of the United States Patent and Trademark Office*